(12) United States Patent
Chiou et al.

(10) Patent No.: US 10,435,661 B2
(45) Date of Patent: Oct. 8, 2019

(54) PHOTOTHERMAL SUBSTRATES FOR SELECTIVE TRANSFECTION OF CELLS

(71) Applicant: The Regents of the University of California, Oakland, CA (US)

(72) Inventors: Pei-Yu E. Chiou, Los Angeles, CA (US); Ting-Hsiang S. Wu, Culver City, CA (US); Sheraz Kalim Butt, Pomona, CA (US); Michael A. Teitell, Tarzana, CA (US)

(73) Assignee: The Regents of the University of California, Oakland, CA (US)

( * ) Notice: Subject to any disclaimer, the term of this patent is extended or adjusted under 35 U.S.C. 154(b) by 357 days.

(21) Appl. No.: 14/523,254

(22) Filed: Oct. 24, 2014

(65) Prior Publication Data

US 2015/0197720 A1    Jul. 16, 2015

Related U.S. Application Data

(63) Continuation of application No. 14/117,543, filed as application No. PCT/US2012/037810 on May 14, 2012, now abandoned.

(Continued)

(51) Int. Cl.
  *C12M 1/42* (2006.01)
  *C12N 15/87* (2006.01)
  (Continued)

(52) U.S. Cl.
  CPC ............ *C12M 35/02* (2013.01); *C12M 23/16* (2013.01); *C12M 23/20* (2013.01); *C12M 41/00* (2013.01);
  (Continued)

(58) Field of Classification Search
  CPC ...... C12M 35/02; C12M 23/16; C12M 23/20; C12M 41/00; C12M 41/08; C12N 13/00; C12N 15/87
  (Continued)

(56) References Cited

U.S. PATENT DOCUMENTS

| 4,917,462 A | 4/1990 | Lewis et al. |
| 5,080,586 A | 1/1992 | Kawai |

(Continued)

FOREIGN PATENT DOCUMENTS

| EP | 1 448 771 B1 | 1/2007 |
| JP | H01-141582 A | 6/1989 |

(Continued)

OTHER PUBLICATIONS

U.S. Requirement for Restriction/Election dated Jun. 2, 2014 issued in U.S. Appl. No. 12/667,594.

(Continued)

*Primary Examiner* — Michael L Hobbs
(74) *Attorney, Agent, or Firm* — Tom Hunter; Weaver Austin Villeneuve & Sampson LLP

(57) ABSTRACT

This invention provides novel tools for surgery on single cells and substrates/devices for delivery of reagents to selected cells. In certain embodiments the substrates comprise a surface comprising one or more orifices, where nanoparticles and/or a thin film is deposited on a surface of said orifice or near said orifice, where the nanoparticles and/or a thin film are formed of materials that heat up when contacted with electromagnetic radiation. In certain embodiments the pores are in fluid communication with microchannels containing one or more reagents to be delivered into the cells.

25 Claims, 30 Drawing Sheets

Related U.S. Application Data

(60) Provisional application No. 61/486,114, filed on May 13, 2011.

(51) Int. Cl.
  *C12N 13/00* (2006.01)
  *C12M 3/06* (2006.01)
  *C12M 1/00* (2006.01)
  *C12M 1/34* (2006.01)

(52) U.S. Cl.
  CPC ............. *C12M 41/08* (2013.01); *C12N 13/00* (2013.01); *C12N 15/87* (2013.01)

(58) Field of Classification Search
  USPC ....................................................... 435/285.1
  See application file for complete search history.

(56) References Cited

U.S. PATENT DOCUMENTS

| | | | |
|---|---|---|---|
| 5,310,674 | A | 5/1994 | Weinreb et al. |
| 6,468,657 | B1 | 10/2002 | Hou et al. |
| 6,866,885 | B1 | 3/2005 | Clough |
| 7,897,377 | B2 | 3/2011 | Stoppini |
| 2002/0099356 | A1 | 7/2002 | Unger et al. |
| 2003/0166181 | A1 | 9/2003 | Rubinsky et al. |
| 2003/0180946 | A1 | 9/2003 | Karube et al. |
| 2004/0079195 | A1 | 4/2004 | Perry et al. |
| 2004/0101822 | A1 | 5/2004 | Wiesner et al. |
| 2004/0158137 | A1 | 8/2004 | Eppstein et al. |
| 2006/0047254 | A1 | 3/2006 | Akahoshi et al. |
| 2006/0062902 | A1 | 3/2006 | Sager et al. |
| 2006/0110817 | A1* | 5/2006 | Nishiyama ............ B01L 3/0293 435/285.1 |
| 2006/0115971 | A1 | 6/2006 | Bau et al. |
| 2006/0251874 | A1 | 11/2006 | McClure et al. |
| 2008/0268540 | A1* | 10/2008 | Ito ......................... C12M 25/06 435/440 |
| 2010/0040549 | A1 | 2/2010 | Halas et al. |
| 2011/0117648 | A1 | 5/2011 | Chiou et al. |
| 2012/0245042 | A1 | 9/2012 | Liu et al. |
| 2015/0044751 | A1 | 2/2015 | Chiou et al. |
| 2016/0017340 | A1 | 1/2016 | Wu et al. |
| 2017/0175139 | A1 | 6/2017 | Wu et al. |

FOREIGN PATENT DOCUMENTS

| | | | |
|---|---|---|---|
| JP | H08-290377 | A | 11/1996 |
| JP | 2000-023657 | A | 1/2000 |
| JP | 2004-041023 | A | 2/2004 |
| JP | 2005-510236 | A | 4/2005 |
| JP | 2006-515758 | A | 6/2006 |
| WO | WO 99/46588 | | 9/1999 |
| WO | WO 2003/083480 | A1 | 10/2003 |
| WO | WO 2004/063350 | A2 | 7/2004 |
| WO | WO 2007/008609 | A2 | 1/2007 |
| WO | WO 2008/073851 | A2 | 6/2008 |
| WO | WO 2008/127743 | A2 | 10/2008 |
| WO | WO 2009/017695 | A1 | 2/2009 |
| WO | WO-2009017695 | A1 * | 2/2009 ............ C12M 23/16 |
| WO | WO 2012/158631 | A2 | 11/2012 |
| WO | WO 2014/151888 | A1 | 9/2014 |
| WO | WO 2015/148842 | A1 | 10/2015 |

OTHER PUBLICATIONS

U.S. Office Action dated Nov. 24, 2014 issued in U.S. Appl. No. 12/667,594.
U.S. Final Office Action dated Jun. 9, 2015 issued in U.S. Appl. No. 12/667,594.
U.S. Office Action dated Jul. 20, 2016 issued in U.S. Appl. No. 12/667,594.
U.S. Final Office Action dated Mar. 17, 2017 issued in U.S. Appl. No. 12/667,594.
U.S. Requirement for Restriction/Election dated May 11, 2016 issued in U.S. Appl. No. 14/117,543.
U.S. Office Action dated Oct. 26, 2016 issued in U.S. Appl. No. 14/117,543.
U.S. Requirement for Restriction/Election dated Dec. 30, 2016 issued in U.S. Appl. No. 14/771,478.
U.S. Office Action dated Mar. 22, 2017 issued in U.S. Appl. No. 14/771,478.
PCT International Search Report and Written Opinion dated Dec. 22, 2008 issued in PCT/US2008/009090.
PCT International Preliminary Report on Patentability dated Jan. 26, 2010 issued in PCT/US2008/009090.
PCT International Search Report and Written Opinion dated Nov. 1, 2012 issued in PCT/US2012/037810.
PCT International Preliminary Report on Patentability dated Nov. 19, 2013 issued in PCT/US2012/037810.
Australian Patent Examination Report No. 1 dated Jun. 26, 2016 issued in AU 2012255988.
Chinese Office Action dated Sep. 10, 2014 issued in CN 201280034358.5.
Chinese Office Action [description in English] dated Nov. 30, 2016 issued in CN 201510509151.4.
European Extended Search Report dated Nov. 10, 2014 issued in EP 12 785 188.9.
European Office Action dated Jun. 14, 2016 issued in EP 12 785 188.9.
Japanese Office Action (Notice of Reasons for Rejection) dated Jan. 18, 2016 issued in JP 2014-510543.
Japanese Second Office Action (Notice of Reasons for Rejection) dated Sep. 16, 2016 issued in JP 2014-510543.
PCT International Search Report and Written Opinion dated Jul. 25, 2014 issued in PCT/US2014/026618.
PCT Corrected Written Opinion dated Jul. 29, 2014 issued in PCT/US2014/026618.
PCT International Preliminary Report on Patentability dated Sep. 24, 2015 issued in PCT/US2014/026618.
European Extended Search Report dated Sep. 23, 2016 issued in EP 14 76 8087.0.
PCT International Search Report and Written Opinion dated Jun. 25, 2015 issued in PCT/US2015/022813.
PCT International Preliminary Report on Patentability dated Oct. 13, 2016 issued in PCT/US2015/022813.
Boudes et al. (2008) "Single-cell electroporation of adult sensory neurons for gene screening with RNA interference mechanism," *J. Neurosci. Methods*, 170:204-211.
Cao et al. (2007) "Plasmon-Assisted Local Temperature Control to Pattern Individual Semiconductor Nanowires and Carbon Nanotubes" *Nano Lett*. 7(11):3523-3527.
Chu et al. (1987) "Electroporation for the efficient transfection of mammalian cells with DNA," *Nucleic Acids Res.*, 15(3):1311-1326.
Clark et al. (2006) "Optoinjection for efficient targeted delivery of a broad range of compounds and macromolecules into diverse cell types," *J. Biomed. Opt.*, 11(1):014034(1-8).
Enders et al. (2006) "Reversible adsorption of Au nanoparticles on $SiO_2$/Si: An in situ ATR-IR study," *Surface Science*, 600(6):L71-L75, [retrieved on Nov. 7,2008 from the Internet: http://www.sciencedirect.com/science?_ob=ArticleURL&_udi=B6TVX-4J5T4WS-7&_user=10&_rdoc=1&_fmt=&_orig=search&_sort=d&view=c&_acct=C000050221&_version=1&_urlVersion=0&_userid=10&md5=2e06d566ab4cc63face36f61c56446b5] Abstract only, 2pp.
Han et al. (2008) "High-efficiency DNA injection into a single human mesenchymal stem cell using a nanoneedle and atomic force microscopy," *J. Nanomed. Nanotechnol. Biol. Med.*, 4(3):215-225.
Heinemann et al, (Mar. 2013) "Gold Nanoparticle Mediated Laser Transfection for Efficient siRNA Mediated Gene Knock Down," *PLOS One*, 8(3):e58604, pp. 1-9.
Hellman et al. (2008) "Biophysical Response to Pulsed Laser Microbeam-Induced Cell Lysis and Molecular Delivery," *J. Biophoton.*, 1(1):24-35.

(56) References Cited

OTHER PUBLICATIONS

Hirst et al. (2005) "Microchannel Systems in Titanium and Silicon for Structural and Mechanical Studies of Aligned Protein Self-Assemblies," *Langmuir*, 21(9):3910-3914.

Hurtig et al. (2008) "Injection and transport of bacteria in nanotube-vesicle networks," *Soft Matter*, 4: 1515-1520.

Jain et al. (2007) "Au nanoparticles target cancer," *Nano Today*, 2(1):18-29.

Kitamura et al. (2008) "Targeted patch-clamp recordings and single-cell electroporation of unlabeled neurons in vivo," *Nat. Methods*, 5(1):61-67.

Kotaidis et al. (2006) "Excitation of nanoscale vapor bubbles at the surface of gold nanoparticles in water," *The Journal of Chemical Physics*, 124:184702(1-7).

Laffafian et al. (1998) "Lipid-assisted microinjection: introducing material into the cytosol and membranes of small cells," *Biophys. J.*, 75:2558-2563.

Lapotko et al. (2006) "Selective laser nano-thermolysis of human leukemia cells with microbubbles generated around clusters of gold nanoparticles," *Laser Surg. Med.*, 38:631-642.

Lee et al. (2009) "Remote Optical Switch for Localized and Selective Control of Gene Interference," *Nano Lett.*, 9(2):562-570.

Lin et al. (Jun. 21-25, 2015) "Shape Anisotropic Magnetic Particles for High Throughput and High Efficiecy Intracelluar Delivery of Functional Macromolecules," *IEEE, Transducers 2015, 18th International Conference on Solid-State Sensors, Actuators and Microsystems (Transducers)*, Anchorage, Alaska, USA, pp. 880-883.

Link et al (1999) "Spectral Properties and Relaxation Dynamics of Surface Plasmon Electronic Oscillations in Gold and Silver Nanodots and Nanorods," *J. Phys. Chem. B*, 103(40):8410-8426.

Liu et al. (2005) "Optofluidic control using photothermal nanoparticles," *Nat. Mater.*, 5:27-32.

Lokhandwalla et al. (2001) "Mechanical haemolysis in shock wave lithotripsy (SWL ): I. Analysis of cell deformation due to SWL flow-fields," *Phys. Med. Biol.*, 46:413-437.

Lukianova-Hleb et al. (2010) "Plasmonic Nanobubbles as Transient Vapor Nanobubbles Generated around Plasmonic Nanoparticles," *ACS Nano*, 4(4):2109-2123.

Marmottant et al. (2003) "Controlled vesicle deformation and lysis by single oscillating bubbles," *Nature*, 423:153-156.

Mitragotri (2005) "Innovation—Healing sound: the use of ultrasound in drug delivery and other therapeutic applications," *Nat. Rev. Drug Discovery*, 4(3):255-260.

Parker et al. (Jul. 13, 2010) "Bulk Titanium Microfluidic Networks for Protein Self-Assembly Studies," [Retrieved on Oct. 23, 2014 from the Internet at URL:http://www.engineering.ucsb.edu/memsucsb/Research/publications/parker_ microtas05.pdf], 4 pp.

Pitsillides et al. (2003) "Selective cell targeting with light-absorbing microparticles and nanoparticles," *Biophys. J.*, 84(6):4023-4032.

Prodan et al. (2003) "A Hybridization Model for the Plasmon Response of Complex Nanostructures," *Science*, 302:419-422.

Qiu et al. (2009) "Microchip CE analysis of amino acids on a titanium dioxide nanoparticles-coated PDMS microfluidic device with in-channel indirect amperometric detection," *Electrophoresis*, 30(19):3472-3479.

Skirtach et al. (2005) "The Role of Metal Nanoparticles in Remote Release of Encapsulated Materials," *Nano Lett.*, 5(7):1371-1377.

Stevenson et al. (2006) "Femtosecond optical transfection of cells:viability and efficiency," *Opt. Express*, 14(16):7125-7133.

Suzuki et al. (2010) "A Cell Array Fabricated by Assembly-Free Multidirectional Photolithography," *Journal of Japan Institute of Electronics Packaging*, 13(3):194-199.

Tirlapur et al. (2002) "Cell biology: Targeted transfection by femtosecond laser," *Nature*, 418:290-291.

Vogel et al. (2005) "Mechanisms of femtosecond laser nanosurgery of cells and tissues," *Appl. Phys. B: Laser Opt.*, 81(8):1015-1047.

Waje et al. (2005) "Deposition of platinum nanoparticles on organic functionalized carbon nanotubes grown in situ on carbon paper for fuel cells," *Nanotechnology*, 16:S395-S400.

Wu et al. (Jul. 21, 2008) "Light Image Patterned Molecular Delivery into Live Cells Using Gold Particle Coated Substrate," *IEEE/LEOS Summer Topical Meetings, 2008 Digest of the IEEE*, Piscataway, NJ, USA, pp. 195-196.

Wu et al. (Feb. 7, 2010) "Molecular Delivery Into Live Cells Using Gold Nanoparticle Arrays Fabricated by Polymer Mold Guided Near-Field Photothermal Annealing," *Proceedings of ASME 2010 First Global Congress on NanoEngineering for Medicine and Biology*, Houston Texas, USA, pp. 121-122.

Wu et al. (2010) "Image patterned molecular delivery into live cells using gold particle coated substrates," *Opt. Express*, 18(2):938-946.

Wu et al. (2010) "Photothermal nanoblade for patterned cell membrane cutting," *Optics Express*, 18(22):23153-23160.

Wu et al. (2011) "Photothermal nanoblade for Large Cargo Delivery into Mammalian Cells," *Anal. Chem.*, 83(4):1321-1327.

Wu et al. (May 1, 2015) "Massively parallel delivery of large cargo into mammalian cells with light pulses," *HHS Public Access Author Manuscript*, 12(5):439-444 and Supplementary information (Apr. 6, 2015) 2pp.

Xia et al. (2011) "Gold Nanocages: From Synthesis to Theranostic Applications," *Acc. Chem. Res.*, 44(10): 914-924.

Yue et al. (2010) "Study of transportation of atrazine and paraquat through nanochannels," *Journal of Membrane Science*, 3556:117-122.

Zhang, Y. (2007) "Microinjection technique and protocol to single cells," *Nat. Protoc.* published online Nov. 2, 2007 [retrieved on May 13, 2011 at 3:04 PM from the Internet at http://www.natureprotocols.com/2007/11/02/microinjection_technique_and_p.php], pp. 1-11.

Zhao et al. (2009) "Wafer level bulk titanium ICP etching using SU8 as an etching mask," *J. Micromech. Microeng.*, 19(9):95006, 10pp.

Australian Patent Examination Report No. 2 dated Jun. 13, 2017 issued in AU 2012255988.

Chinese Second Office Action [No Translation Available] dated Oct. 17, 2016 issued in CN 201510509151.4.

European Office Action dated Jul. 12, 2017 issued in EP 12 785 188.9.

European Office Action dated Sep. 4, 2017 issued in EP 14 76 8087.0.

Menon and Martin (1995) "Fabrication and Evaluation of Nanoelectrode Ensembles," *Anal. Chem.*, 67(13): 1920-1928.

U.S. Office Action dated May 15, 2018 issued in U.S. Appl. No. 12/667,594.

U.S. Final Office Action dated Dec. 26, 2017 issued in U.S. Appl. No. 14/771,478.

U.S. Office Action dated Jan. 30, 2018 issued in U.S. Appl. No. 15/129,387.

Canadian Office Action dated Mar. 12, 2018 issued in CA 2,873,204.

European Office Action dated Feb. 13, 2018 issued in EP 12 785 188.9.

Japanese Office Action (Notice of Reasons for Rejection) dated Jun. 4, 2018 issued in JP 2017-093726.

Korean Office Action dated Apr. 18, 2018 issued in KR 10-2013-7033131.

Chinese Office Action dated Apr. 25, 2018 issued in CN 201480015382.3.

European Second Office Action dated May 22, 2018 issued in EP 14 76 8087.0.

Japanese Office Action dated Mar. 5, 2018 issued in JP 2016-502195.

European Partial Supplementary Search Report dated Nov. 7, 2017 issued in EP 15769138.7.

European Extended Search Report dated Feb. 9, 2018 issued in EP 15769138.7.

Adar (2017) "Raman Polarization Measurements: Keeping Track of the Instrumental Components" *Spectroscopy*, 32(2): 14-22.

Shi et al. (2010) "Pressure Regulated Biomolecule Injection Into NIH 3T3 Cells Through Integrated Nano/Mesopores", *14th International Conference on Miniaturized Systems for Chemistry and Life Sciences* Oct. 3-7, 2010, Groningen, The Netherlands, pp. 491-493, Retrieved from the Internet: URL:http://www.rsc.orgjbinariesjlocj2010/pdfs/Papers/171 0548.pdf [retrieved on Oct. 24, 2017].

(56) References Cited

OTHER PUBLICATIONS

U.S. Office Action dated Sep. 28, 2018 issued in U.S. Appl. No. 14/771,478.
U.S. Final Office Action dated Oct. 17, 2018 issued in U.S. Appl. No. 15/129,387.
Israeli Office Action dated Oct. 25, 2018 issued in IL 241150.
Bruening and Adusumilli, (2011) "Polyelectrolyte Multilayer Films and Membrane Functionalization," *Material Matters*, 6(3): 1-6.
Madeira, et al. (2010) "Nonviral Gene Delivery to Mesenchymal Stem Cells Using Cationic Liposomes for Gene and Cell Therapy," *Journal of Biomedicine and Biotechnology*, vol. 2010, Article ID 73539, pp. 1-12.
Shvedov et al. (2009) "Optical guiding of absorbing nanoclusters in air," *Optics Express*, 17(7):5743-5757.

\* cited by examiner

Sample A

Sample C

1. Spin coat 1st layer SU-8 photoresist.

2. Pattern 1st layer SU-8 photoresist. (100 μm thick)

3. Spin coat and pattern 2nd layer SU-8 photoresist. (4 μm thick)

4. Develop both layers of SU-8.

5. Deposit titanium.

6. Dry etch top layer titanium.

PHOTOTHERMAL SUBSTRATES FOR SELECTIVE TRANSFECTION OF CELLS

CROSS-REFERENCE TO RELATED APPLICATIONS

This application is a continuation of U.S. Ser. No. 14/117,543, filed Oct. 27, 2014, which is a 371 National Phase of PCT/US2012/037810, filed May 14, 2012, which claims benefit of and priority to U.S. Ser. No. 61/486,114, filed May 13, 2011, all of which are incorporated herein by reference in their entirety for all purposes.

STATEMENT AS TO RIGHTS TO INVENTIONS MADE UNDER FEDERALLY SPONSORED RESEARCH AND DEVELOPMENT

[Not Applicable]

BACKGROUND OF THE INVENTION

Transferring cargo into mammalian cells over a wide range of 1 sizes, including proteins, DNA, RNA, chromosomes, nuclei, and inanimate particles, such as quantum dots, surface-enhanced Raman scattering (SERS) particles, and microbeads, is highly desirable in many fields of biology. Delivery methods, such as endocytosis, can entrap cargo in an endosome, where the low pH microenvironment and lytic enzymes often lead to cargo degradation (Luo and Saltzman (2000) *Nat. Biotechnol.* 18: 33-37). Viral and chemical delivery methods package the cargo inside a virus or form chemical complexes that enhance uptake (Naldini et al. (1996) *Science,* 272: 263-267; Feigner et al. (1987) *Proc. Natl. Acad. Sci. USA,* 84: 7413-7417). However, toxicity, cell-type specific uptake, and more importantly limited cargo packing capacity impose a significant constraint on cargo size and transferable cell types (Luo and Saltzman, supra.).

Physical transfer methods include electroporation (Chu, et al. (1987) *Nucleic Acids Res.* 15: 1311-1326) and sonoporation (Mitragotri (2005) *Nat. Rev. Drug Discovery,* 4: 255-260), which produce randomly distributed nanoscale pores, and optoporation (Tirlapur and Konig (2002) *Nature,* 418: 290-291; Vogel, et al. (2005) *Appl. Phys. B: Laser Opt.,* 81: 1015-1047; Clark et al. (2006) *J. Biomed. Opt.,* 11: 014034), which generates pores on the cell membrane at the laser focal point. Through these pores, small cargo is delivered into cells by thermal diffusion or by an electric field. Delivery of large cargo with these methods has low efficiency due to the slow speed of cargo diffusion and decreasing cell viability with increasing pore size (Stevenson et al. (2006) *Opt. Express,* 14: 7125-7133). Microcapillary injection (King (2004) *Methods in Molecular Biology* 245: *Gene Delivery to Mammalian Cells* 1; Humana Press Inc.: Totowa, N.J.) uses a sharp lass tip to mechanically penetrate a cell membrane for delivery. However, mechanical trauma from membrane penetration limits the typical pipet tip to 0.5 um in diameter in order to maintain cell viability (Han et al. (2998) *J. Nanomed. Nanotechnol. Biol. Med.,* 4: 215-225).

Cargo larger than the pipet tip cannot be injected due to pipet clogging and cargo shearing. Electroinjection, which combines electroporation with microcapillary injection, has demonstrated small molecule delivery, such as RNA and plasmid DNA, into live cells (Boudes et al. (208) *J. Neurosci. Meth.,* 170: 204-211; Kitamura et al. (2008) *Nat. Meth.,* 5: 61-67) and bacteria delivery into artificial lipid vesicles (Hurtig and Orwar (2008) *Soft Matter,* 4: 1515-1520) by weakening the contacting cell membrane with an electric field, followed by gentle mechanical penetration into the cell. Alternatively, a simple lipid assisted microinjection (SLAM) technique (Laffafian and Hallett (1998) *Biophys. J.,* 75: 2558-2563) incorporates synthetic lipid molecules at the tip of a glass microcapillary. Contact of the SLAM micropipette with a cell membrane allowed the lipid molecules to fuse with the cell membrane to form a continuous and temporary pathway for cargo delivery. This method avoids the zigzag stabbing motion of the micropipette tip through the cell membrane. However, the lipohilic interactions with cargo and cell membrane could produce unwanted biological effects in the cell as well as with the delivery cargo, limiting this method to specific cell types and cargo contents.

SUMMARY OF THE INVENTION

In certain embodiments the present invention provides a cell surgery tool that can achieve highly local penetration of a cell with significantly reduced damage or stress to the cell. In certain embodiments a cell microsurgery tool is provided where the tool comprises a microcapillary (e.g., micropipette) having at and/or near the tip a metal film or a plurality of nanoparticles that can be heated by application of electromagnetic energy.

In certain embodiments a cell microsurgery tool is provided. Typically, the tool comprises a microcapillary having at and/or near the tip a metal film or a plurality of nanoparticles that can be heated by application of electromagnetic energy. In certain embodiments the microcapillary comprises a hollow bore. In certain embodiments the tip of the microcapillary ranges in diameter from about 0.01 µm, 0.05 µm, 0.1 µm, or 0.5 µm to about 1 µm, 3 µm, 5 µm, 8 µm, or 10 µm. In certain embodiments the micropipette has an OD ranging from about 0.5 to about 2 µm or 3 µm. In various embodiments the nanoparticles range in size from about 50 nm to about 500 nm. In various embodiments the nanoparticles range in size from about 10 nm to about 500 nm. In various embodiments the nanoparticles are selected from the group consisting of a nanobead, nanowire, a nanotube, a nanodot, a nanocone, and a quantum dot. In various embodiments the metal film or nanoparticles comprise a noble metal, a noble metal alloy, a noble metal nitride, and/or a noble metal oxide. In various embodiments the metal film or nanoparticles comprise a transition metal, a transition metal alloy, a transition metal nitride, and/or a transition metal oxide. In various embodiments the metal film or nanoparticles comprises a magnetic, paramagnetic, or superparamagnetic material. In various embodiments the microcapillary comprises a material selected from the group consisting of glass, a mineral, a ceramic, and a plastic. In certain embodiments the microcapillary comprises a glass microcapillary having nanoparticles near the tip. In certain embodiments the microcapillary comprises a glass microcapillary having gold nanoparticles near the tip. In certain embodiments the microcapillary comprises a glass microcapillary where the nanoparticles are predominantly located within 100 µm of the tip of the microcapillary.

Also provided is a method of performing micromanipulations on a cell. The methods typically involves contacting the cell with a microsurgery tool as described herein; and applying electromagnetic energy to the tool whereby the temperature of the metal film or metal nanoparticles is increased thereby facilitating penetration of the tool into or through the membrane of the cell. In certain embodiments the applying electromagnetic energy comprises applying light to heat the metal film or the nanoparticles. In certain embodiments the applying electromagnetic energy comprises applying a laser beam to heat the metal film or the nanoparticles. While laser heating is generally preferred, other electromagnetic sources are contemplated. Accordingly, in certain embodiments the applying electromagnetic energy comprises applying a magnetic field to heat the metal film or the nanoparticles. In certain embodiments the applying electromagnetic energy comprises applying an electric field to heat the metal film or the nanoparticles. In various embodiments the temperature of the metal film or metal nanoparticles is increased at least 100, 150, 200, 250, 300, or 350 degrees Celsius above-ambient. In certain embodiments the method further comprises injecting a material into the cell through the microcapillary tube. In certain embodiments the method further comprises removing a material from the cell through the microcapillary tube. In certain embodiments the microcapillary comprises a hollow bore. In certain embodiments the tip of the microcapillary ranges in diameter from about 0.1 μm to about 5um. In certain embodiments the nanoparticles range in size from about 5 nm to about 500 nm and/or from about 10 nm to about 400 nm. In certain embodiments the nanoparticles are selected from the group consisting of a nanowire, a nanotube, a nanodot, a nanocone, and a quantum dot. In various embodiments the metal film or nanoparticles comprise a noble metal, a noble metal alloy, a noble metal nitride, and a noble metal oxide. In various embodiments the metal film or nanoparticles comprise a transition metal, a transition metal alloy, a transition metal nitride, and a transition metal oxide. In various embodiments the metal film or nanoparticles comprise a magnetic, paramagnetic, or superparamagnetic material. In certain embodiments the microcapillary comprises a material selected from the group consisting of glass, a mineral (e.g., quartz), a ceramic, and a plastic (e.g., polypropynene, polyethylene, polystyrene, DELRIN®, TEFLON®, etc.). In certain embodiments the microcapillary comprises a glass or quartz microcapillary having nanoparticles near the tip. In certain embodiments the microcapillary comprises a glass microcapillary having gold nanoparticles near the tip. In certain embodiments the microcapillary comprises a glass microcapillary where the nanoparticles are predominantly located within 100 μm of the tip of the microcapillary.

Also provided is a system for performing microsurgery on a cell, the system comprising a microsurgery tool as described herein, and a micromanipulator (micropositioner) for positioning the microsurgery tool. In certain embodiments the system further comprises a microscope for visualizing a cell manipulated by the microsurgery tool. In certain embodiments the system further comprises a pump for delivering or removing a reagent (e.g., a molecule, organelle, or fluid) using the microsurgery tool. In certain embodiments the system further comprises an electromagnetic energy source (e.g., a laser) for exciting the particles/nanoparticles and/or thin film on the microsurgery tool. In various embodiments the electromagnetic energy source is selected from the group consisting of a magnetic field generator, a laser, an RF field generator, and the like.

In various embodiments this invention provides methods of preparing a tool for microsurgery on a cell. The methods typically involve attaching to a microcapillary tube a plurality of nanoparticles at or near the tip of the microcapillary tube thereby providing a device that can be locally heated by application of electromagnetic energy to the nanoparticles. In certain embodiments the attaching comprises adsorbing the nanoparticles to the microcapillary. In certain embodiments the attaching comprises fabricating the nanoparticles in situ on the microcapillary. In certain embodiments the attaching comprises chemically coupling the nanoparticles to the microcapillary.

In certain embodiments the single-cell surgery tools of this invention include atomic force measurement (AFM) tips. For example, a nanoparticle can be integrated with an AFM tip for cell surgery applications. This nanoparticle integrated AFM tip can cut any desire shape on a cell membrane by scanning the tip and laser pulsing it.

In certain other embodiments the tools of this invention expressly exclude atomic force measurement (AFM) tips.

Also provided are devices for delivering an agent into a cell (transfection devices). In various embodiments the devices comprise a surface (e.g., a transfection substrate) bearing particles and/or nanoparticles and/or a film (e.g., a thin film) where the particles/nanoparticles and/or thin film comprises a material that heats up when exposed to (e.g., irradiated by) an energy source (e.g., electromagnetic radiation such as a laser). Cells can be disposed on or near the surface, and when the particles/nanoparticles and/or thin film is heated up, openings are formed in the cell (e.g., the cell membrane is permeabilized) permitting the introduction or removal of various reagents into or from the cell. In certain embodiments the surface comprises the surface of a vessel (e.g., a cell culture vessel, a microtiter plate, a chamber in a microfluidic device, and the like. In certain embodiments the surface comprises a wall and/or floor of a well in a microtiter plate, a silicon or glass wafer, a microscope slide, a cell culture vessel, or a chamber or channel in a microfluidic device. In certain embodiments the surface comprises a surface of a chamber configured to contain cells and disposed for viewing with a microscope. In certain embodiments the surface comprises a surface of a chamber configured to replace a stage on a microscope (e.g., an inverted microscope). In certain embodiments the chamber has an open top, while in other embodiments, the top of the chamber is closed. In certain embodiments the surface comprises a material selected from the group consisting of a glass, a mineral, and a plastic. In certain embodiments the surface comprises a material selected from Group II materials, Group III materials, Group IV materials, Group V materials, and/or Group VI materials. In certain embodiments the surface comprises a Group IV material (e.g., silicon, germanium, etc.).

In various embodiments the surface comprises one or more orifices. In certain embodiments the nanoparticles and/or thin film is deposited on a surface of the orifice or near the orifice. In certain embodiments the surface comprises at least two orifices, or at least 3 orifices, or at least 4 orifices, or at least 5 orifices, or at least 8 orifices, or at least 10 orifices, or at least 15 orifices, or at least 20 orifices, or at least 25 orifices, or at least 30 orifices, or at least 40 orifices, or at least 50 orifices, or at least 75 orifices, or at least 100 orifices, or at least 200 orifices, or at least 300 orifices, or at least 500 orifices. In certain embodiments said orifices are all located within an area of said surface of about 2 cm$^2$ or less, or about 1 cm$^2$ or less, or within about 0.5 cm$^2$ or less, or within about 0.1 cm$^2$ or less. In certain embodiments the nanoparticles and/or thin film are disposed within about 100 μm, or within about 50 μm, or within about 25 μm, or within about 20 μm, or within about 15 μm, or within about 10 μm, or within about 5 μm of said orifice(s). In certain embodiments the particles/nanoparticles and/or thin film is deposited on a surface of a plurality of the orifices and/or near a plurality of the orifices. In certain embodiments the particles/nanoparticles and/or thin film is deposited on a surface of a majority of the orifices and/or near a majority of the orifices. In certain embodiments the particles/nanoparticles and/or thin film is deposited on a surface of substantially all of the orifices and/or near substantially all of the orifices. In certain embodiments the nanoparticles and/or a thin film are deposited on a wall and/or all around the lip of the orifice(s). In certain embodiments the nanoparticles and/or a thin film are preferentially on one region of a wall or lip of the orifice(s). In certain embodiments the nanoparticles and/or a thin film are deposited on the face of the surface and/or on the lip of an orifice on the same side on which cells are disposed. In certain embodiments the nanoparticles and/or a thin film are deposited on the face of the surface and/or on the lip of an orifice opposite the side on which cells are disposed. In certain embodiments the nanoparticles and/or thin film comprise a thin film. In certain embodiments the nanoparticles and/or thin film comprise nanoparticles and the nanoparticles range in size from about 5 nm to about 500 nm. In certain embodiments the nanoparticle range in size from about 2 nm, or about 5 nm, or about 10 nm, or about 15 nm, or about 20 nm to about 400 nm, or to about 300 nm, or to about 250 nm, or to about 200 nm, or to about 150 nm, or to about 100 nm, or to about 75 nm, or to about 50 nm. In certain embodiments the nanoparticles are selected from the group consisting of a nanobead or nanosphere, a nanowire, a nanotube, a nanodot, a nanocone, and a quantum dot. In certain embodiments the nanoparticles and/or thin film comprise a material selected from the group consisting of a semiconductor, a metal, a metal alloy, a metal nitride, and a metal oxide. In certain embodiments the nanoparticles and/or thin film comprise a material selected from the group consisting of a transition metal, a transition metal alloy, a transition metal nitride, and a transition metal oxide. In certain embodiments the nanoparticles and/or thin film comprise a material selected from the group consisting of gold, titanium (Ti), TiN, TiCn, and TiAlN. In certain embodiments the nanoparticle and/or thin film comprise a Group IV material (e.g., silicon, germanium, etc.) doped with a Group III material or a Group V material. In certain embodiments the nanoparticle and/or thin film comprise silicon or germanium doped with a material selected from the group consisting of boron, arsenic, phosphorous, or gallium. In certain embodiments one or more of the orifices are in fluid communication with a chamber containing a reagent to be delivered into a cell. In certain embodiments the device comprises a microchannel and one or more of the orifices are in fluid communication with the microchannel. In certain embodiments the device comprises a plurality of microchannels. In certain embodiments different microchannels are in fluid communication with different orifices. In certain embodiments the device comprises a manifold and/or valves to deliver fluids to different microchannels. In certain embodiments the microchannel(s) contain a reagent to be delivered into said cell. In certain embodiments the reagent is selected from the group consisting of a nucleic acids, a ribozyme, a protein or peptide, an enzyme, an antibody, an organelle, a chromosome, a pathogen, and a microparticle or nanoparticle. In certain embodiments the microchannel(s) (or the chamber(s)) are pressurized, under control of a pump, fed by a gravity feed, or electrokinetically pumped. In certain embodiments the device further comprises a controller that monitors and/or controls flow in said microchannel and controls timing and, optionally, location of the illumination of said surface. In certain embodiments the device is configured to replace the stage on an inverted microscope. In various embodiments one or more cells are disposed on the surface and in certain embodiments; the cell(s) are disposed on or adjacent to an orifice in the substrate. In certain embodiments the cell is a mammalian cell (e.g., a human cell, a non-human mammalian cell). In certain embodiments the cell is a stem cell (e.g., a fetal stem cell, a cord blood stem cell, an adult stem cell, an induced pluripotent stem cell (IPSC), etc.).

In certain embodiments systems are provided for selectively creating an opening into a cell or a group of cells. In certain embodiments the system is one for selectively delivering an agent into a cell. The system typically comprises a device comprising a transfection substrate (e.g., as described above) and a source of electromagnetic energy capable of heating the nanoparticles or thin film. In certain embodiments the source of electromagnetic energy is a laser or a non-coherent light source. In certain embodiments the source of electromagnetic energy is a laser. In certain embodiments the system comprises a lens system, a mirror system, or a mask, and/or a positioning system to directing the electromagnetic energy to a specific region of the surface. In certain embodiments the system comprises a controller that controls the timing and/or pattern of illumination by the source of electromagnetic radiation.

In certain embodiments methods are provided for selectively creating an opening into a cell or a group of cells. In certain embodiments the methods can be used to selectively delivering a reagent (or multiple agents) into a cell. In various embodiments the methods utilize the transfection substrates and/or systems (e.g., as described above). Accordingly in certain embodiments, a method of delivering a reagent into a cell is provided. The method comprises providing cells on a device comprising a transfection substrate (e.g., as described above) and/or in a system comprising a device for transfecting cells (e.g., as described above) where the cells are disposed on the surface (transfection substrate); contacting the cells with the reagent; and exposing a region of the surface to electromagnetic radiation thereby inducing heating of the thin film and/or particles where the heating forms bubbles that introduce openings in the membrane of cells in (or near) the heated region resulting in the delivery of the reagent into those cells. In certain embodiments the cells are contacted with the reagent by providing the reagent in a fluid (e.g., buffer, culture medium) surrounding the cells. In certain embodiments the cells are contacted with the reagent by providing the reagent in one or more orifices that are present in the surface. In certain embodiments the cells are contacted with the reagent by providing the reagent in one or more microfluidic channels in fluid communication with the orifices. In certain embodiments different reagents are delivered to different orifices. In certain embodiments the exposing comprises exposing a region of the substrate to a laser pulse or to a non-coherent light source. In certain embodiments the reagent is selected from the group consisting of a nucleic acid, a chromosome, a protein, a label, an organelle, and a small organic molecule.

In certain embodiments methods of performing micromanipulations on a cell are provided that utilize the tip of a microcapillary as a light guide and/or to tune the heat distribution at the tip. In certain embodiments the methods involve contacting the cell with a microsurgery tool, the tool comprising a microcapillary having at and/or near the tip a metal film (coating) or metal nanoparticles that can be heated by application of electromagnetic energy; applying electromagnetic energy to the tool whereby the temperature of the metal film or metal nanoparticles is increased resulting in the formation of an opening in the membrane of the cell, where the contact angle of the microsurgery tool with the cell and/or the polarization of the electromagnetic energy is varied to alter the size and/or shape of the opening introduced into the cell. In certain embodiments the applying electromagnetic energy comprises applying light (e.g. a laser or non-coherent light) to heat the film or the nanoparticles. In certain embodiments the tip of the microsurgery tool is configured to act as a light guide. In certain embodiments the applying electromagnetic energy comprises applying a laser beam to heat the film or the nanoparticles. In certain embodiments the applying electromagnetic energy comprises applying an electric field and/or a magnetic field to heat metal film or the nanoparticles. In certain embodiments, the temperature of the metal film or metal nanoparticles is increased at least 150° C. above-ambient. In certain embodiments the method further comprises injecting a reagent into the cell through the microcapillary tube. In certain embodiments the tip of the microcapillary ranges in diameter from about 0.1 µm to about 5 µm. In certain embodiments the nanoparticles range in size from about 5 nm to about 500 nm. In certain embodiments the metal film or nanoparticles comprise a semiconductor, or a metal selected from the group consisting of a noble metal, a noble metal alloy, a noble metal nitride, and a noble metal oxide. In certain embodiments the metal coating or nanoparticles comprise a transition metal, a transition metal alloy, a transition metal nitride, and a transition metal oxide. In certain embodiments the metal coating or nanoparticles comprise a material selected from the group consisting of gold, titanium (Ti), TiN, TiCn, and TiAlN. In certain embodiments the microcapillary comprises a material selected from the group consisting of glass, a mineral, a ceramic, and a plastic. In certain embodiments the nanoparticles or film comprises a film. In certain embodiments the nanoparticle or film comprises nanoparticles.

Definitions

The term "nanoparticles", as used herein refers to a particle having at least one dimension having an average size equal to or smaller than about 800 nm or 700 nm or 600 nm, or 500 nm, preferably equal to or smaller than about 200 nm or 150 nm, or 100 nm, more preferably equal to or smaller than about 50 or 20 nm, or having a crystallite size of about 10 nm or less, as measured from electron microscope images and/or diffraction peak half widths of standard 2-theta x-ray diffraction scans. In certain embodiments, preferably, the first standard deviation of the size distribution is 60% or less, preferably 40% or less, most preferably 15 to 30% of the average particle size.

The phrase "range in size" with respect to nanoparticle size indicates that the nanoparticles are predominantly within the size range. Thus, for example, in certain embodiments, at least 85%, preferably at least 90%, more preferably at least 95%, and most preferably at least 98%, 99%, or even all of the nanoparticles are within the stated size range.

The term "transition metal" refers to typically refers to any element in the d-block of the periodic table, excluding zinc, cadmium and mercury. This corresponds to groups 3 to 12 on the periodic table.

The terms "microcapillary tube" "microcapillary", and "micropipette" are used interchangeably. A "microcapillary" is a tube that has a tip with a diameter of less than about 50 µm, preferably less than about 25 µm, more preferably less than about 15 µm or 10 µm, and most preferably less than about 5 µm. In certain embodiments the microcapillary has a tip diameter of about 2 µm or less. In certain embodiments the microcapillary can be a solid rod. In certain embodiments the microcapillary can be replaced with a pipette (capillary tube) having a larger tip diameter (e.g., greater than about 200 nm as described herein).

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321, O-methylphophoroamidite linkages (see Eckstein, Oligonucleotides and Analogues: A Practical Approach, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide. Preferred "peptides", "polypeptides", and "proteins" are chains of amino acids whose α carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to peptide mimetics such as amino acids joined by an ether as opposed to an amide bond.

The term "reagent(s)" when used with respect to substances to be delivered into cells include any substance that is to be delivered into (or extracted from) a cell. Such reagents include, but are not limited to nucleic acids (including, for example, vectors and/or expression cassettes, inhibitory RNAs (e.g., siRHA, shRNA, miRNA, etc.), ribozymes, proteins/peptides, enzymes, antibodies, imaging reagents, organelles (e.g., nuclei, mitochondria, nucleolus, lysosome, ribosome, etc.), chromosomes, intracellular pathogens, inanimate particles, such as quantum dots, surface-enhanced, Raman scattering (SERS) particles, microbeads, and the like.

BRIEF DESCRIPTION OF THE DRAWINGS

As illustrated in FIG. 16A, a cell is disposed over one of the orifices in the array and the orifice is in fluid communication with a microchannel. As illustrated, one edge of the orifice is coated with a thin film of, in this case, titanium. The film is heated by use of an energy source (e.g., a pulsed laser). This results in heating of the thin film as illustrated in FIG. 16B. An expanding vapor bubble is formed that results in formation of an opening through the lipid bilayer of the cell. As illustrated in FIG. 16C, deliverable materials pass from the microchannel through the orifice into the cell via passive diffusion or active pumping.

FIGS. 22A and 22B: Scanning electron microscope images of a pulled, Ti-coated micropipette. Inner diameter=1.38±0.1 µm (mean s.d.). Outer diameter=1.88±0.1 µm. Thickness of Ti thin film=102±8 nm. (The arrow points to edge of the glass filament running inside the micropipette.) FIG. 22C: Normalized intensity profiles at the tip of the micropipette under laser excitation ($n_{Ti}$=1.86+2.56i (Lynch and Hunter (1998) Introduction to the data for several metals. In Handbook of Optical Constants of Solids, Vol. III; Academic Press: San Diego, Calif.), $n_{glass}$=1.46, $n_{water}$=1.34, $\lambda$=532 nm, $\theta$=30°). FIG. 22D: Time-averaged optical absorption profiles ($\propto$=$E_{ave}|^2$) in the Ti ring at the micropipette tip.

FIG. 23A: A nanobubble with maximum radius extending to 0.4 μm from the rim of the pipet tip when in contact with the cell membrane. Energy transfer to the contacting membrane reduces the size of nanobubble formation and locally cuts the plasma membrane. FIG. 23B: Fast expansion and collapse dynamics of a vapor nanobubble within 270 ns in free suspension and 170 ns in contact with a HeLa cell membrane. FIG. 23C: Cell viability postphotothermal delivery. The control experiment was performed using a glass-only micropipette in contact with the cell (no piercing through the membrane) and illuminating with a laser pulse at the same fluence (180 mJ/cm²). Cell viability is >90% when cells were subjected to laser pulsing and membrane opening alone (98±11% (mean s.d.)) and in experiments where cells were subjected to laser pulsing and liquid injection (94±4%).

FIG. 25A: Pathway of bacterial uptake following transfer (Wiersinga et al. (2006) *Nat. Rev. Microbial.* 4: 272-282). FIG. 25*b*: GFP-labeled *Burkholderia thailandensis* was transferred into a HeLa cell (average efficiency=46±33% (mean (s.d.)) along with red-fluorescent dextrantetramethylrhodamine. Confocal z-axis scanning showing multiple bacteria inside a red-fluorescent cell. FIG. 25*b*: Multiplication and actin polymerization of transferred mCherry-labeled *B. thailandensis* in HeLa cells.

FIG. 28A illustrates the opening made with a vertical pipette (nanoblade) heated using linearly polarized light. FIG. 28B illustrates the opening made with a vertical pipette (nanoblade) heated using circularly polarized light. FIG. 28C illustrates the opening made with a tilted pipette (nanoblade).

DETAILED DESCRIPTION

Figure 1:
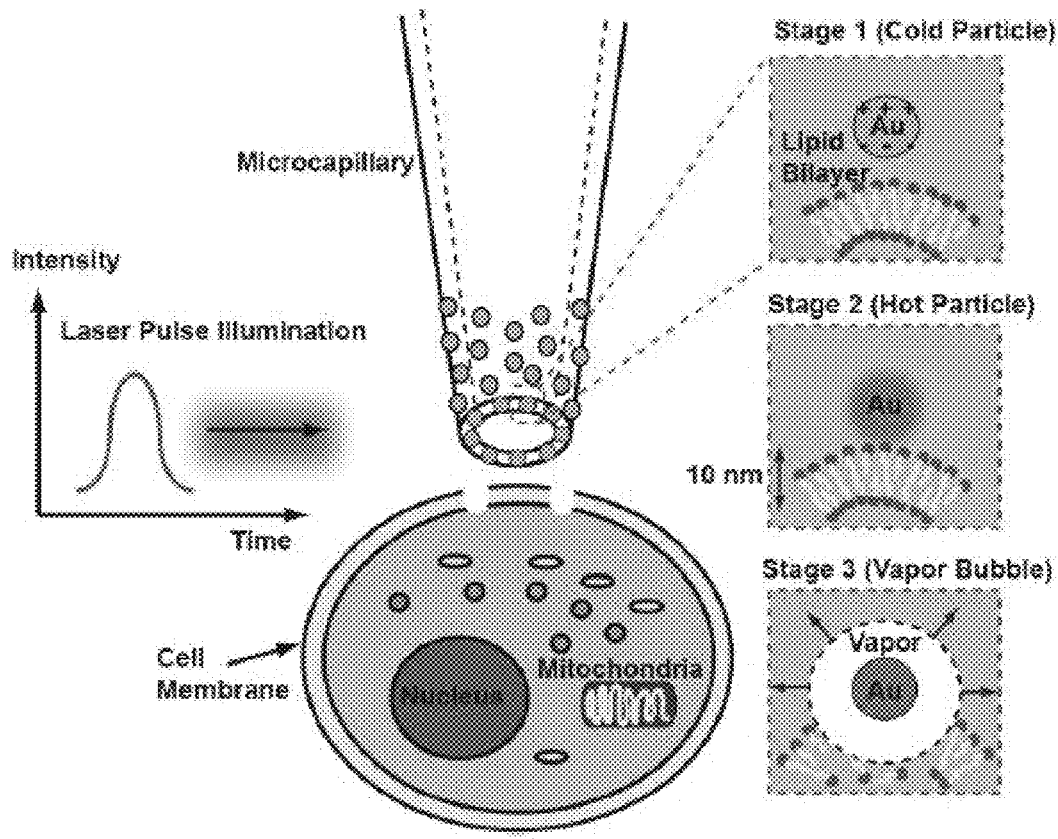
FIG. 1 schematically illustrates one embodiment of the cell-surgery tool.

In certain embodiments this invention pertains to a new tool/device useful for "surgical" procedures on single cells and to substrates for the manipulation of cells and/or the delivery or extraction of reagents from those cells.

Surgical Tool for Operation on Cells.

In various embodiments a "single cell surgical tool" is provided to perform microinjection, microextraction, and/or intracellular manipulations with minimal cell damage. It can be used with any cell bounded by a lipid bilayer (e.g., a eukaryotic cell, more preferably a vertebrate cell, still more preferably a mammalian cell type). In certain embodiments the device can be utilized with cells comprising a cell wall (e.g., plant cells).

In certain illustrative embodiments, the device comprises a microcapillary tube (e.g., micropipettete) comprising "energy absorbent" nanoparticles and/or an "energy absorbent" thin film at or near the tip of the microcapillary. This device achieves precise and controllable nanoscale modification of cells, by excitation/heating (e.g., laser-induced heating) of the metal particles/nanoparticles and/or a metal film (e.g., nanocoating) coated on the micocapillary. Without being bound to a particular theory, it is believed that when brought nearby or in contact with the surface of a cell, this extremely local heating produces precisely-sized holes in the cell membrane (and/or cell wall). This way the micropipette can penetrate the cell membrane with ease without inducing mechanical and biochemical damage associated with current microinjection and extraction techniques. This tool facilitates thus operative procedures on small and mechanically fragile cells with a high rate of success.

Single-cell microinjection is a powerful and versatile technique for introducing exogenous material into cells, for extracting and transferring cellular components between cells, and/or for the introduction of components not normally found within cells, such as probes, detectors, or genetically engineered organelles, genes, proteins and the like. Conventional glass micropipette techniques, such as those used to generate transgenic mice, introduce enormous mechanical and biochemical stresses on the cells and yield low rates of success, particularly for mechanically fragile cells.

Current laser-induced cell ablation procedures eliminate this mechanical stress but require highly focused light and the damage volume is diffraction-limited. In contrast, the cell surgery tool describe herein can achieve manipulations (e.g., ablation) at a nanometer size scale at or near the tip of a capillary micropipette by local heating of particles/nanoparticles and/or a thin film at or near the pipette tip. The particles/nanoparticles and/or thin film are heated using electromagnetic radiation (e.g., a magnetic field, an electric field, an RF field, broad or focused laser pulses, and the like).

In various embodiments the cell surgery methods described herein utilize the photothermal effect of metal particles/nanoparticles and/or a thin metal film. For example, by controlling the geometry (e.g., aspect ratio) and/or composition of the particles and/or the thickness or composition of the film, the material can be "tuned" so that electromagnetic radiation (e.g., laser energy) is strongly absorbed by particles and/or thin film, but not by nearby cells or cellular contents, thereby avoiding cell or genetic damage caused by traditional laser-based methods of manipulating cells. Current laser cell techniques rely on strong absorption of the laser power by cellular contents to create ablation or cavitation effects. Such processes can damage cells and can cause undesired breakdown of cellular constituents or chemical effects that may affect the biology of the cells being manipulated.

In contrast, utilizing the microsurgical tools described herein, the laser, or other source of electromagnetic energy, can be used to heat particles/nanoparticles and/or a thin film localized at the cell membrane by being bound to microcapillary pipettes. Thus, the energy source (e.g., laser) does not substantially damage the cells being manipulated.

Depending on the selection of materials, the nanoparticles and/or thin film can be excited (heated) by application of essentially any electromagnetic radiation. Thus, in various embodiments, heating of the nanoparticles and/or thin film(s) is accomplished by application of a magnetic field, and/or an electric field, and/or an RF field, and/or light (e.g., a laser).

For example, metal particles, nanoparticles, and thin films strongly absorb electromagnetic waves with frequencies close to the surface plasmon frequency, usually in the visible and near-IR range. Particles, nanoparticles, and thin films rapidly heat up, due to the absorbed energy, to generate a superheating phenomenon with evaporation of the surrounding medium. In certain embodiments of the cell surgery tool, individual or multiple nanoparticles are coated onto the tip of a micropipettete, e.g., as shown in FIG. 1. Upon laser pulse excitation, nanometer diameter vapor bubbles are created around the nanoparticles. When brought nearby or in contact with the surface of a cell, this process generates controlled, precisely-sized holes in the cell membrane (and/or cell wall). This way the micropipette can penetrate the cell membrane with ease without inducing mechanical and biochemical damage associated with current microinjection and extraction techniques. The cavitation or "hole punching" process is finished within a few nanoseconds. As a result, the rest of the membrane does not have time to respond and remains mechanically undisturbed. Once the pipette is in place in the cell, the "membrane hole" can be kept open for manipulations with devices, such as fiber optic devices, threaded through the hollow bore of the pipette. In certain embodiments similar effects can be obtained using thin metal film deposited at and/or near the tip of the microcapillary.

In one illustrative mode of operation, the micropipetteis positioned next to the targeted cell by micromanipulators and/or automated (e.g., piezo-driven) stages under a microscope (e.g., an inverted microscope). By pulsing a laser (or other energy source) on the tip of the micropipettete, the pipette eases through the membrane without causing significant cell deformation. Once the pipette is inside the cell, subsequent injection or extraction of molecules and cellular components can be performed, as can live cell intracellular manipulations.

Figure 3:
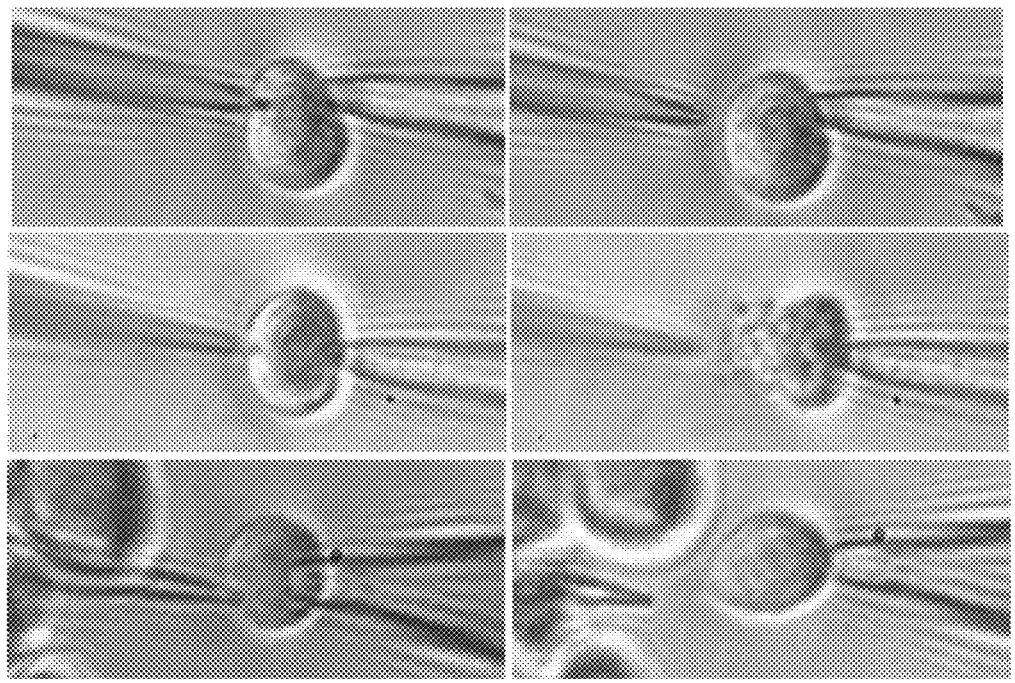
FIG. 3 shows cells before and after laser pulsing. (Top) Glass micropipette(Middle) carbon coated micropipette (Bottom) gold nanoparticles coated micropipettete.

The cell surgery tool can thus be used for performing single-cell microinjection, and/or extraction, and/or intracellular manipulation. Hole punching on adherent cell membranes has been demonstrated, and this is easily extended to cells in suspension, to cells immobilized using optical tweezers, and/or to cells that routinely grow in clusters, colonies, or clumps with the assistance of a standard suction-based holding pipette. Illustrative experimental results are shown in FIG. 3.

Figure 27:
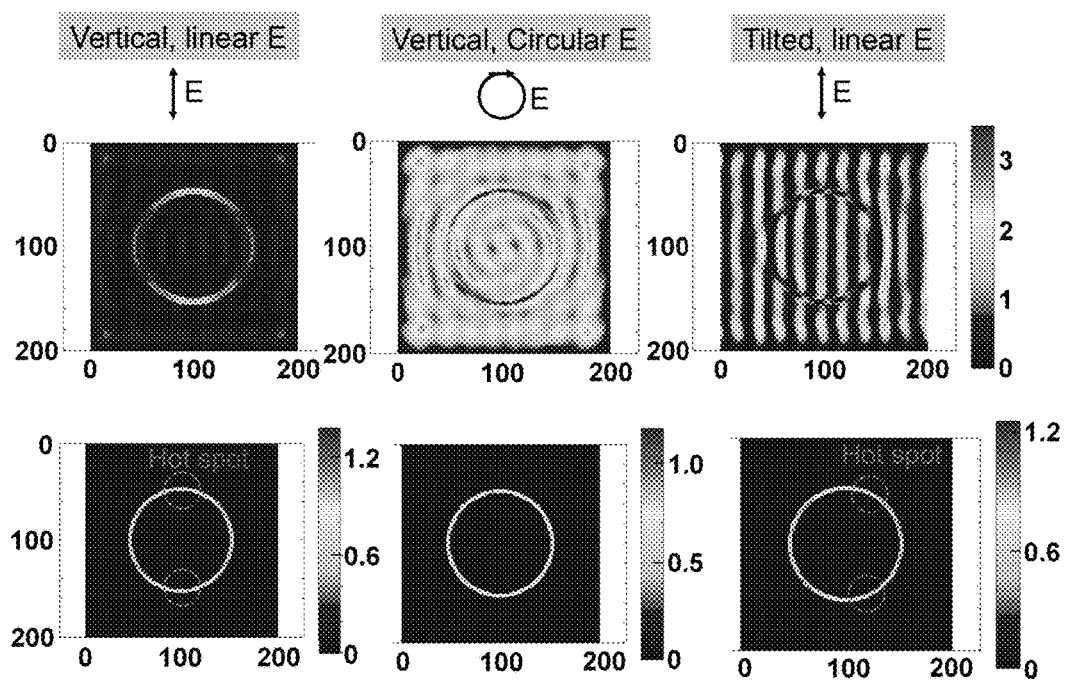
FIG. 27 illustrates the effect of illumination angle and polarization on the thermal distribution at a nanoblade tip. Instantaneous intensity is shown in the top row and time averaged intensity is shown in the bottom row. Left column show a vertically oriented tip with linear polarization. Middle column shows a vertically oriented tip with circular polarization. Right column shows a tilted tip (30°) with linear polarization.
Figure 28A:
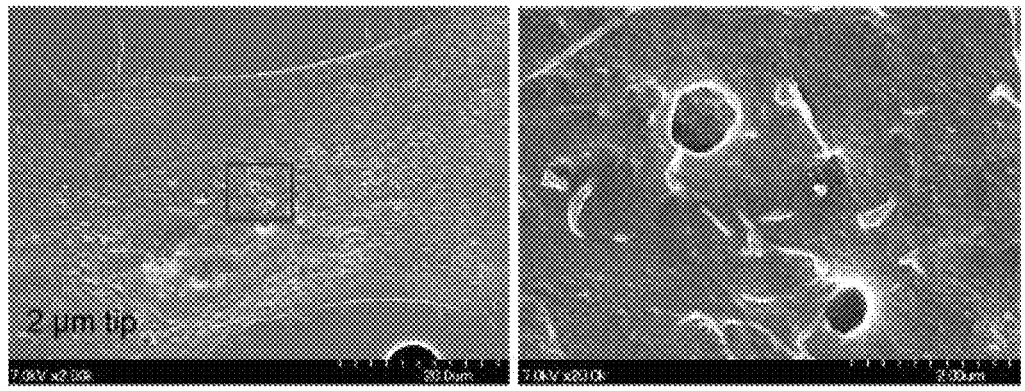
FIGS. 28A-28C illustrate the effect of illumination angle and polarization on opening made into a cell.
Figure 28B:
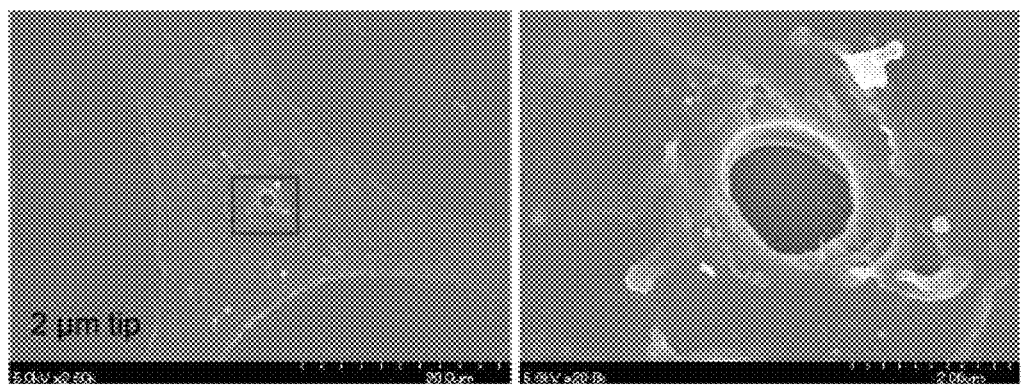
Figure 28C:
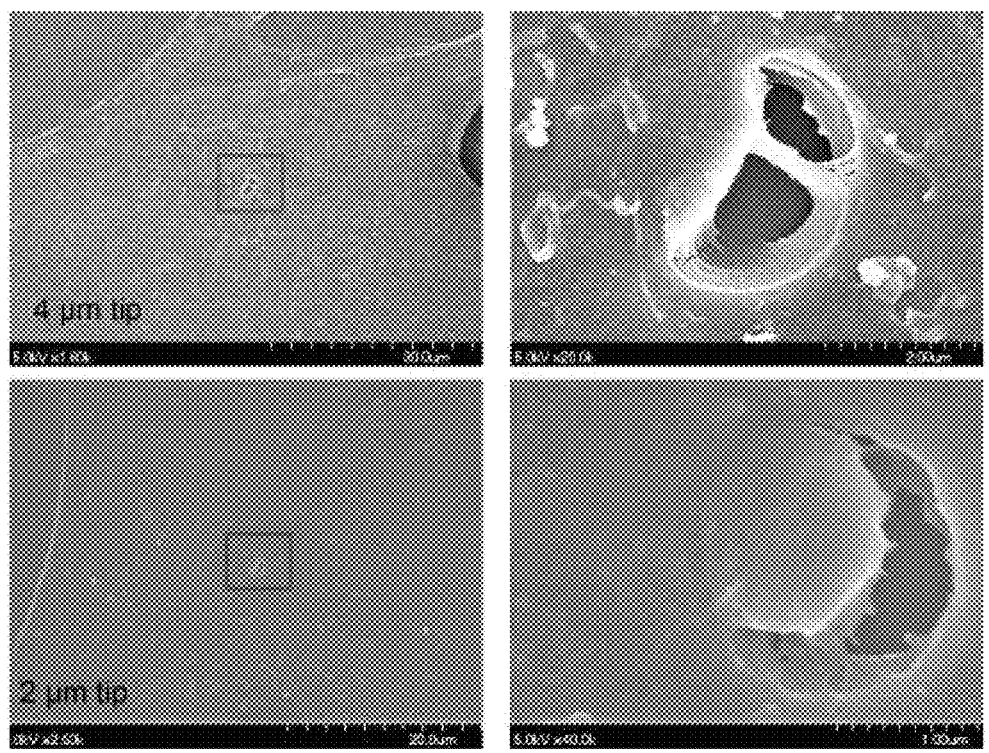

In various embodiments different membrane cutting can be accomplished by varying the angle of the pipette (nanoblade) and/or by varying the laser polarization. For example, as the pipette tilts from 0 (vertical) to 30 degrees, the hot spots on the titanium ring move from being at polar opposite to being closer to each other (see, e.g., FIG. 27). The resulting cut in the membrane is "bat eye" shaped (see, e.g., FIGS. 28A-28C).

Another factor controlling the cutting pattern (mentioned in Optics Express paper) is the pipette tip size. When pipette tip size is reduced to 2 micron, heat can diffuse between two hot spots and hence generating one "cat door" shaped cut on the membrane.

Figure 26:
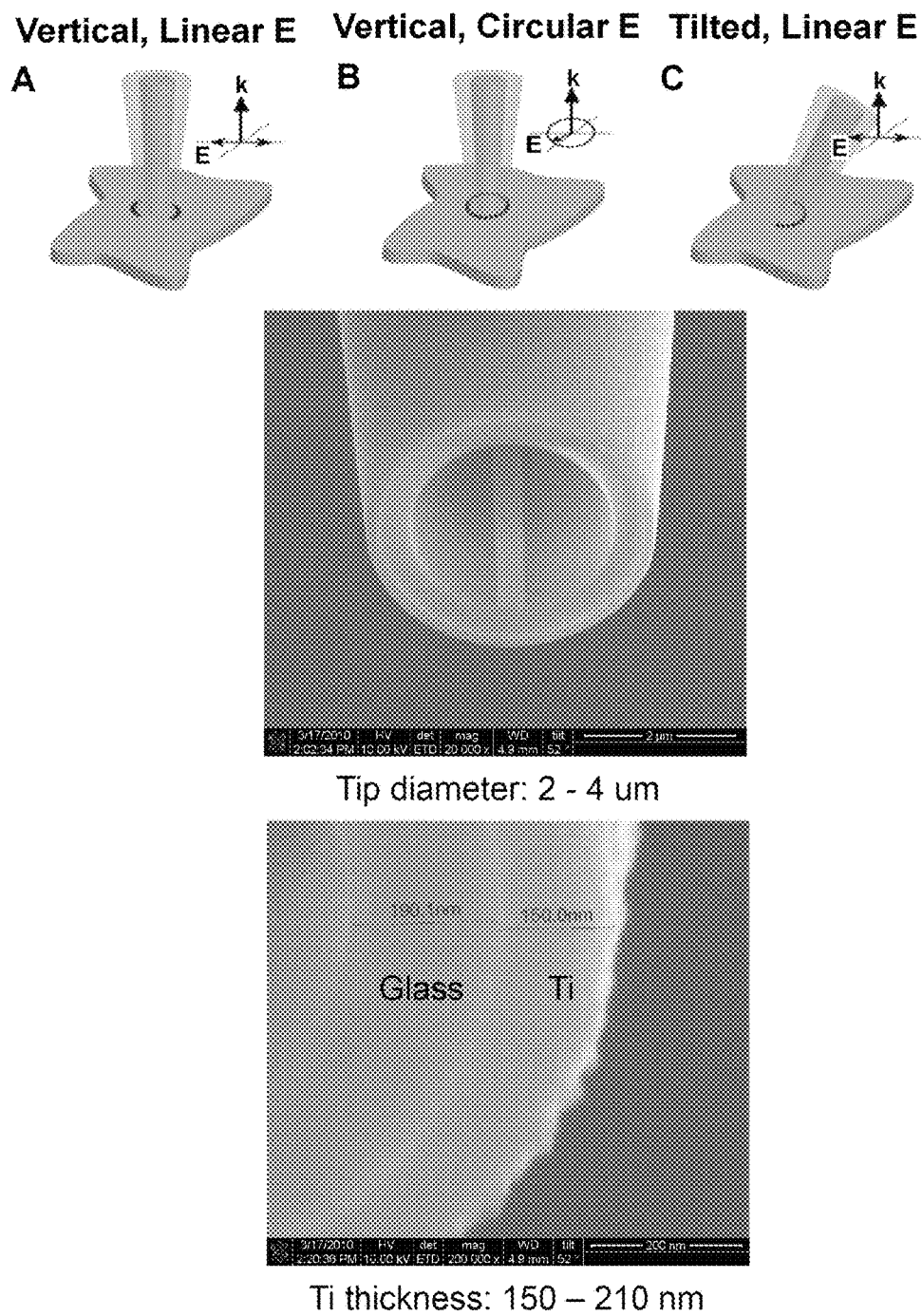
FIG. 26 illustrates cell membrane cutting patterns produced by the photothermal nanoblade under different laser polarizations and micropipetteorientations. Laser fluence=360 mJ/cm². Pipette tip diameter=2 μm. (a) Linear polarization. (b) Circular polarization. (c) Linearly polarized laser excitation with micropipettetilted at 30° from the vertical axis. Bar in inset=1 μm.

This is illustrated in FIG. 26. In order to preserve the cutting patterns by the photothermal nanoblade for imaging, HeLa cells were pre-treated with glutaraldehyde for 20 min to induce protein cross-links and significantly slow cell membrane resealing. During laser pulsing (laser fluence at 360 mJ/cm$^2$), a 2 μm-sized tip diameter Ti coated micropipette was placed in light contact perpendicular to the cell membrane surface.

After laser pulsing, cell membranes were imaged under a scanning electron microscope. Two holes, each <1 μm, were cut in the cell membrane along either side of the Ti nanostructure coated tip by applying a linearly polarized laser pulse, whereas a circular-shaped cut (~1.5 μm diameter) was made by circularly polarized laser excitation (FIGS. 26($a$) and 26($b$)), matching the corresponding bubble patterns. By tilting the microcapillary so that only one side of the Ti ring was in light contact with the cell membrane, a ~1.5 μm "cat-door" half-moonlike opening was produced in the membrane (FIG. 26 ($c$)). These controlled cutting patterns were highly reproducible.

In another illustrative, but non-limiting configuration, the pipette has titanium coating on both the tip and outer wall of the glass capillary. In this case bubble is generated all around the tip (donut). Membrane cutting is confined to the area in contact with the pipette tip. In this scenario, bubble shape does not vary significantly with pipette tilt or laser polarization, which, in certain embodiments, is better suited for microinjection.

The cell surgery tool can provide precise intracellular access through specifically-sized membrane holes that remain open for periods determined by the operator, or that close rapidly as needed, with minimal to no cell damage for live-cell manipulations. The device can be used to increase the efficiency and success rate for performing pronuclear DNA microinjection, embryonic stem cell transfer into blastocysts, somatic cell nucleus transfer, repair or replacement of other intracellular organelles, for the introduction of non-cellular materials, such as probes, and the like.

Substrates for Delivery of Reagents and Cell Transfection.

In another embodiment, methods, devices, and systems are provided for the delivery of agents (e.g., nucleic acids, proteins, organic molecules, organelles, antibodies or other ligands, etc.) into live cells and/or the extraction of the same from said cells. Typically the devices comprise a substrate bearing particles (e.g., nanoparticles) and/or a thin film (e.g., as described above). Cells can be seeded on this substrate and, optionally grown until a confluent culture forms. In certain embodiments a pulsed laser (or other electromagnetic energy source) can irradiate the entire substrate, or selectively irradiate a region of the substrate (e.g., by irradiating a shadow mask whereby the corresponding illumination pattern is imaged onto the substrate). In the area exposed to the energy source (e.g., pulsed laser) the particles and/or thin film is heated to high temperatures due to absorbed energy. Typically, within a few nanoseconds, the heat is dissipated into the liquid medium layer surrounding the particles and/or thin film, thereby generating vapor bubbles. The rapid expansion and subsequent collapse of the vapor bubbles gives rise to transient fluid flows that induce strong shear stress on the nearby cell(s) causing localized pore formation in the cell membrane (and/or cell wall). As a result, membrane-impermeable molecules can be carried into the cell by fluid flows or thermal diffusion. Since the cavitation bubbles) preferentially form where the particle(s) and/or thin film is exposed to the energy source, irradiation patterns can be selected/designed that induce molecular uptake in specified areas of the cell culture and/or at specified times. Location of the region of uptake on the substrate can be determined by a combination of the pattern of particle/nanoparticles and/or thin films in combination with the pattern of illumination. Similarly timing of uptake can be controlled by timing of illumination. In this way high-throughput, spatially-targeted and/or temporally-targeted molecular delivery is made possible by controlling the particle size, material, and/or density on the substrate and/or film material and/or thickness on the substrate, the energy source timing, intensity and frequency, and the irradiation pattern(s).

In another illustrative embodiment a reagent delivery platform (e.g., a transfection substrate) is provided by integrating energy absorbing films and/or micro- or nanoparticles on substrates and/or microfluidic structures. In certain embodiments the nanoparticles and/or thin film can be localized at, on, or near certain features (e.g., pores protuberances, channels, and the like) that are fabricated on the substrate. In certain embodiments, the particles/nanoparticles and/or thin film is disposed on the "top side" of the substrate (where the cell(s) are disposed), while in other embodiments, additionally or alternatively, the particles/nanoparticles and/or thin film is disposed on the bottom side of the substrate (e.g., the side opposite the side upon which the cells are disposed). In either case, the energy absorbing films or particles (e.g., metal particles/nanoparticles, and/or thin films) strongly absorb electromagnetic waves with frequencies close to the surface plasmon frequency and rapidly heat up, due to the absorbed energy, to generate a superheating phenomenon with evaporation of the surrounding medium. Upon, for example, laser pulse excitation, nanometer diameter vapor bubbles are created around the nanoparticles or thin film and when in contact or nearby the surface of a cell, this process generates controlled, precisely-sized holes in the cell membrane (and/or cell wall) to permit the entry or exit of, for example, a reagent. The cavitation or "hole punching" process is finished within a few nanoseconds. As a result, the rest of the membrane does not have time to substantially respond and remains mechanically relatively undisturbed.

Figure 14:
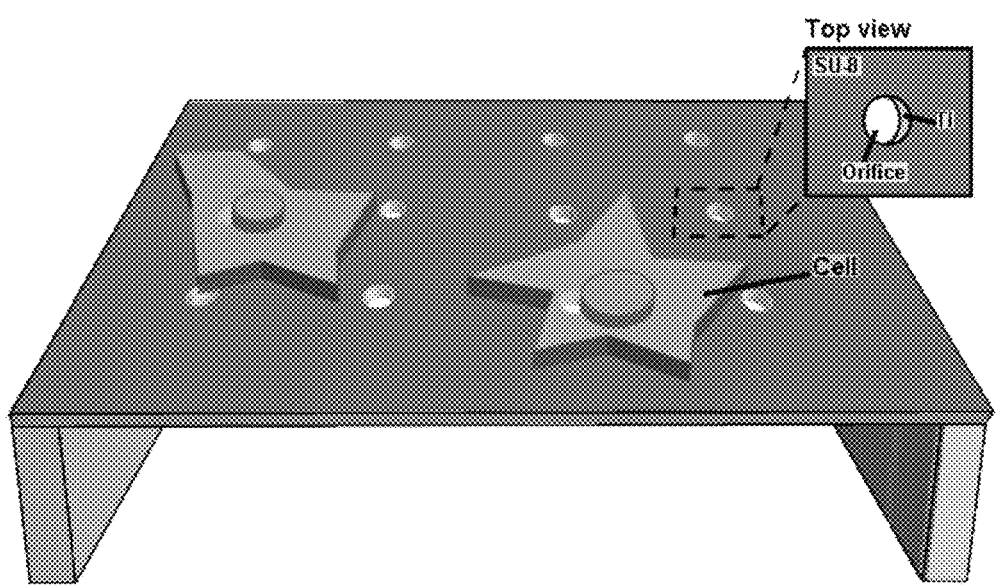
FIG. 14 schematically illustrates a substrate for parallel, selective delivery of one or more reagents into cells.
Figure 18:
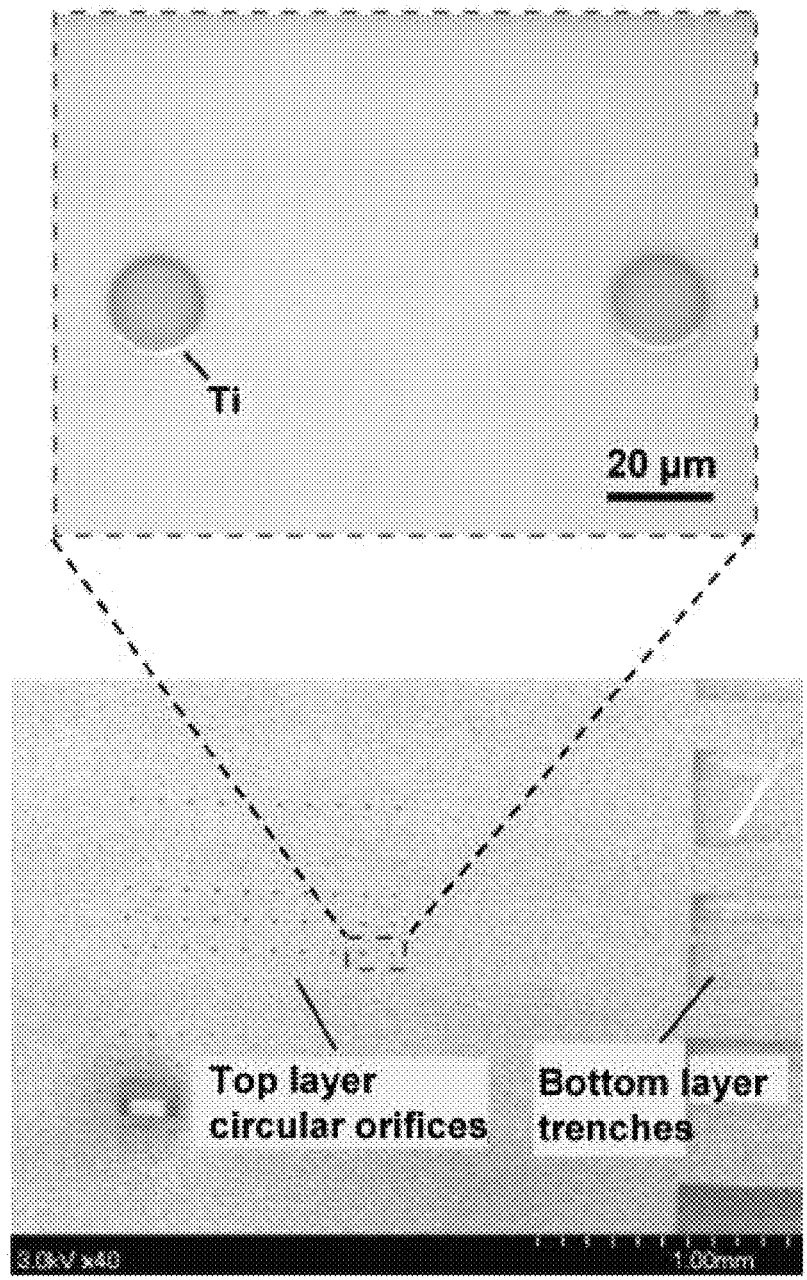
FIG. 18 shows a photograph of an illustrative transfection substrate.

In certain embodiments such devices can comprise one or more microfluidic orifices (e.g., on/into/through a substrate) with the energy absorbing film (e.g., a Ti film) or nanoparticles disposed on the lip of, and/or on the side-wall of, the orifice(s) (or near to the edge of the orifices) (see, e.g., FIG. 14 and FIG. 18). In certain embodiments the device comprises arrays of microfluidic orifices (e.g., 2 or more, 3 or more, 4 or more, 5 or more, 10 or more, 20 or more, 50 or more, 100 or more orifices) with energy absorbent microparticles or film on the lip or side wall(s) or near the orifices. The orifice(s) can be connected to one or to a network of channels (e.g., microfluidic channels). Cells can be disposed on or near the orifice(s).

Figure 15:
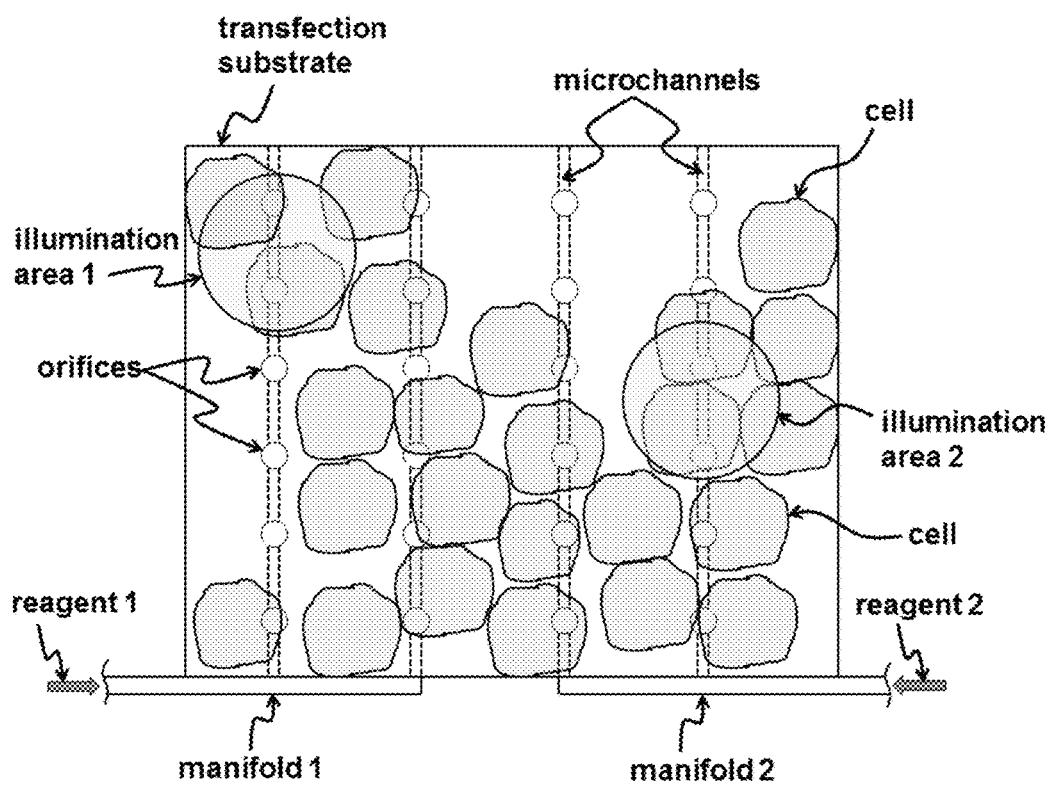
FIG. 15 schematically illustrates one configuration of a "transfection substrate" comprising microchannels to selectively deliver reagents into cells.

Without being bound to a particular theory, it is believed there are two mechanisms for cell membrane opening in such devices. One is direct contact (or close proximity) of the cell membrane with the particle or film so cavitation bubble(s) are generated right next to the cell membrane and disrupts it. Another mechanism is when the cell membrane is not in contact with the particle and/or thin film. For example, in the case where the cells and particles and/or film are on opposite sides of the substrate, the cavitation bubbles squeeze fluid through cavities/pores and the resulting liquid jet punctures the cell membrane. I One such substrate (e.g., transfection substrate) is schematically illustrated in FIG. 15. As illustrated therein, the substrate comprises rows of orifices where each row is joined by a microchannel. In this illustrative, but non-limiting embodiment, two manifolds are provided that each deliver reagents into two microchannels. The surfaces near or comprising the orifices are coated with a thin film (e.g., a thin film comprising Ti) and/or nanoparticles that are selectively heated when illuminated. Selective areas (e.g., illumination areas 1 and 2) of the substrate can be illuminated as desired to effect delivery of the reagents into cells disposed within the illumination area. While FIG. 15 illustrates two manifolds, in various embodiments, more or fewer manifolds are contemplated. Additionally or alternatively, delivery of reagents to orifices can be controlled by a valve system. In certain embodiments the manifolds can be eliminated.

In one illustrative, but non-limiting embodiment, a reagent delivery platform is provided by integrating energy absorbing films and/or micro- or nanoparticles on microfluidic structures. Such devices can comprise one or more microfluidic orifices (e.g., on/into/through a substrate) with the energy absorbing film (e.g., a Ti film) or nanoparticles disposed on the lip of, and/or on the side-wall of, the orifice(s) (or near to the edge of the orifices) (see, e.g., FIG. 14). In certain embodiments the device comprises arrays of microfluidic orifices (e.g., 2 or more, 3 or more, 4 or more, 5 or more, 10 or more, 20 or more, 50 or more, 100 or more orifices) with energy absorbent microparticles or film on the lip or side wall(s) or near the orifices. The orifice(s) can be connected to one or to a network of channels (e.g., microfluidic channels). Cells can be disposed on or near the orifice(s).

Figure 16A:
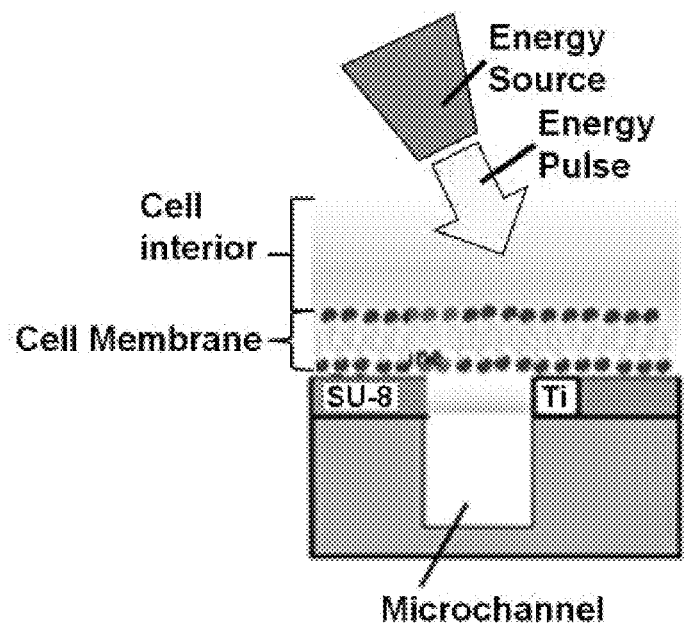
FIGS. 16A-16C, schematically illustrate the operation of one illustrative substrate for parallel, selective delivery of one or more reagents into cells.
Figure 16B:
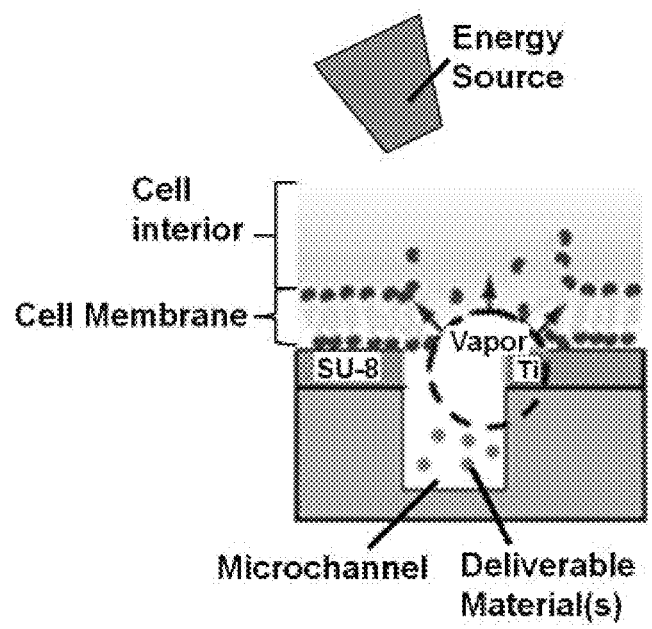
Figure 16C:
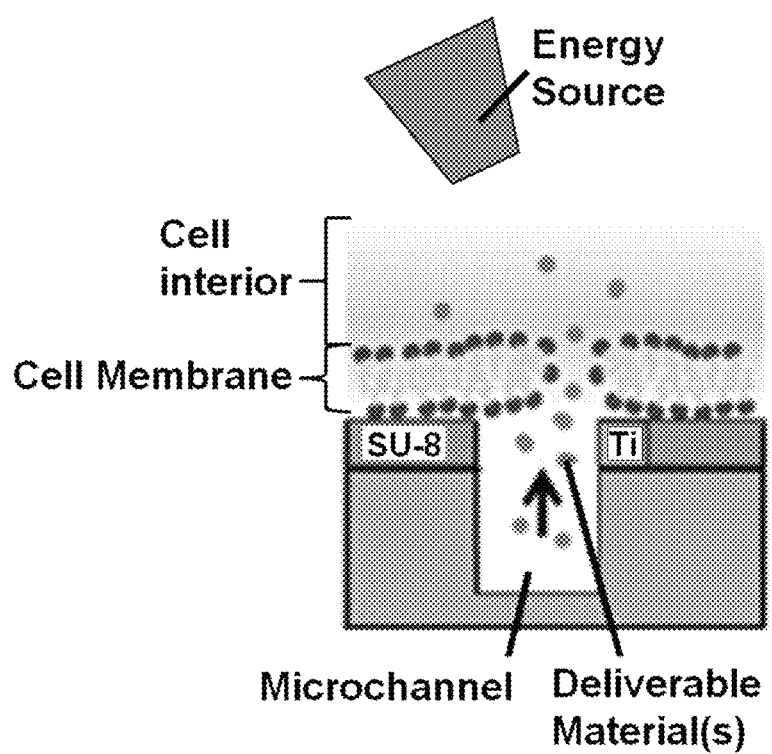

As schematically illustrated in FIG. 16, upon heating/excitation of the orifice(s), e.g., via laser pulsing), openings form in the cell membrane and/or cell wall, and reagents in the microfluidic channel(s) can be delivered into the cells by diffusion, or by pumping the fluid through the microchannel(s) using for example, an external pressure source.

In various embodiments the orifice(s) range in diameter from about 1 µm up to about 100 µm or up to about 50 µm, or from about 2 µm or about 5 µm up to about 20 µm or 30 µm, or from about 1 µm, or 2 µm, or about 5 µm, up to about 10 µm, or about 15 µm, or about 20 µm, or about 25 µm, or about 30 µm, or from about 5 µm up to about 10 µm, 15 µm or 20 µm. In certain embodiments the orifice(s) are about 10 µm in diameter.

In various illustrative embodiments, the microfluidic channels (microchannels) have a width and/or a depth of about 1000 µm or less, or a width and/or a depth (or diameter or characteristic dimension) of about 800 µm or less, or a width and/or a depth (or diameter or characteristic dimension) of about 500 µm or less, or a width and/or a depth (or diameter or characteristic dimension) of about 400 µm or less, or a width and/or a depth (or diameter or characteristic dimension) of about 300 µm or less, or a width and/or a depth (or diameter or characteristic dimension) of about 200 µm or less, or a width and/or a depth (or diameter or characteristic dimension) of about 150 µm or less, or a width and/or a depth (or diameter or characteristic dimension) of about 100 µm or less, or a width and/or a depth (or diameter or characteristic dimension) of about 50 µm or less, or a width and/or a depth (or diameter or characteristic dimension) of about 20 µm or less.

By selectively irradiating/heating certain orifices, reagents (e.g., as described herein) can be selectively delivered to cells on top or in proximity to the irradiated/heated orifice. Similarly, by selectively providing materials to be delivered in appropriate microchannel(s) the same material or different materials can be delivered to different cells on the same substrate.

The "addressable" delivery devices/substrates described herein can be used in a wide variety of contexts. For example, in high throughput systems (different wells or different regions of a single well can have reagents selectively delivered into the target cells simply by administering the agent to the medium and irradiating (e.g., with laser radiation) the region containing the cells into which the agent is to be transported. The first agent can then be washed out, a second agent applied, and a different region irradiated thereby producing cells transfected with different agents at different locations in the culture. This facilitates massively parallel processing of cells permitting the extraordinary control over the timing and spatially addressable delivery of one or more agents.

While, in certain embodiments, the materials to be transfected into the cells are provided in microchannels in fluid communication with orifices on the substrate, the devices need not be operated in this modality. For example, the materials to be transfected into the cells can be provided in the culture medium. Selective heating of a region at or near a cell forms a pore into the cell thereby transfecting the material into the cell. Thus, the nanoparticle or thin film regions can be on an portion of the surface an need not be associated with apertures/orifices.

In certain embodiments the devices described herein can be integrated for example, with other microfluidic devices with pumps and valves (e.g., lab on a chip) for delivery of particular agents to cells.

The embodiments described herein are intended to be illustrative and non-limiting. Using the teaching provided herein, the configuration of such "transfection substrates" and microfluidic devices can be routinely varied changing for example, the features on the substrate (e.g., pore (orifice) size, size distribution, spatial distribution) can be changed, the type of film and/or nanoparticles, the distribution and/or configuration of microfluidic channels, and the like.

Energy Sources and Selective Illumination.

Depending on the selection of materials, the nanoparticles and/or thin film(s) comprising the surgical devices and/or substrates described here can be excited (heated) by application of essentially any of a variety of methods. Such methods include, but are not limited to application of microwaves, lasers, non-coherent optical radiation (e.g., infrared radiation), electrical heating, electron spin resonance (ESR) heating, magnetic heating, and the like. In certain illustrative embodiments, heating of the nanoparticles and/or thin film(s) is accomplished by application of a magnetic field, and/or an electric field, and/or an RF field, and/or light (e.g., a laser).

For example, metal particles/nanoparticles, and/or thin films strongly absorb electromagnetic waves with frequencies close to the surface plasmon frequency, usually in the visible and near-IR range. Particles, nanoparticles, and thin films rapidly heat up, due to the absorbed energy, to generate a superheating phenomenon with evaporation of the surrounding medium.

Where the surgical device and/or substrate is to be selectively heated (e.g., a portion of the substrate), it will be appreciated that any means of locally/selectively illuminating the device or substrate can be used. Thus, for example, in certain embodiments, local illumination of a particular region of the substrate can be accomplished by using, e.g., a focused laser, a focused non-coherent light (e.g., infrared) source.

In certain embodiments selective illumination of one or more regions of a substrate is accomplished by using a mask (shadow mask). In certain embodiments, local illumination can be achieved simply by focusing the illuminating energy source (e.g., laser) to a particular region using a lens and/or mirror system. In certain embodiments the energy source can be focused at a fixed region and the substrate moved (e.g., using a movable stage or other manipulator) to achieve local illumination of particular regions. The illumination area can take any desired shape. For example, in certain embodiments the illuminated area is circular, square, elliptical, hexagonal, crescent shaped, or any other regular or irregular shape. In certain embodiments multiple areas of the substrate are illuminated either simultaneously, or sequentially.

In certain embodiments the energy pulses (e.g., laser pulses) can be shaped by not only the static shadow masks as demonstrated in the examples, but also by dynamic masks using a spatial light modulator such as a TI's DMD microdisplay or LCD display. This provides real-time and interactive control of microinjection into target cells.

Fabrication.

In certain embodiments single cell surgery devices are provided comprising a micropipette having at or near the tip particles or nanoparticles and/or thin films that can be heated using a source of electromagnetic energy (e.g., a laser). In various embodiments cell transfection devices are provided comprising a substrate (e.g. a cell culture vessel, a microtiter plate, etc.) comprising nanoparticles and/or thin films that can be heated using a source of electromagnetic energy (e.g., a laser).

The micropipettetes and "transfection substrates" described herein can be fabricated using methods known to those of skill in the art. For example, in various embodiments an injection micropipette is fabricated using, for example, a commercial pipette puller, while substrates can be fabricated using microfabrication methods known in the semiconductor industry.

Microcapillary/Micropipettefabrication.

The microcapillary/micropipette can be fabricated from any material that can be pulled, etched, or otherwise fabricated to the desired dimension(s) while providing the requisite stiffness and heat resistance to permit heating and cell penetration. In addition, the material is preferably not toxic to the cell(s) of interest. In certain embodiments the microcapillary comprises a material such as glass, a mineral (e.g., quartz), a ceramic, a plastic (e.g., DELRIN®, TEFLON®, etc.), a metal, a semiconductor, and the like.

When the micropipettetes is fabricated, the cross-sectional shape of the pipette is typically circular. However, this does not mean that only circular pipettes can be used for the cell surgery tool. Micropipettetes having other cross-sections can be fabricated. For example, pipette tips with any desired patterns, circular, rectangular, or triangular can be fabricated on a glass or silicon wafer first and then transferred and assembled with an injection pipette.

In addition, a number of pre-pulled micropipettetes are commercially available (see, e.g., World Precision Instruments, Hertfordshire, England).

Pipette diameter is an important parameter for the single-cell surgery instrument. One advantage of the single-cell surgery instrument described herein is that it allows opening a ~µm size hole in a cell membrane with less collateral damage to the cell. This allows the delivery large size DNAs or other materials into a cell without killing it. To reduce collateral damage, conventional micropipette techniques typically require the outer tip diameter of a glass pipette to be smaller than 200 nm to facilitate the penetration across the flexible cell membrane of small mammalian cells. This restriction greatly limits the size of particles that can be delivered through conventional micropipette techniques. Materials such as chromosomes, nuclei, organelles, or other extracellular materials have great research and commercial value, but often have a size larger than the physical size of the pipette opening and cannot be introduced into cells through conventional techniques.

The "laser" cell surgery pipette described herein provides a unique solution to this problem which has the potential to revolutionize the entire micropipette industry. In general, the methods and devices of this invention are effective to introduce large DNA fragments (e.g., BAC-sized or larger DNA), nuclei, organelles, and other large moieties into cells more efficiently with less cell damage than other techniques. Accordingly, in certain embodiments, the micropipette comprising the single cell surgery tool described herein has a tip diameter greater than 200 nm, in certain embodiments greater than about 300 nm, greater than about 400 nm, greater than about 500 nm, greater than about 600 nm, greater than about 700 nm, greater than about 800 nm, or greater than about 900 nm or 1 µm.

Transfection Substrate Fabrication.

Similarly the substrate(s) comprising the "transfection substrate" can be fabricated from any convenient material that is preferably not toxic to the cell(s), that can carry the particle, nanoparticle, or thin film coating, and that can tolerate the local heating produced by application of electromagnetic energy to the particles, nanoparticles, and/or thin film(s). Suitable materials include, but are not limited to glass/silicion, germanium, a mineral (e.g., quartz), a ceramic, a plastic (e.g., DELRIN®, TEFLON®, etc.), a metal, a semiconductor, and the like.

In certain embodiments, the substrate comprises a surface of a vessel used for cell screening and/or for cell culture. This can include, for example, vessels for adherent or suspended cell culture. This can also include, microtiter plates (e.g., 96, 384, 864, 1536 well, etc.), microfluidic devices, high density (microarray) substrates, microscope slides or chambers, and the like.

Figure 17:
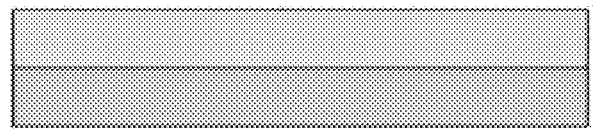
FIG. 17 schematically illustrates one method of fabricating a substrate such as the one illustrated in FIG. 14.
Figure 17:
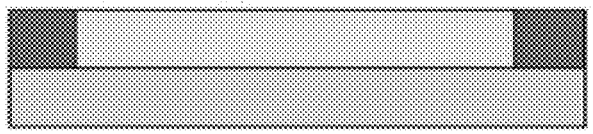
Figure 17:
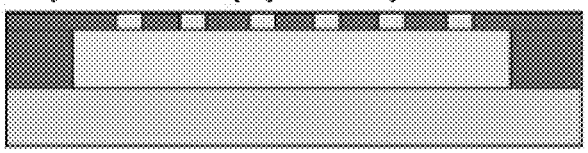
Figure 17:
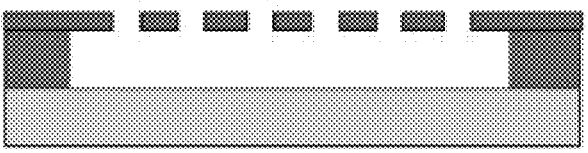
Figure 17:
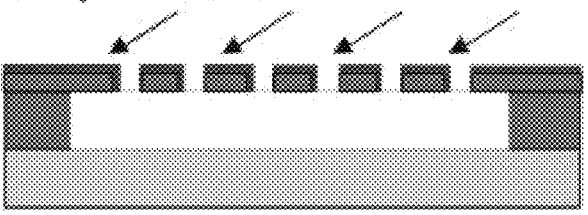
Figure 17:
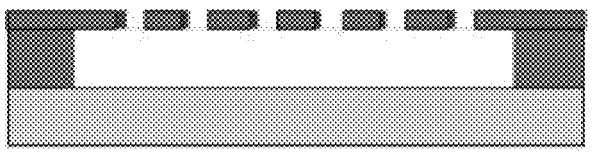

In certain embodiments the cell transfection substrates are fabricated using techniques known in the semiconductor industry. One approach is schematically illustrated in FIG. 17. In this illustrative embodiment, the microfluidic orifices and channels are fabricated by patterning SU-8 photoresists on a glass coverslip substrate. First the bottom trenches are defined photolithographically in a layer of 100-µm-tall SU-8 2075 photoresist. Another thin layer (4 µm thick) of SU-8 2005 photoresist is spun coated onto the bottom layer and circular openings are defined by a second photolithography step. After developing the two-layer SU-8 structure, 100 nm thick Ti thin film is deposited onto the structure by electron beam evaporation at a substrate incline angle of 60 degrees to coat both the top and the sidewalls of the circular orifices. Final steps involve dry etching the top layer Ti and connecting the microchannels to an external fluidic pump. Bottom trenches in one illustrative embodiment were 200 µm wide and 300 µm apart. The circular orifices had diameters ranging from 10 to 20 µm. These orifices were arranged in a square array and separated by 100 µm. A new-moon shaped Ti thin film was coated on the sidewalls of the circular orifices.

While the illustrated orifices are circular, they need not be so limited. Using standard methods (e.g., etching methods) orifices of essentially any shape (e.g., round, square, pentagonal, hexagonal, ellipsoid, trapezoidal, irregular, etc.) can be produced. Similarly, the patterning of the orifices can be in essentially any desired pattern.

While, in certain embodiments, the nanoparticles and/or thin film are coated on a portion of the orifice (e.g., by depositing the film at an angle) in certain other embodiments, the orifice and/or remaining surface is uniformly coated with nanoparticles and/or a thin film.

Particle/Nanoparticle/Thin Film Materials

In various embodiments the particles and/or nanoparticles or thin film(s) comprising the various devices described herein are all formed of the same material. In other embodiments, particles and/or nanoparticles or thin film(s) in a particular device include different materials. Thus for example, a given device (e.g., pipette or transfection substrate) can include particles/nanoparticles or thin films having two, three, four, five, or more different types of particle (e.g., particle size, and/or shape, and/or material). Similarly, the thin films comprising the devices can comprise multiple films (e.g., as multiple layers, or different films at different locations on the micropipetteor substrate). For example, the devices can be modified by coating another layer of metal, or dielectric materials (e.g., silicon oxide, silicon nitride, etc.) on top of the metal thin film to control the heat dissipation pathways and to control the microbubble expansion patterns which effects the amount of area on the cell that is damaged by the substrate heating or by the pipette tip.

In various embodiments the particles/nanoparticles and/or thin films on the micropipette and/or "transfection substrate" are fabricated from a metal, metal alloy, semiconductor, or other material that can be heated by the application of appropriate electromagnetic energy. In various embodiments semiconductors, metals, metal alloys, and oxides and/or nitrides thereof are contemplated. Depending on size, aspect ratio, film thickness, and/or material, such metals are readily heated using various energy sources (e.g., laser light, electric field, RF field, magnetic field, ultrasonic source, etc.).

While most of the discussion provided herein pertains to semiconductor or metal particles/nanoparticles and/or films, and the examples describe gold particles and/or gold or titanium films, the materials heated by the energy source need not be so limited. Essentially any material that absorbs the appropriate energy with resultant heating can be used for the heating material in the methods and devices described herein. Accordingly, in certain embodiments, nanoparticles and/or films comprising materials such as gold, silver, tantalum, platinum, palladium, rhodium, or titanium, or oxides, nitrides, or alloys thereof are contemplated.

One important material useful in the nanoparticles and/or thin film(s) comprising devices and methods described herein is titanium (Ti) and/or oxides, nitrides, alloys or doped oxides, doped nitrides, or alloys thereof. In certain embodiments the nanoparticles and/or thin film(s) comprising devices and methods described herein comprise titanium and/or titanium nitride (TiN), which is a very hard material with a melting temperature three times higher than gold. When coated on a pipette, 40 cells have been consecutively injected using one single pipette without seeing any pipette damage. This also means that a TiN coated pipette can potentially inject hundreds or thousands of cells without the need to change the pipette. This is a significant improvement as compared to a gold coated pipette, which can be damaged by the strong explosive bubbles and high temperature excitation in one, two, or a few uses.

Other variants of TiN are well known to those of skill in the art. These include, but are not limited to titanium carbon nitride (TiCN) and titanium aluminum nitride (TiAlN), which can be used individually or in alternating layers with TiN or in mixed particle populations with TiN particles. These coatings offer similar or superior enhancements in corrosion resistance and hardness, and different (even tunable) absorption properties.

As indicated above, the particle or films comprising the devices and/or substrates described herein need not be limited to materials comprising metals. For example, we have demonstrated that black carbon can also induce explosive bubbles near the pipette and kill or penetrate a single cell. Accordingly, in certain embodiments, for example, carbon nanoparticles, including, but not limited to carbon nanotubes can be used in the methods and devices described herein.

In various embodiments particles/nanoparticles, and/or thin films comprising one or more materials from Groups II, III, IV, V, or VI of the periodic table are also contemplated as well as oxides, nitrides, alloys, and doped forms thereof and/or transition metals, transition metal oxides, transition metal nitrides, alloys or composites comprising transition metals, and the like are contemplated. In certain preferred embodiments, the nanoparticles and/or films comprise Group II, Group III, Group IV, Group V materials (e.g., carbon, silicon, germanium, tin, lead), doped Group II, III, IV, V, and VI elements, or oxides of pure or doped Group II, III, IV, V, or VI elements or transition metals, transition metal oxides or transition metal nitrides. In certain preferred embodiments the particles/nanoparticles and/or thin films comprise a Group III, IV, or V semiconductor.

It will be understood from the teachings herein that in certain embodiments, the particles/nanoparticles and/or thin films include one or more materials such as Si, Ge, SiC, Au, Ag, Cu, Al, Ta, Ti, Ru, Ir, Pt, Pd, Os, Mn, Hf, Zr, V, Nb, La, Y, Gd, Sr, Ba, Cs, Cr, Co, Ni, Zn, Ga, In, Cd, Rh, Re, W, and their oxides and nitrides.

As indicated above, in various embodiments, the group II, III, IV, V, or VI element, transition metal, transition metal oxide or nitride comprising the nanoparticle(s) and/or thin film can be essentially pure, or it can be doped (e.g., p- or n-doped) and/or alloyed. P- and n-dopants for use with Group II-VI elements, in particular for use with Groups III, IV, and V elements, more particularly for use with Group IV elements (e.g., silicon, germanium, etc.) are well known to those of skill in the art. Such dopants include, but are not limited to phosphorous compounds, boron compounds, arsenic compounds, aluminum compounds, and the like.

In certain embodiments the particles/nanoparticles and/or films comprise Group IV semiconductors such as silicon, germanium, and silicon carbide. The most common dopants for such semiconductors include acceptors from Group III, or donors from Group V elements. Such dopants include, but are not necessarily limited to boron, arsenic, phosphorus, and occasionally gallium.

As indicated above, in various embodiments, the particles/nanoparticles comprise a semiconductor. Many doped Group II, III, IV, V, or VI elements are semiconductors and include, but are not limited to, ZnS, ZnSe, ZnTe, CdS, CdSe, CdTe, MgS, MgSe, MgTe, CaS, CaSe, CaTe, SrS, SrSe, SrTe, BaS, BaSe, BaTe, GaN, GaP, GaAs, GaSb, InP, InAs, InSb, AlS, AlP, AlSb, PbS, PbSe, $Cd_3Sb_2$, $Zn_3P_2$, $Zn_3As_2$, $Zn_3Sb_2$, $TiO_2$, $TiO_2$, $TiO_2$, $Cu_2O$, CuO, $UO_2$, $UO_3$, $Bi_2O_3$, $SnO_2$, $BaTiO_3$, $SrTiO_3$, $LiNbO_3$, $La_2CuO_4$, $PbI_2$, $MoS_2$, GaSe, SnS, $Bi_2S_3$, GaMnAs, InMnAs, CdMnTe, PbMnTe, $La_{0.7}Ca_{0.3}MnO_3$, FeO, NiO, EuO, EuS, $CrBr_3$, $Cu(In,Ga)Se_2$, $Cu_2ZnSnS_4$, $CuInSe_2$, $AgGaS_2$, $ZnSiP_2$, $As_2S_3$, PtSi, $BiI_3$, $HgI_2$, TlBr, Se, $Ag_2S$, $FeS_2$, Ge and Si and ternary and quaternary mixtures thereof, and the like.

In addition to laser energy, magnetic, electric fields, and RF fields can also readily be used to heat particles, nanoparticles and/or certain thin films. Thus, for example, U.S. Patent Publication No: 2007/0164250, which is incorporated herein by reference, provides magnetic nanoparticles, that when placed in a magnetic field are selectively heated at a certain frequency of the magnetic field, as a function of their size, composition, or both.

In various embodiments such nanoparticles or films comprise magnetic materials (such as the Ferro V magnetic pigment) that transduce energy when exposed to a magnetic field of sufficient intensity. Thus, for example, an alternating magnetic field will induce an alternating current in the particle, producing heat. A variety of magnetic materials can be used. Such materials include, but are not limited to magnetic materials, such as $Fe—O_4$, $Fe_2O_3$. Also, in certain embodiments, silver, copper, platinum, palladium and the like can comprise the particles, nanoparticles, and/or thin films used in the devices of this invention. In certain embodiments the particles, nanoparticles, and/or thin films can comprise $TiO_2$, $CeO_2$, Ag, CuO, yttrium aluminum garnet (YAG), $InO_2$, CdS, $ZrO_2$, or a combination thereof. In another embodiment, any metal oxide, metal alloy, metal carbide, and/or transition metal, may be used in the instant invention. In some embodiments, the particles can be coated, such that the coating does not alter their respective responsiveness to the applied field.

In certain embodiments, particles, nanoparticles, or thin films used in the devices of the present invention can be made of magnetic materials, while in other embodiments, they can be made of or comprise paramagnetic or superparamagnetic materials.

Accordingly, in certain embodiments the particles, nanoparticles and/or thin films can comprise a paramagnetic or superparamagnetic material that can be heated using electron spin resonance absorption (SPM) and/or ferromagnetic resonance. Electron spin resonance (ESR) heating and ferromagnetic resonance (FMR) heating are described in US Patent Publications 2006/0269612 and 2005/0118102, which are incorporated herein by reference. Yttrium-iron garnet $Y_3Fe_5O_{12}$ and $\gamma$-$Fe_2O_3$ are two well-known materials suitable ESR and/or FMR heating. Different dopants can be added to lower the spin resonance frequencies of these materials various applications. Magnetic garnets and spinels are also chemically inert and indestructible under normal environmental conditions.

Also contemplated are various materials and/or semiconductors comprising materials from Groups II, III, IV, and V of the periodic table.

An illustrative list of potential dilutant ions for the generic $\{c\}_3(a)_2[d]_3O_{12}$ and spinel $A[B]_2O_4$ ferrite compounds are presented in Table 1.

TABLE 1

Illustrative ferrite diluent ions.

| Garnet $\{c\}_3(a)_2[d]_3O_{12}$ | | Spinel $A[B]_2O_4$ | |
|---|---|---|---|
| {c} dodecahedral | (a) octahedral [d] tetrahedral | A tetrahedral | [B] octahedral |
| $Y^{3+}$ | $Fe^{3+}$ | $Fe^{3+}$ | $Fe^{3+}$ |
| $La^{3+}$ | $Mn^{2+}$ | $Mn^{2+}$ | $Mn^{2+}$ |
| $Gd^{3+}$ | $Ru^{3+}$ | $Ru^{3+}$ | $Ru^{3+}$ |
| $Eu^{2+}$ | $Cu^{1+}$ | $Cu^{1+}$ | $Cu^{1+}$ |
| $Na^{1+}$ | $V^{3+}$ [d], $Ni^{2+}$ (a) | $V^{3+}$ | $Ni^{2+}$ |
| $K^{1+}$ | $Cr^{4+}$ [d], $Cu^{3+}$ (a) | $Cr^{4+}$ | $Cu^{3+}$ |
| $Rb^{1+}$ | $Mo^{4+}$ [d], $Cr^{3+}$ (a) | $Mo^{4+}$ | $Cr^{3+}$ |
| $Tl^{1+}$ | $W^{4+}$ [d], $Mo^{3+}$ (a) | $W^{4+}$ | $Mo^{3+}$ |
| $Ag^{1+}$ | $Nb^{3+}$ [d], $W^{3+}$ (a) | $Nb^{3+}$ | $W^{3+}$ |
| $Au^{1+}$ | $Zn^{2+}$ | $Zn^{2+}$ | $Zn^{2+}$ |
| $Hg^{1+}$ | $Mg^{2+}$ | $Mg^{2+}$ | $Mg^{2+}$ |
| $Ca^{2+}$ | $Al^{3+}$ | $Al^{3+}$ | $Al^{3+}$ |
| $Sr^{2+}$ | $Ga^{3+}$ | $Ga^{3+}$ | $Ga^{3+}$ |
| $Ba^{2+}$ | $In^{3+}$ | $In^{3+}$ | $In^{3+}$ |
| $Hg^{2+}$ | $Sc^{3+}$ | $Sc^{3+}$ | $Sc^{3+}$ |
| $Pb^{2+}$ | $Ti^{4+}$ | $Ti^{4+}$ | $Ti^{4+}$ |
| $Bi^{3+}$ | $Zr^{4+}$ | $Zr^{4+}$ | $Zr^{4+}$ |
| $In^{3+}$ | $Hf^{4+}$ | $Hf^{4+}$ | $Hf^{4+}$ |
| $Sc^{3+}$ | $Si^{4+}$ | $Si^{4+}$ | $Si^{4+}$ |
|  | $Si^{4+}$ | $Si^{4+}$ | $Si^{4+}$ |
|  | $Ge^{4+}$ | $Ge^{4+}$ | $Ge^{4+}$ |
|  | $Sn^{4+}$ | $Sn^{4+}$ | $Sn^{4+}$ |
|  | $V^{5+}$ | $V^{5+}$ | $V^{5+}$ |
|  | $Nb^{5+}$ | $Nb^{5+}$ | $Nb^{5+}$ |
|  | $Ta^{5+}$ | $Ta^{5+}$ | $Ta^{5+}$ |
|  | $P^{5+}$ | $P^{5+}$ | $P^{5+}$ |
|  | $As^{5+}$ | $As^{5+}$ | $As^{5+}$ |
|  | $Sb^{5+}$ | $Sb^{5+}$ | $Sb^{5+}$ |

The particle or nanoparticles can take any of a number of possible morphologies and still be suitable for use in the present invention. Thus, for example, this invention contemplates using nanotubes of the following kinds: single walled, double walled, multi walled, with zig-zag chirality, or a mixture of chiralities, twisted, straight, bent, kinked, curled, flattened, and round; ropes of nanotubes, twisted nanotubes, braided nanotubes; small bundles of nanotubes (e.g., in certain embodiments, with a number of tubes less than about ten), medium bundles of nanotubes (e.g., in certain embodiments, with a number of tubes in the hundreds), large bundles of nanotubes (e.g. in certain embodiments, with a number of tubes in the thousands); nanotorii, nanocoils, nanorods, nanowires, nanohorns; empty nanocages, filled nanocages, multifaceted nanocages, empty nanococoons, filled nanococoons, multifaceted nanococoons; thin nanoplatelets, thick nanoplatelets, intercalated nanoplatelets, nanocones, and the like. The various nanoparticles (nanostructures) can assume heterogeneous forms. Such heterogeneous forms include, but are not limited to structures, where one part of the structure has a certain chemical composition, while another part of the structure has a different chemical composition. An example is a multi walled nanotube, where the chemical composition of the different walls can be different from each other. Heterogeneous forms also include different forms of nanostructured material, where more than one of the above listed forms are joined into a larger irregular structure. In addition, in certain embodiments any of the above materials can have cracks, dislocations, branches or other impurities and/or imperfections.

In certain embodiments, the size of the particles or nanoparticles and/or the area and/or thickness of the thin film(s) for use in the present invention can be adjusted or optimized and reflect the choice of the nanoparticles or film material, the nature of the excitation energy, and frequency and/or strength of the excitation energy. In certain embodiments the nanoparticles range in size (e.g., length and/or width and/or diameter) from about 10 to about 500 nm, preferably from about 20 nm to about 200 nm, more preferably from about 20 nm, 30 nm, 40 nm or 50 nm to 100 nm, or 150 nm or 200 nm. In certain embodiments the size of the nanoparticles for use in the present invention ranges from about 4 nm to about 25 nm, in another embodiment, from 8 nm to 5 nm, in another embodiment from 5 nm to 100 nm, in another embodiment, from 10 nm to 800 nm, in another embodiment, from 10 nm to 50 nm, in another embodiment, from 50 nm to 200 nm, and in another embodiment from 150 nm to 500 nm.

In various embodiments, where present, metal films range in thickness from about 1, 2, 5, 10, 50, 100, 150, 200, 300, 400, or 500 nm to about 800 nm, 1 μm, 5 μm, 10 μm, 50 μm, or 100 μm. In certain embodiments the metal films range in thickness from about 2 nm or 5 nm, 10 nm, 20 nm, or 30 nm to about 100 nm, 300 nm, 500 nm, 800 nm or 1 μm. In certain embodiments the metal films range in thickness from 1 nm to 150 nm, preferably from about 5 nm to 100 nm, more preferably from about 5 nm, 10 nm, or 20 nm to about 50 nm, 75 nm, or 100 nm. In certain embodiments the metal films are about 30 nm in thickness.

In various embodiments the coated layer comprising the devices described herein can be a continuous thin film, a thin film broken up into small domains (e.g., 5 nm, 10 nm, 20 nm, 50 nm, 100 nm, 200 nm, 500 nm domains), or can comprise discrete particles or nanoparticles as described herein. The shape of the particles and the thickness of thin films as well as the particle or film composition will affect the absorption spectrum of the material and the energy source and intensity required to produce the desired local heating.

In general, the film thickness and/or particle size effects the size of the bubble(s) produced by local heating and the nature of the microfluidic flow near the bubbles. This determines the shear stress produced and the size of the opening(s) produced in the cell. In general, the larger the particles, the larger the bubbles produced and the more impact produced on the cell. The thickness of thin films has a similar effect as the particle size. The thicker the film, the larger the bubble produced and the larger the hole(s) produced in the cell(s).

Fabrication of Particles/Nanoparticles and Application of Particles and/or Films to Microcapillaries and/or to "Transfection Substrates.

Methods of manufacturing particles or nanoparticles and depositing them on a surface or synthesizing such particles in situ on a surface and methods of depositing thin films on surfaces are well known to those of skill in the art.

For example, thin films can be deposited by any suitable method including but not limited to sputtering deposition, chemical vapor deposition (CVD), molecular beam epitaxy (MBE), plasma-assisted vapor deposition, cathodic arc deposition or Arc-PVD, and electron beam evaporation deposition. In the single cell surgery devices, in various embodiments the film will partially or fully cover the tip of the microcapillary to a distance of up to 100 μm, 50 μm, 25 μm, 10 μm, or 5 μm from the tip, to a distance of up to 1 μm from the tip, more preferably to a distance of up to 800 nm, preferably up to 500 nm, more preferably up to 300, 200, 150, 100, 50, or 25 nm from the tip. Thin films can also be chemically deposited on the microcapillary or cell transfection substrate.

Methods of fabricating particles and nanoparticles are also well known to those of skill in the art. Such methods include, but are not limited to combustion synthesis (e.g., using an oxidizer (e.g., metal salt) and a fuel (e.g., organic compounds) in a redox reaction), evaporation/condensation (EC) generators, spray pyrolysis (e.g., plasma processing and powder spray), liquid phase methods using solution chemistry such as supercritical fluids, chemical reduction, or chemical oxidation, mechanical alloying, template methods (e.g., forming nanoparticles within small voids or areas. Zeolites, pillared clays, nanoporous membranes and inverse micelles), and the like (see, e.g., U.S. Pat. Nos. 7,212,284, 7,204,999, 7,147,712, 7,128,891, 6,972,046, 6,688,494, 5,665,277 which are all incorporated herein by reference, and PCT Patent Application No: WO/2007/024323, which is incorporated herein by reference). The production of nanohorns is described, e.g., by Berber et al. (2000) Physical Review B, 62(4): R2291-2294, while the production of nanofibers is described, for example in U.S. Pat. Nos. 6,706,248, 6,485,858, which are incorporated herein by reference. See also, Fedlheim and Colby (2001) *Metal Nanoparticles: Synthesis Characterization & Applications*, Marcel Dekker, Inc., N.Y.; Baraton (2002) *Synthesis, Functionalization and Surface Treatment of Nanoparticles*, American Scientific Publishers; Fendler (1998) *Nanoparticles and Nanostructured Films: Preparation, Characterization and Applications*, Wiley-VCH, N.Y.; and the like.

In certain embodiments the nanoparticles are synthesized in surfactant systems. Such surfactant-based methods are well known to those of skill in the art. One such approach is illustrated in Example 1.

More generally, in certain embodiments, nanoparticles can be formed on the reduction of metallic salts by organic solvents (e.g., ethanol) to form metal colloids (see, e.g., Hirai et al. (1979) *J. Macromol. Sci. Chem.*, A13: 727; Hirai et al. (1976) *Chem. Lett.*, 905; Toshima and Yonezawa (1992) *Makromol. Chem., Macromol. Symp.*, 59: 281; Wang and Toshima (1997) *J. Phys. Chem.*, 97: 11542, and the like). One illustrative approachy is described by Pastoriza-Santos and Liz-Marzan (2000) *Pure Appl. Chem.*, 72(1-2): 83-90. In their approach, $Ag^+$ ions are reduced by N,N-dimethylformamide (DMF) in the presence or absence of a stabilizing agent. The reaction leads to the formation of either thin films of silver nanoparticles electrostatically attached onto surfaces, or stable dispersions of silver nanoparticles.

In another illustrative approach, magnetite nanoparticle materials can be made by mixing iron salt with alcohol, carboxylic acid and amine in an organic solvent and heating the mixture to 200-360° C. The size of the particles can be controlled either by changing the iron salt to acid/amine ratio or by coating small nanoparticles with more iron oxide. Magnetite nanoparticles in the size ranging from 2 nm to 20 nm with a narrow size distribution can readily be obtained. The method can easily be extended to other iron oxide based nanoparticle materials, including $MFe_2O_4$ (where M is for example Co, Ni, Cu, Zn, Cr, Ti, Ba, Mg, and the like) nanomaterials, and iron oxide coated nanoparticle materials. The method also leads to the synthesis of iron sulfide based nanoparticle materials by replacing alcohol with thiol in the reaction mixture. The magnetite nanoparticles can be oxidized to $\gamma\text{-}Fe_2O_3$, or $\alpha\text{-}Fe_2O_3$, or can be reduced to bcc-Fe nanoparticles, while iron oxide based materials can be used to make binary iron based metallic nanoparticles, such as CoFe, NiFe, and FeCoSmx nanoparticles (see, e.g., U.S. Pat. No. 7,128,891, which is incorporated herein by reference).

One method of producing gold nanoparticles involves mixing a gold salt solution with an adsorbent. Gold in the form of complexes is adsorbed onto the surface of the adsorbent. The gold-loaded adsorbent, after being separated from the solution by screening, filtration, settling or other methods, is ashed to form ashes. The ashes contain gold nanoparticles and impurities such as oxides of sodium, potassium and calcium. The impurities can be removed by dissolution using dilute acids. The relatively pure gold nanoparticles are obtained after the impurities are removed. Activated carbon or gold-adsorbing resin can be used as the adsorbent. Silver or platinum group metal nanoparticles can also readily be produced by this method (see, e.g., U.S. Pat. No. 7,060,121, which is incorporated herein by reference.

In still another approach, nanoparticles, can be formed using laser pyrolysis. Conventional laser pyrolysis processes, often called photothermal processes, are well known to those of skill in the art (see, e.g., U.S. Pat. Nos. 5,958,348, 3,941,567, 6,254,928, which are incorporated herein by reference, and the like). In this process, a radiation absorber or other precursor gaseous species absorbs energy (e.g., laser light, which results in the heating of the materials in a reaction zone causing thermally driven chemical reactions between the chemical components in the reaction zone. Typically, laser pyrolysis processes employ a precisely defined hot zone (typically 1000~1500° C.) generated, e.g., by a laser beam passing through a chemical vapor zone, in which gases thermally react to form the desired nanoscale particulate materials. The absence of wall in contact with the hot zone eliminates any contamination.

The materials formed in the pyrolytic reaction leave the hot zone typically driven by gravity or gas flow. The materials are rapidly cooled/quenched thereby forming nanoparticles with a very uniform distribution of sizes and shapes. In typical embodiments, a carbon dioxide ($CO_2$) laser is used to heat the gas molecules directly by light absorption. Another advantage of using a laser is its narrow spectral width, which allows efficient coupling between the light and the molecular precursor that has exact wavelength of absorption (over 15% of laser power consumed). The technology has been used to produce various nanosize materials from metals, metal carbides, metal nitrides and metal oxides (see, e.g., Haggerty et al. (1981) pp 165-241 In: *Laser Induced Chemical Processes*, edited by J. J. Steinfeld; Bi et al. (1993) *J. Mater. Res.*, 8(7): 1666-1674; Bi et al. (1995) *J. Mater. Res.* 10(11): 2875-2884; Curcio et al. (1990) *Applied Surface Science*, 46: 225-229; Danen et al. (1984) *SPIE*, 458: 124-130; Gupta et al. (1984) *SPIE*, 458: 131-139; U.S. Pat. Nos. 5,958,348, 6,225,007, 6,200,674, 6,080,337, and the like).

Similarly, the most common methods of TiN thin film creation are physical vapor deposition (PVD, usually sputter deposition, Cathodic Arc Deposition or electron beam heating) and chemical vapor deposition (CVD). In both methods, pure titanium is sublimated and reacted with nitrogen in a high-energy, vacuum environment.

Bulk ceramic objects can be fabricated by packing powdered metallic titanium into the desired shape, compressing it to the proper density, then igniting it in an atmosphere of pure nitrogen. The heat released by the chemical reaction between the metal and gas is sufficient to sinter the nitride reaction product into a hard, finished item.

The particles or nanoparticles can be attached to the microcapillaries or cell transfection substrate by any of a number of methods known to those of skill in the art. The particles can simply be sputtered in place, formed on the surface during the formation of metal colloids, grown in place on nucleating particles, ionically attached to the surface, or covalently coupled to the surface, e.g., directly or through a linker/functionalizing agent (e.g., —SH, silane (e.g., 3-aminopropyltirmethoxysilane, and the like), and so forth.

Figure 5:
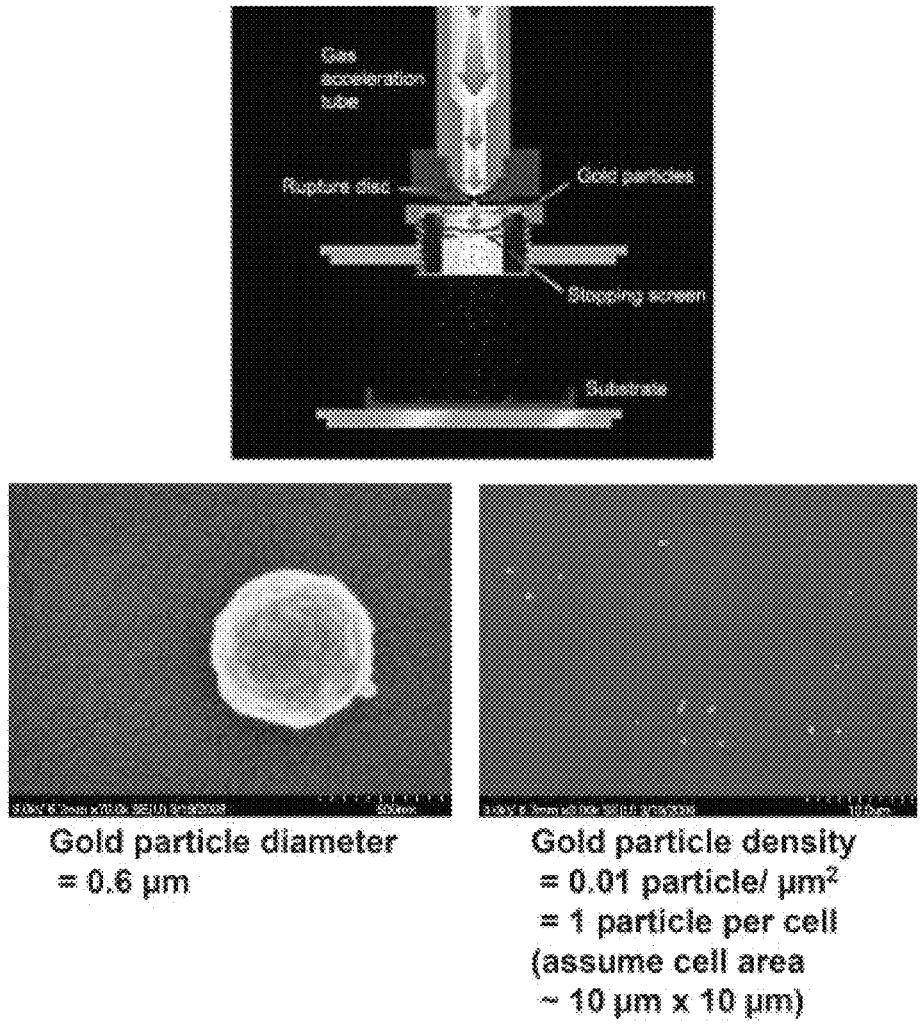
FIG. 5 illustrates the fabrication of a transfection substrate using a biolistic injector (left panel) to bombarding gold particles directly onto a plastic substrate. The middle panel a typical particle on the substrate, while the right panel illustrates the particle density on the substrate.

As illustrated in the examples, in one embodiment, the cell transfection substrate is fabricated by bombarding gold particles directly onto a plastic substrate using a biolistic cell injector (BioRad) (see, e.g., Example 4, and FIG. 5).

Figure 6:
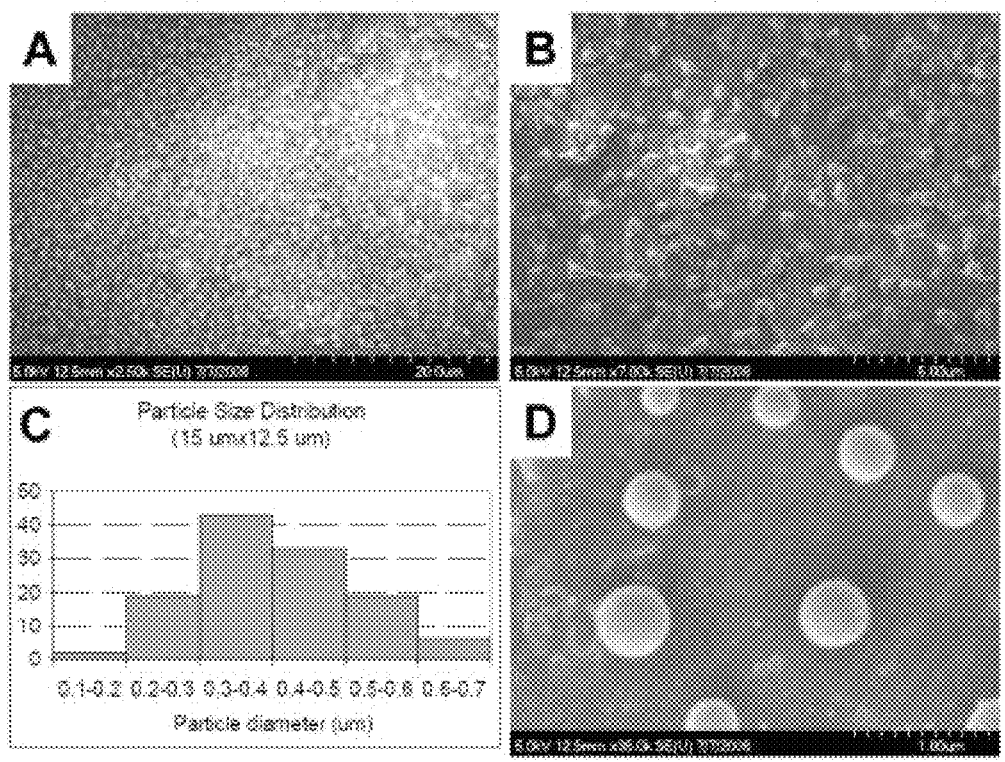
FIG. 6, panels A-D, shows a method of forming nanoparticles on a surface by heating a thin film (e.g., using a pulsed laser) to form annealed particles. In this example, a 30 nm gold film with 2 nm titanium adhesion layer was heated with a pulsed laser (532 nm, 6 ns) at 113.2 mJ/cm$^2$ for 100 pulses. Particle size ranged from 0.1 to 0.7 µm (see, e.g., panel C). Particle density was about 0.65 particle/µm$^2$=65 particle per cell (assuming cell area-10 µm×10 µm).

In another approach to it was discovered that heating a thin film on a substrate or micropipettete, e.g., using a pulsed laser, can anneal the thin film into disperse nanoparticles. Thus, as illustrated in FIG. 6 fabrication can involve depositing a layer of adhesion metal (e.g. titanium, chromium) followed by a layer of gold (or other metal) film on glass, or plastic, or quartz, etc. substrates. The sample is then heated (e.g., irradiated with laser pulses). At high enough laser energies, the metal films melt, and the molten metal condenses to form beads-like particles (as seen in SEM images in FIG. 6) on the substrate or micropipettete.

The optional adhesion metal (e.g., titanium) layer sandwiched between the substrate and the gold layer provides a stronger adhesion of the gold film as well as the gold beads after annealing to the substrate. In the absence of the adhesion layer, gold can still be annealed into nanoparticle beads on the surfaces by laser pulses or other heating methods.

In another approach a substrate or micropipetteis provided bearing a thin film. The thin film is then etch away to leave nanoscale size domains that can be heated by applying a laser or other energy source.

The particle array fabrication method(s) can be extended to other micro or nanofabrication techniques such as nanoimprint, e-beam lithography, and others. The current plastic substrate can be replaced with other polymer materials such PDMS or a glass substrate, or a silicon substrate, or others.

The methods of making and attaching particles and nanoparticles to the surface or forming thin films on a surface described above are illustrative and not intended to be limiting. Using the teachings provided herein, other particles, nanoparticles, and thin film coated surfaces can be produced using at most routine experimentation.

Integration with Optical Tweezers.

Conventional microinjection in non-adherent cells is a laborious process since it requires using another holding pipette to apply suction and stabilize the cell. This way the cell has an anchorage to counteract the force exerted by the injection pipette as the pipette penetrates the cell membrane. The suction pressure, relative positioning of the injection pipette and holding pipette can attribute to severe cell damage and death to fragile cells. One current way to increase the microinjection efficiency of non-adherent cells is to bond them on a substrate with treated surface before injection and later on release them from the substrate. This method not only introduces extra chemical treatments to cells and is also time consuming. Optical tweezers have been shown to trap and manipulate micron- and even submicron-sized objects and biological contents. The trapping force of optical tweezers is typically on the order of piconewtons. As a result, it is generally not possible to use optical tweezers to anchor the non-adherent cells during conventional glass microcapillary injections.

The plasmonic photothermal pipette (single surgery tool of this invention), on the other hand, can readily be combined with optical tweezers. In this case, the manipulated cells are self-aligned to the injection position by the optical forces. During the injection process, cells experience minimal sheer force and mechanical distortion which are two critical parameters to keep the injected cells alive. The optical tweezers integrated laser cell surgery technique has the potential to achieve high speed and high efficiency microinjection for non-adherent cells.

Cell Types

Generally the methods and devices described herein can be used with essentially any cell having a cell membrane. In addition, the methods and devices can also be used on cells having a cell wall.

Thus, for example, adherent cells including NIH3T3 mouse fibroblasts, HEK293T embryonic kidney fibroblasts, and HeLa cervical carcinoma cells have been injected GFP-expressing plasmids using the devices and methods described herein. In general, it is believed that any adherent mammalian cell type can be easily injected using the devices and methods described herein because: 1) the laser fluence that is determined as optimal in terms of effective hole-punching and maintaining cell viability is lies with in a relatively narrow range for all the cell types tested; and 2) adherent cell features used to determine appropriate injection location (e.g., perinuclear or possibly nuclear) are easily identified visually.

Lymphocytes, stem cells of various types, germ cells and others are non-adherent, but it is often desirable to inject or perform other "surgical" procedures on such cells. Integration of optical tweezers with the cell surgery tool as described herein, makes this possible.

In addition, using the methods and devices described herein, injecting individual cells within a cell cluster, such as is required to grow human embryonic stem cells and maintain pluripotency, is achievable especially on the surface of stem cell clusters using the methods and devices described herein. It is also believed to be possible to stereotactically inject specific cells within clusters, which is desirable for a variety of reasons (e.g., developmental tracking, establishing gradients, etc.).

Deliverable Materials.

It is believed possible to deliver essentially any desired material into a cell using the methods and devices described herein. Such materials include, but are not limited to nucleic acids, proteins, organelles, drug delivery nanoparticles, probes, labels, and the like. Delivery of plasmid DNAs into cells using the methods described herein as been demonstrated already in at least three adherent cell types. Accordingly any plasmid-sized genetic material should be easily transferred by the methods and devices described herein.

BACs (bacterial artificial chromosomes)—a desired goal for hard to transduce cells and for delivery vehicles with size restrictions (plasmids, retroviruses, lentiviruses) for introducing large genetic anomalies or for tracking the regulated expression of specific genes during development.

Accordingly, it is believed the devices and methods described herein can be used to deliver whole or partial natural or synthetic chromosomes. Similar to BACs, large chromosomes or chromosomal fragments that cannot be transduced into most cell types by previous methods could be transferred into cells by our methods, for example, to establish models of human trisomy disorders (e.g., Down and Klinefelter syndromes).

Similarly the methods can be used for the transfer of nuclei (e.g., in somatic nuclear transfer), or other organelles (e.g., mitochondria, or nanoengineered structures) can readily be introduced into cells.

In various embodiments the deliverable materials comprise a reagent includes, but is not limited to a reagent selected from the group consisting of nucleic acids (including, for example, vectors and/or expression cassettes, inhibitory RNAs (e.g., siRHA, shRNA, miRNA, etc.), ribozymes, proteins/peptides, enzymes, antibodies, imaging reagents, organelles (e.g., nuclei, mitochondria, nucleolus, lysosome, ribosome, etc.), chromosomes, intracellular pathogens, inanimate particles, such as quantum dots, surface-enhanced, Raman scattering (SERS) particles, microbeads, and the like.

Modular Systems.

In certain embodiments the substrates (transfection substrates) are provided as a "module" that can readily be integrated with existing equipment. For example, in certain embodiments, the transfection substrate is provided in a format that can be added to or that can replace a stage on an existing microscope. In certain embodiments the substrate is formatted to replace and x/y/z stage on an inverted microscope (e.g., a Zeis inverted microscope).

In certain embodiments the transfection substrates are provided as a microfluidic system (e.g., a lab on a chip system) and/or as a module that can be integrated with microfluidic systems.

Cell Surgery Systems and Patterned Transfection Systems.

In various embodiments this invention contemplates systems for cell surgery or patterned transfection of cells. In certain embodiments the cell surgery systems comprise a microsurgery tool as described herein and a micromanipulator and/or positioner to precisely position the tool, e.g., with respect to a cell. The systems can, optionally, further comprise means for holding cells (e.g., pipettes or other manipulators), means for delivering fluids and/or gases or devices into a cell through the surgical tool, means for removing fluids, organelles, etc., from the cell through the tool, and the like. In certain embodiments the systems can further comprise a viewing system (e.g., a microscope), data/image acquisition systems, and computer control systems for controlling the viewing system, micromanipulators, data/image acquisition systems, and the like.

Similarly, in various embodiments patterned transfection systems comprise a cell transfection substrate (e.g., a culture vessel comprising one or more surfaces bearing particles, nanoparticles, and/or thin films as described herein). The substrate typically bears cells and/or a cell culture. The system can optionally comprise means for delivering reagents, agents to be transfected into the cell(s), means for masking portions of the substrate from an electromagnetic energy source, and the like.

In certain embodiments the systems optionally further include a source of electromagnetic energy to heat the particles, nanoparticles and/or thin film on the surgical tool or transfection substrate. Suitable sources include, but are not limited to a laser, a magnetic field generator, an RF field generator, and the like.

In various embodiments the systems can include a controller (e.g., a laser controller). The controller can be configured to control the intensity and/or duration and/or wavelength of an illumination source and/or the pattern of illumination of the microsurgery tool and/or the transfection substrate. In certain embodiments the controller detects and/or controls flow of reagents through microchannels comprising the transfection substrate and/or a microfluidic system within which the transfection substrate is disposed. Where the transfection substrate is provided on a microscope (e.g., an inverted microscope) the controller can, optionally control the microscope stage, the microscope focus, and/or image acquisition from the microscope. In certain embodiments the controller optionally controls filling of the microcapillary (comprising the microsurgery tool), and/or angle of the microsurgery tool with respect to the cell surface and/or with respect to the illumination, and/or motion of the microsurgery tool, and/or operation of the microcapillary to inject reagents into the cell. In certain embodiments the controller coordinates action of the microsurgery tool with illumination of the tip by the energy source.

Kits.

In another embodiment, this invention provides kits for performing single-cell surgery or patterned delivery of an agent into a cell (patterned transfection). In certain embodiments the kits comprise a container containing a single cell surgery tool and/or a transfection substrate as described herein. In various embodiments the kits can optionally additionally include any of the reagents or devices described herein (e.g., reagents, buffers, tubing, indicators, manipulators, etc.) to perform single surgery and/or patterned transfection of cell(s).

In addition, the kits optionally include labeling and/or instructional materials providing directions (i.e., protocols) for the use the surgery tool and/or patterned transfection substrate (e.g., practice of the methods) of this invention. In certain embodiments the instructional materials describe the use of the cell surgery tools described herein to inject or remove materials, and/or to manipulate components of a cell and/or the use of the transfection substrate to deliver one or more agents into a cell.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Fabrication and Use of a Cell Surgery Tool

This example pertains to a novel cell surgery device that integrates nanoparticle photothermal effects with microcapillary techniques. Proof-of-concept experiment results are presented here. The conventional microcapillary technique is a versatile tool for performing single cell recording and manipulations. However, it introduces enormous stress to the cell as the microcapillary punctures through the cell membrane. As a result, this procedure often results in cell death, particularly on small or mechanically fragile cells.

Current cell surgery methods using laser ablation (Vogel et al. (2005) *Appl. Phys. B-Lasers O.*, 81(8): 1015-1047) eliminate the mechanical stress but they require tightly focused light and precise positioning of the injection micropipetteat the laser focal spot. The cell surgery device we described in this example, utilizes photothermal effects of nanoparticles on the tip of a microcapillary pipette. Laser-induced heating of the nanoparticles creates transient holes in the cell membrane as the pipette encounters the cell. Since the heating only occurs at the membrane area in contact with nanoparticles, this device can operate with non- or lightly-focused laser. This way unwanted stress is minimized. Possible chemical effects due to strong laser intensity are avoided to ensure the biology of the manipulated cells under study is unaffected.

FIG. 1 shows a schematic of the cell surgery tool. Gold nanoparticles are coated onto the tip of a micropipettte. Noble metal nanoparticles strongly absorb electromagnetic waves with a frequency close to its surface plasmon frequency, usually in the visible and NIR range (Hartland (2006) *Annu. Rev. Phys. Chem.*, 57: 403-430). For example, 30 nm diameter gold nanospheres show a peak at wavelengths around 532 nm in their extinction spectrum. Upon laser pulse excitation, the nanoparticles rapidly heat up due to the absorbed energy, causing superheating and evaporation of the surrounding medium. This direct heating or cavitation force from the collapsing vapor bubbles lead to increase in cell membrane permeability or "holes punching" in the membrane. The damage volume can be controlled by laser pulse fluence and nanoparticle size. It has been shown that the heated volume extends tens of nanometers from the surface of a 30 nm gold nanosphere, and the nanoparticle cools down to equilibrium temperature within few nanoseconds after laser pulsing (Pitsillides et al. (2003) *Biophys. J.*, 84: 4023-4032, 2003; Kotaidis et al. (2006) *J. Chem. Phys.*, 124(18), Art. No. 184702). As a result, the rest of the membrane or cell does not have sufficient time to respond and remains mechanically undisturbed. This way a micropipette can penetrate the cell membrane with ease and cell damage is minimized.

Experiment and Results.

Synthesis of Gold Nanorods

Figure 4:
FIG. 4 shows TEM images of aspect ratio 3.2 (A:24 hr) and 5.8 (C:72 hr).
Figure 4:
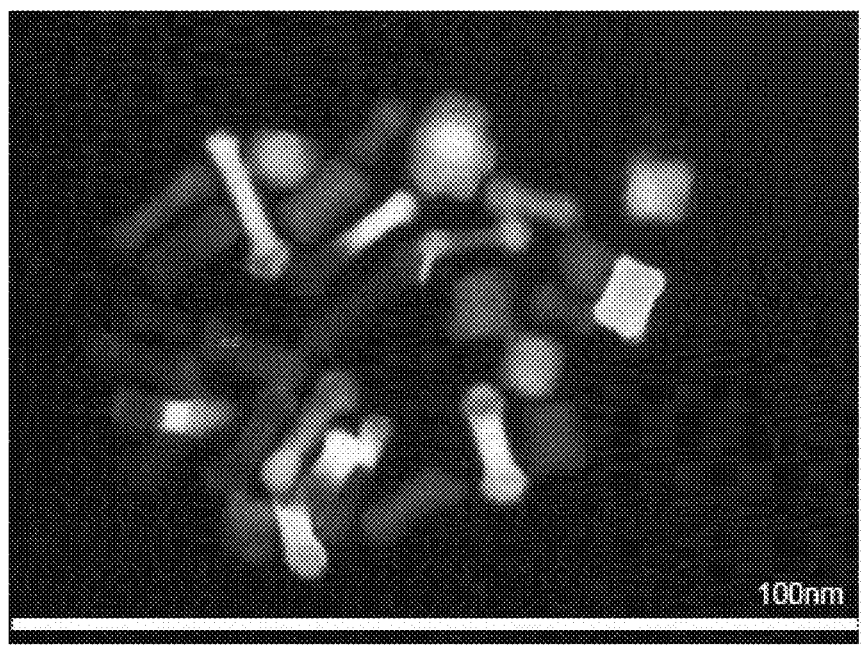

In various embodiments the synthesis of nanorods can be achieved either through the use of rigid templates or surfactants. For our application, we employed the surfactant route for the relatively facile synthetic methods. Briefly, the nanorods synthesized were created via seed mediated growth, developed by Jana et al. (2001) *J. Phys. Chem. B*, 105(19): 4065-4067, where a 3-4 nm seed added to a growth solution and aged, in the presence of surfactants, to yield nanorods with unique aspect ratios. In addition to surfactant concentration, the aspect ratios have been shown to be controlled by the addition of specific amounts of silver ion (Nikoobakht and El-Sayed (2003) *Chem. Mater.* 15(10): 1957-1962). The resulting nanorod solutions were characterized via TEM on carbon-coated copper grids. FIG. 4 shows the synthesized nanorods with two aspect ratios of 3.2 and 5.8.

Synthesis Process

Benzyldimehtylammoniumchloride hydrate (BDAC), hexadecyltrimethylammonium bromide (CTAB), L-ascorbic acid, silver nitrate (AgNO3) sodium borohydride (NaBH4), hydrogen tetrachloroaurate (HAuCl4-3H2O) were obtained from Sigma Aldrich. Deionized water (18 M) was used throughout the experiments.

Seed Solution:

5.0 ml of 0.20 M CTAB was mixed with 5.0 ml of 0.0005 M $HAuCl_4$ with stirring at 25° C. 0.60 ml of ice-cold 0.01 M $NaBH_4$ was added to the mixture. The resulting solution turned brownish-yellow, from the reduction of gold. The resulting solution was stirred vigorously for two minutes to ensure all the Au had been reduced to $Au^0$.

Growth Solution:

20.0 ml of 0.15 M BDAC, and 0.40 g CTAB were combined and sonicated for 20 min at 40° C., to dissolve the CTAB completely. To four separate vials, 200 µl of 0.004 M $AgNO_3$ was dispensed followed by 5 ml BDAC/CTAB surfactant solution. This produced four different growth solutions, to be aged variably. The growth solution exhibited an orange tinge. To each vial, 5.0 ml of 0.0010 M $HAuCl_4$ was added and gently mixed, followed by 70 µl of 0.0778 M L-ascorbic acid. The orange tinge disappeared during the reduction of $Au^{3+}$ to $Au^0$. 12 µl of the seed solution was added to each vial. This produced a reddish color, which points to the reduction of at least 60% of the Au. The resulting solutions were aged for 1 hr, 24 hr, 48 hr, and 72 hr.

The seed Au was directly grown on the glass and followed by dipping the pipette in the growth solution to make the Au particles bigger.

Use of Cell Surgery Tool.

Figure 2:
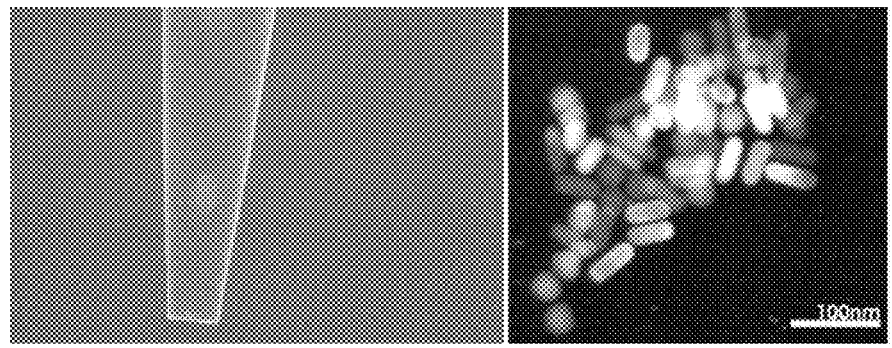
FIG. 2 shows an SEM image of glass micropipette coated with carbon (left panel) and a TEM image of synthesized gold nanoparticles (right panel).

In experiments described here, a pulsed laser with wavelength of 532 nm and pulse duration of 5 nanoseconds was used. The laser delivered a fluence of 883 $J/m^2$ onto a non-focused spot of 5×3 $mm^2$. Gold nanoparticles were synthesized directly on glass microcapillaries (FIG. 2) using the method reported by Xu et al. (2004) *Chem. Mater.*, 16(11):2259-2266. Nalm-6 cells (human B cell precursor leukemia) cultured in RPMI were used. Highly localized transient openings of the cell membrane were generated by the photothermal effect of nanoparticles on glass micropipettes, with the dimension of a typical opening close to the micropipette tip size, around 2 µm (FIG. 3C). The cell remained viable after the procedure. A control experiment using a glass micropipette of the same size without gold nanoparticles was also performed. The cell membrane restored its shape instantaneously and showed no sign of hole opening after laser pulsing. We also investigated the laser-induced photothermal effect of an electrically and thermally conductive amorphous carbon coating. A thin film of amorphous carbon was sputtered onto a glass micropipettte. Experimental results showed explosive effects extending over a large volume that lysed and killed the cell instantly under the same laser influence (FIG. 3B).

Conclusion

This example shows a novel cell surgery tool utilizing photothermal effects of metal nanoparticles and provides a proof-of-concept experiment. Localized and transient hole opening on the cell membrane is accomplished using a gold-nanoparticles-coated micropipette compared to instantaneous cell lysing and killing by amorphous carbon coated micropipettte.

Example 2

Plasmid DNA Transfection and Expression

Figure 11:
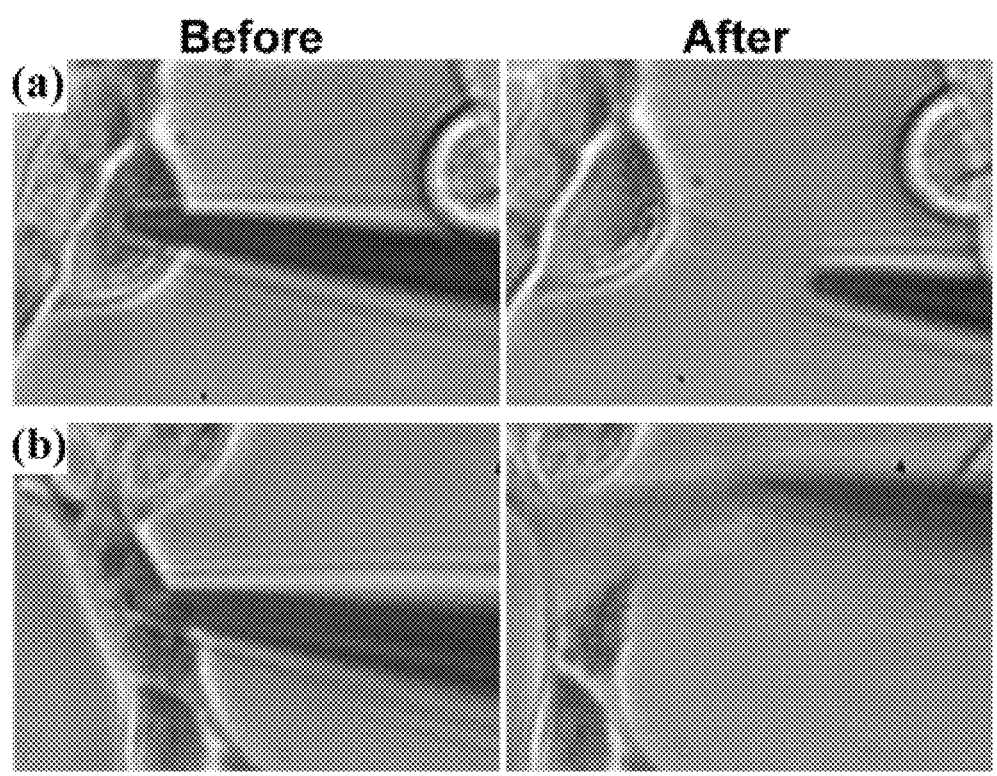
FIG. 11 shows preliminary photothermal pipette tests on 293T cells. Before (left column) and after (right column) laser pulsing. Pipettes were coated with Au/Pd thin films of different thickness. Film thickness=5 nm (panel a) versus 13 nm (panel b). The laser fluence used in both experiments was 88.3 mJ/cm$^2$.

We have demonstrated hole-opening on cell membranes using our plasmonic photothermal pipettes. In the experiments described here, a Q-switched, frequency-doubled Nd:YAG pulsed laser with wavelength of 532 nm and a pulse duration of 6 ns was used (Continuum Minilite I). The laser delivered a fluence of 88.3 $mJ/cm^2$ onto a non-focused spot of 11.8 $mm^2$. Gold/palladium thin films were deposited onto the glass micropipettetes via sputtering. Human embryonic kidney HEK293T cells cultured in DMEM were used. Disruption of the cell membrane was generated by the photothermal effect of the Au/Pd thin film on glass micropipettetes. With a film thickness of 5 nm, the dimension of the membrane opening was close to the micropipette tip size, around 2 µm (see, e.g., FIG. 11, panel a). For a film with 13 nm thickness, explosive effects extending over a large volume lysed and killed the cell instantly under the same laser fluence (FIG. 11, panel b). A control experiment of using a glass micropipette of the same size without coating was also performed. The cell membrane showed no sign of hole opening or damage after laser pulsing.

Figure 12:
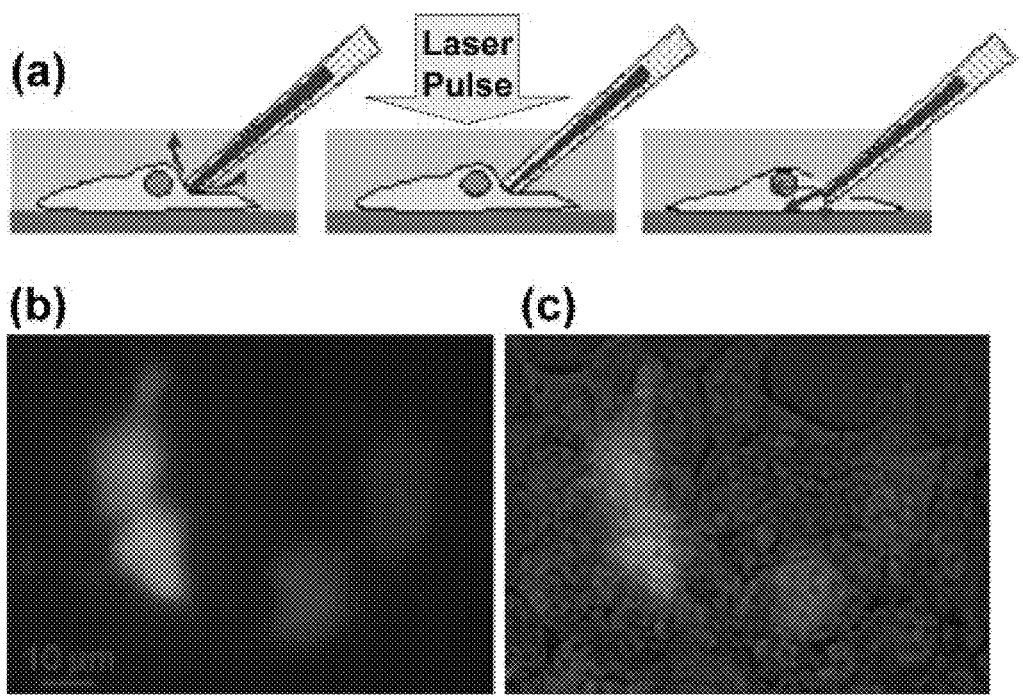
FIG. 12, panels a-c, show microinjection of GFP-encoding plasmids into adherent 293T cells using gold thin-film coated pipette. Panel a: Microinjection procedure, Panel b: A fluorescent image of cells 24 hours after injection, showing cells viable and expressing GFP; Panel c: An image overlaying the phase contrast and the fluorescence images.

We have also demonstrated microinjection of green fluorescence protein (GFP) encoding plasmids into HEK293T cells. The plasmid is a circular strand of DNA, which upon injection into the cell would allow the cell to produce GFP and fluoresce green. FIG. 12, panel a, shows the microinjection procedure. A continuous flow of plasmids-containing buffer was ejected out of the pipette tip as the photothermal pipette came to a gentle contact with the cell membrane. After applying the laser pulse, the buffer intercalated throughout the cell and the pipette was immediately moved away from the cell. The injected cells were viable 24 hours after the injection and expressed GFP. A separate control experiment was conducted where the pipette ejected out a stream of buffer containing plasmids while in contact with the cell membrane without applying the laser pulse. No cells expressing GFP were found 24 hours later. This is a direct proof that the plasmonic photothermal pipette successfully opened a hole on the cell membrane, which allowed plasmids to flow in. Also the cell survived the procedure and remained viable 24 hours later.

Example 3

Integration with Optical Tweezers

Figure 13:
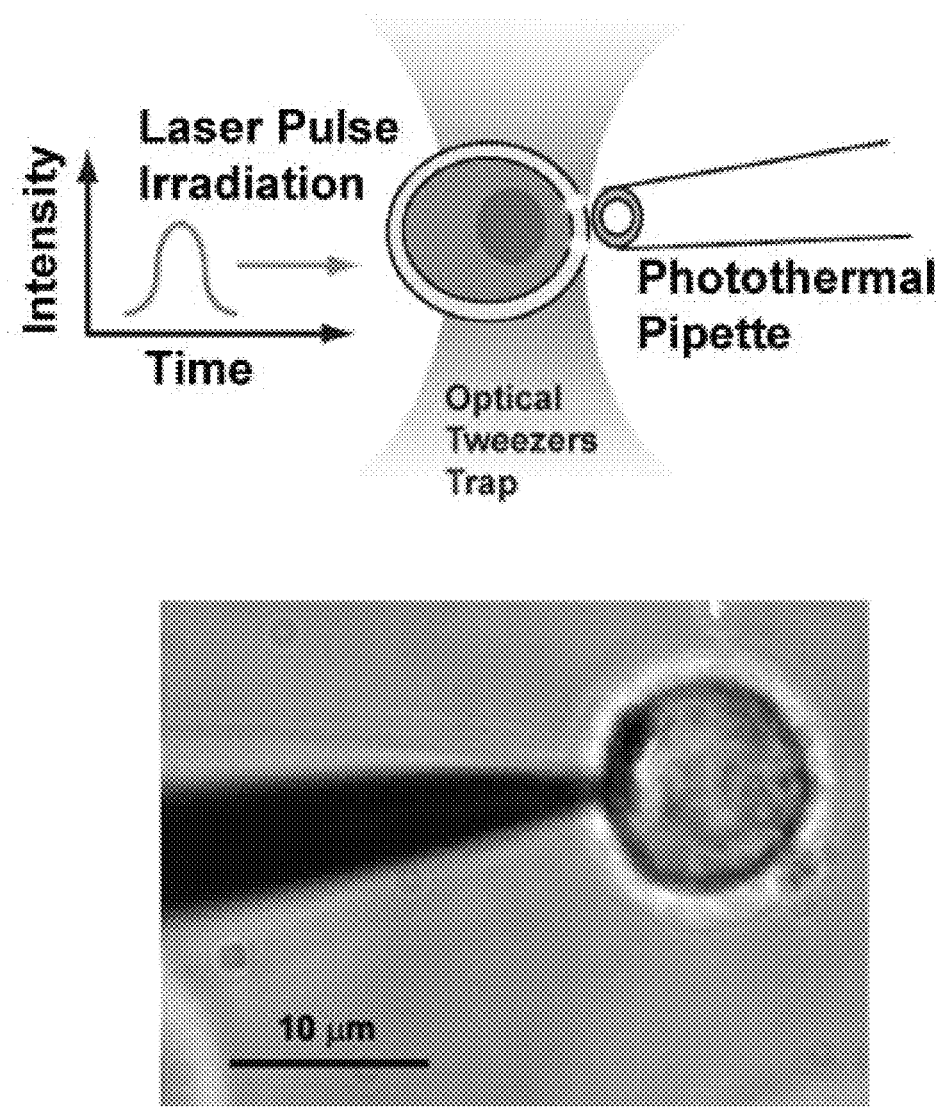
FIG. 13 shows a schematic of non-adherent cell microinjection using plasmonic photothermal pipette combined with optical tweezers (top panel) and an image showing a Nalm-6 cell trapped by optical tweezers while in contact with the photothermal pipette tip (bottom panel).

Shown in FIG. 13, a Nalm-6 cell is trapped by a 50 mW, 1064 nm laser beam at the focal point of a N.A. 1.3 100× oil immersed lens while in contact with the photothermal pipette tip. This optical tweezers is constructed on the same Zeiss inverted microscope used for taking time-resolved images of photothermal cell surgery process. This gives us an integrated optical system capable of performing optical trapping, cell surgery, and time-resolved imaging simultaneously. Since the photothermal pipette relies on the nanobubble explosion to open a hole on the plasma membrane, the pipette tip only needs to be in gentle contact with the cell. In this case optical tweezers provide sufficient trapping force to hold the cell in place during the procedure. Besides minimizing the contact force applied on the cell from both the holding and injection pipettes, another advantage of incorporating optical tweezers is the ease of selecting, trapping and releasing the cell during manipulation.

Example 4

Light Image Patterned Molecular Delivery into Live Cells Using Gold Particle Coated Substrate Optoporation, a method for molecular and gene delivery into cells, utilizes a tightly-focused, pulsed laser beam to create pores in the cell membrane (Vogel et al. (2005) *Appl. Phys. B-Lasers O.*, 81(8): 1015-1047). It allows for contact-free delivery, and with the use of a femtosecond laser, 100% transfection efficiency targeted at single cells has been demonstrated (Tirlapur and Konig (2002) *Nature* 418: 290-291). One drawback of this approach is that in order to obtain site-specific or patterned cell transfection, the laser beam must scan through every cell, which would be time consuming when large-scale, patterned cell transfection is desired, such as in complex tissues.

Another contact-free method of increasing cell membrane permeability is to use light-absorbing micro- or nanoparticles (Pitsillides et al. (2003) *Biophys. J.* 84: 4023-4032). Upon irradiation by a short pulse laser, the particles create transient and localized explosive bubbles, that disrupt part of cell membrane adjacent to these particles and leaves the remaining cell structure intact. By controlling the particle size, density and the laser fluence, cell permeablization and transfection can be achieved with high efficiency (Yao et al. (2005) *J. Biomed. Optics*, 10(6): 064012).

Here we describe a simple device that can spatially select and target cells for molecular delivery by light image patterning. Our approach has the potential of achieving large-scale, image-based molecular and gene delivery of defined pattern into specific cells within complex monolayer mixtures.

Principle and Device Structure

Figure 7:
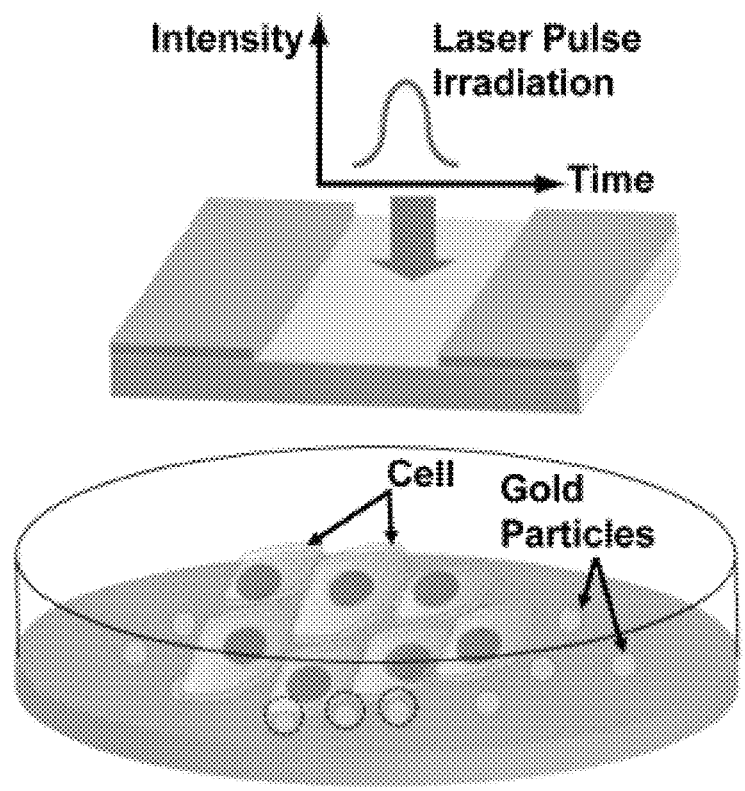
FIG. 7 illustrates a schematic of one embodiment of a device capable of light-patterned molecular delivery using a gold particle coated substrate.

In certain embodiments the device consists of a plastic substrate with particles (e.g., gold particles) immobilized on the surface (see, e.g., FIG. 7). Cells are seeded on this substrate, e.g., until a confluent culture forms. A pulsed laser irradiates a shadow mask and the corresponding illumination pattern is imaged onto the substrate. In the area exposed to the pulsed laser, gold particles are heated to high temperatures due to the absorbed optical energy. Within a few nanoseconds, the heat is dissipated to the thin liquid medium layer surrounding the gold particles, which generates explosive vapor bubbles (Kotaidis et al. (2006) *J. Chem. Phys.*, 124: 184702). The rapid expansion and subsequent collapse of the vapor bubbles give rise to transient fluid flows that induce strong shear stress on the adherent cell causing localized pore formation in the cell membrane. As a result, membrane-impermeable molecules can be carried into the cell by fluid flows or thermal diffusion. Since the cavitation bubble only takes place where the gold particle is exposed to the laser, an optical pattern can be designed to address molecular uptake in specified areas of the cell culture. This way high-throughput, spatially-targeted molecular delivery is made possible by controlling the gold particle size, density on the substrate, and the excitation laser fluence.

Experiments and Results

Figure 8:
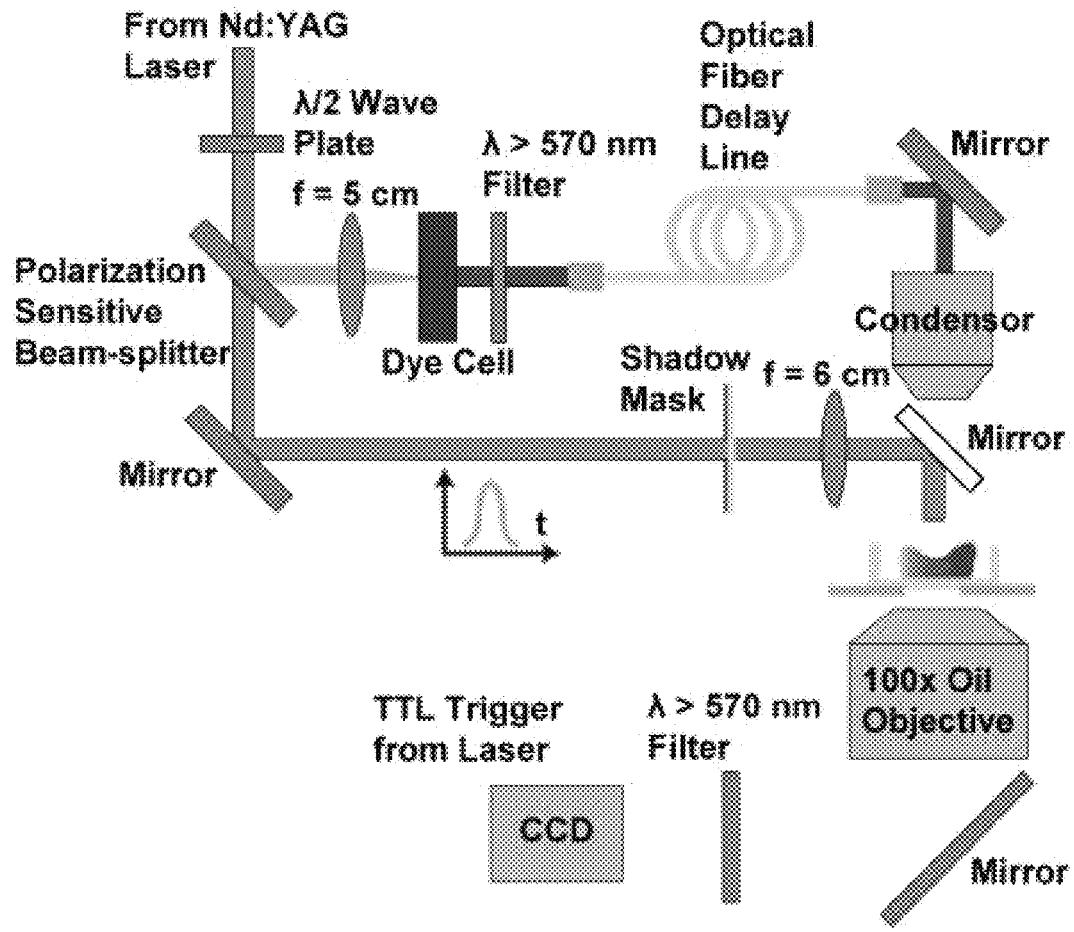
FIG. 8 illustrates a schematic of an experimental setup for light-patterned molecular delivery and a time-resolved imaging system used to capture the cavitation bubble dynamics.

In one experiment, 0.6 µm gold nanospheres (Bio-Rad) were bombarded onto a plastic petri dish using a biolistic injector at 2200 psi bombardment pressure (Bio-Rad, PDS-1000). Immortalized human embryonic kidney cells, (HEK293T) cultured in DMEM were then plated in the dish and incubated overnight until about 70-80% cell confluence was reached. A Q-switched, frequency-doubled Nd:YAG laser at 532 nm in wavelength (Continuum, Minilite I) was used to irradiate the device. The laser has a pulsewidth of 6 nanoseconds and a spot size of 9.4 mm$^2$. A shadow mask was placed in the beam path to cast the desired optical pattern, which was imaged onto the device at 0.83× reduction. The induced cavitation bubbles from the gold particles were captured using the time-resolved imaging system depicted in FIG. 8. A high-speed Intensified CCD camera (Princeton Instrument, PI-MAXII) provided exposure times as short as 500 ps. A nanosecond time delay between the captured bubble image and the excitation laser pulse was controlled by the length of an optical fiber delay line. During laser pulsing, cells were immersed in a medium containing the membrane-impermeable fluorescent dye Calcein (Invitrogen, mol wt 622.5) at 1 mg/ml. After cavitation induction, the cell culture was washed with phosphate buffered saline and re-immersed in fresh medium before checking fluorescence staining.

Figure 9:
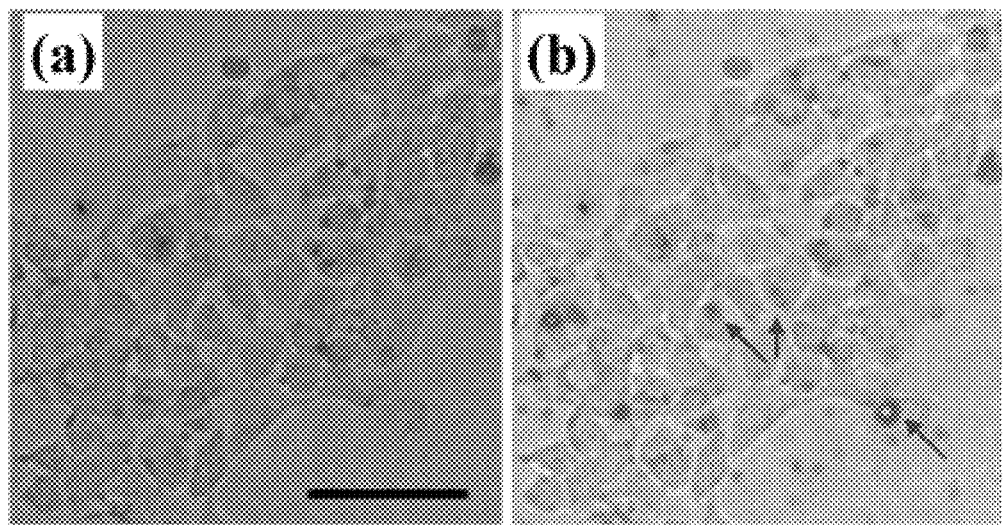
FIG. 9 shows bubbles induced by pulsed laser irradiation on the gold particles. (a) Before the laser pulse (b) 78 ns after the laser pulse. Bar=50 µm.
Figure 10:
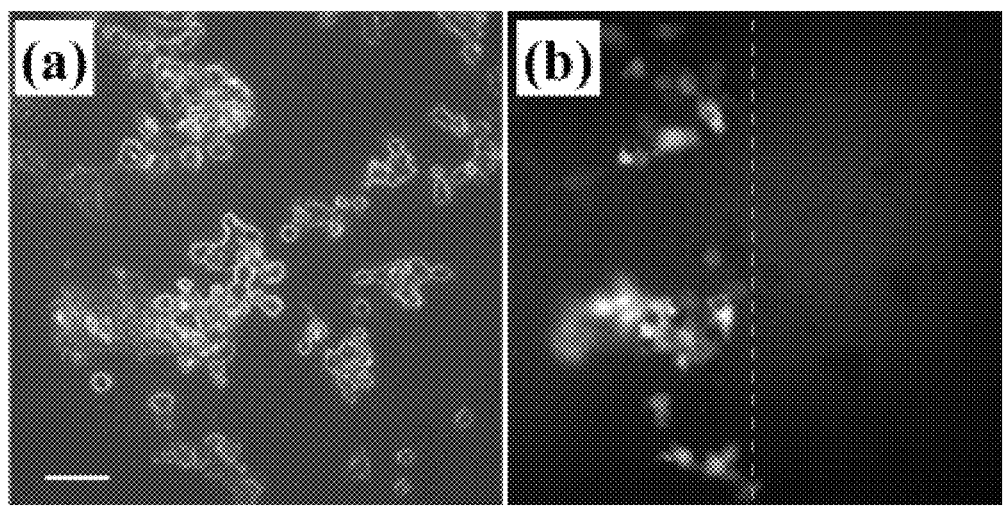
FIG. 10 shows light-patterned fluorescence dye uptake in HEK293T cells using a shadow mask. (a) Bright field (b) Fluorescent image (mask covered the side to the right of the dash line.

FIG. 9 shows the cavitation bubbles induced by heated gold particles 78 nanoseconds after the laser pulse without a shadow mask. The density of the particles is about 0.004 particles/µm$^2$. This corresponds to about 0.9 bubbles per cell (assuming the area of a HEK293T cell is ~15×15 µm). In FIG. 10, a shadow mask was used and only the left half of the device was irradiated with the laser pulse (dashed line corresponds to the shadow mask boundary). Laser fluence was 128.2 mJ/cm² and 7 pulses were applied. The fluorescent image clearly shows that the dye uptake pattern coincides with the lighted area.

Conclusion

A device capable of light-patterned molecular delivery is described here. Successful delivery of fluorescent molecules was demonstrated in adherent cell culture. The targeted delivery area was controlled by a shadow mask. This device has the potential to achieve large-scale, light-patterned molecular and gene delivery in living cells.

Example 5

Parallel Delivery of Reagents to Target Cells

We developed another parallel delivery platform by integrating light-absorbing metallic nanostructure on microfluidic structures (see, e.g., FIG. 14). The illustrated device consists of arrays of microfluidic orifices with titanium coating on the sidewall. The orifices are connected to a network of microfluidic channels underneath. Upon laser pulsing and cell membrane opening, suspended cargo in the microfluidic channel can be actively delivered into the cells on top of the orifices by pumping the fluidic through an external pressure source.'

Figure 19:
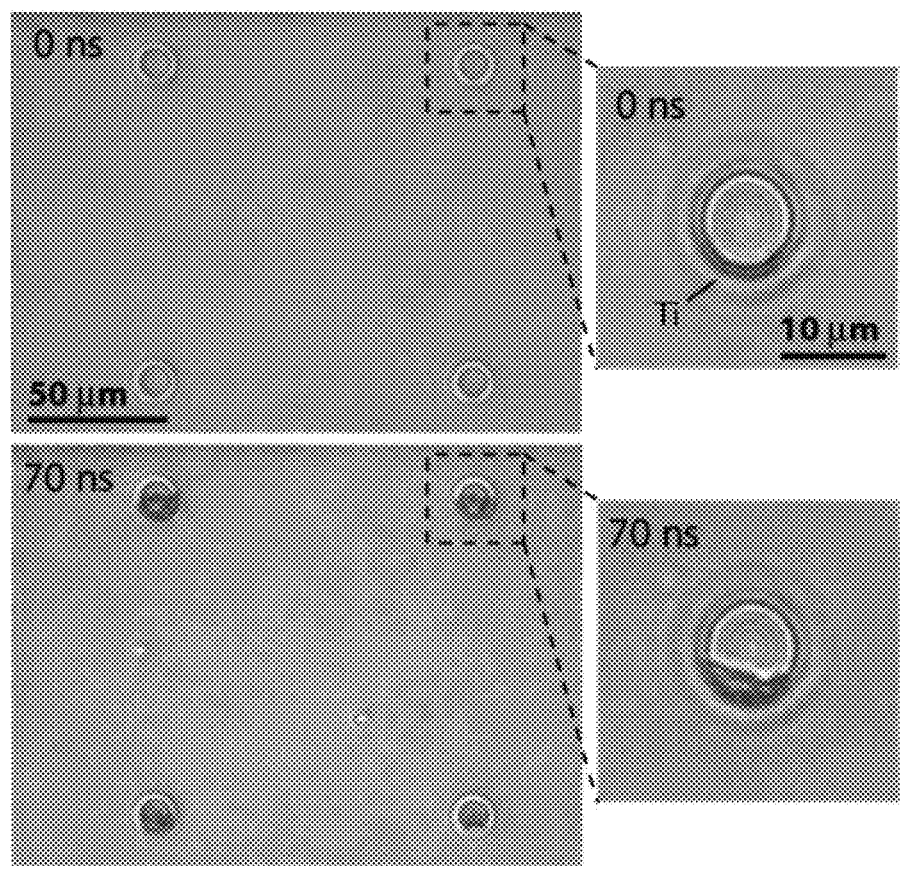
FIG. 19 illustrates parallel bubble excitation on a reagent delivery substrate. By irradiating the structure with a laser pulse (6 ns in pulsewidth and 532 nm in wavelength), the bubbles were synchronously generated in each of the circular openings. Due to the new-moon-shaped Ti thin film coating, the bubble explosion took place only along parts of the cylindrical sidewall.

Parallel bubble excitation was tested on the device. By irradiating the structure with a laser pulse (6 ns in pulsewidth and 532 nm in wavelength), the bubbles were synchronously generated in each of the circular openings. Due to the new-moon-shaped Ti thin film coating, the bubble explosion took place only along parts of the cylindrical sidewall (see, e.g., FIG. 19).

Figure 20:
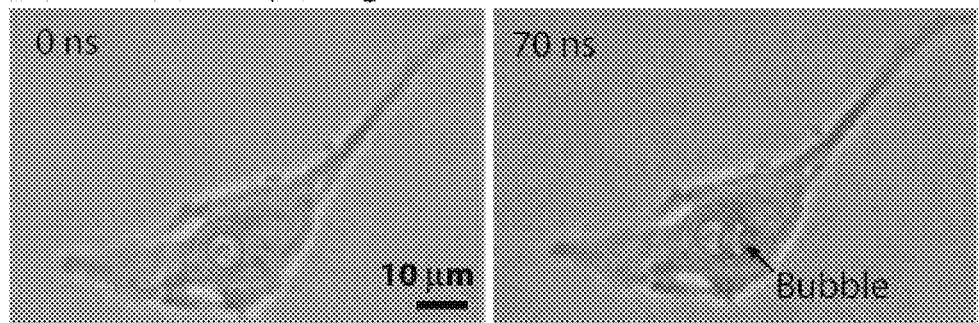
FIG. 20, panels A and B, illustrate membrane opening (panel (a)) and the use of a reagent delivery substrate to deliver a test reagent to HeLa cells (panel (b)). Membrane-impermeable green-fluorescent FITC-dextran (molecular weight=3 k Da.) was loaded in the cell culture media at a concentration of 200 µg/ml. After laser pulsing at 156 mJ/cm$^2$ fluorescent dye uptake was observed in the cell grown on top of the circular orifice and subjected to laser-triggered bubble explosion. Here the delivery is through passive diffusion.
Figure 20:
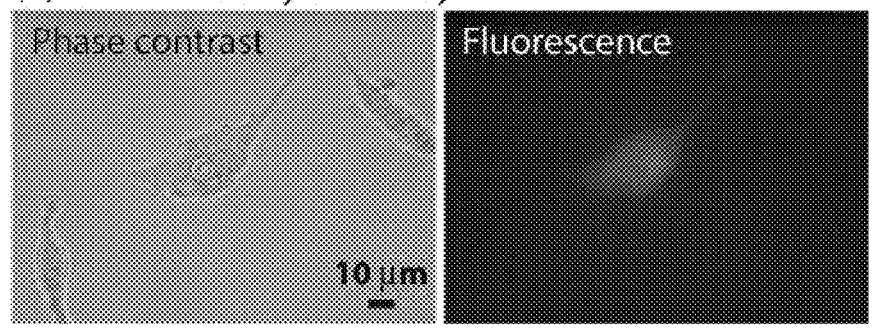

To test cell membrane opening and cargo delivery, HeLa cells were seeded onto the device. Cells grew and divided on top of the SU-8 substrate and orifices as usual. Membrane-impermeable green-fluorescent FITC-dextran (molecular weight=3 k Da.) was loaded in the cell culture media at a concentration of 200 µg/ml. After laser pulsing at 156 mJ/cm², fluorescent dye uptake was observed in the cell grown on top of the circular orifice and subjected to laser-triggered bubble explosion (see, e.g., FIG. 20). Here the delivery was through passive diffusion.

Example 6

Photothermal Nanoblade for Large Cargo Delivery into Mammalian Cells

It is difficult to achieve controlled cutting of elastic, mechanically fragile, and rapidly resealing mammalian cell membranes. In this example, we describe a photothermal nanoblade that utilizes a metallic nanostructure to harvest short laser pulse energy and convert it into a highly localized explosive vapor bubble, which rapidly punctures a lightly contacting cell membrane via highspeed fluidic flows and induced transient shear stress. The cavitation bubble pattern is controlled by the metallic structure configuration and laser pulse duration and energy. Integration of the metallic nanostructure with a micropipette, the nanoblade generates a micrometer-sized membrane access port for delivering highly concentrated cargo ($5\times10^8$ live bacteria/mL) with high efficiency (46%) and cell viability (>90%) into mammalian cells. Additional biologic and inanimate cargo over 3 orders of magnitude in size including DNA, RNA, 200 nm polystyrene beads, to 2 µm bacteria have also been delivered into multiple mammalian cell types. Overall, the photothermal nanoblade is an effective approach for delivering difficult cargo into mammalian cells.

Figure 21:
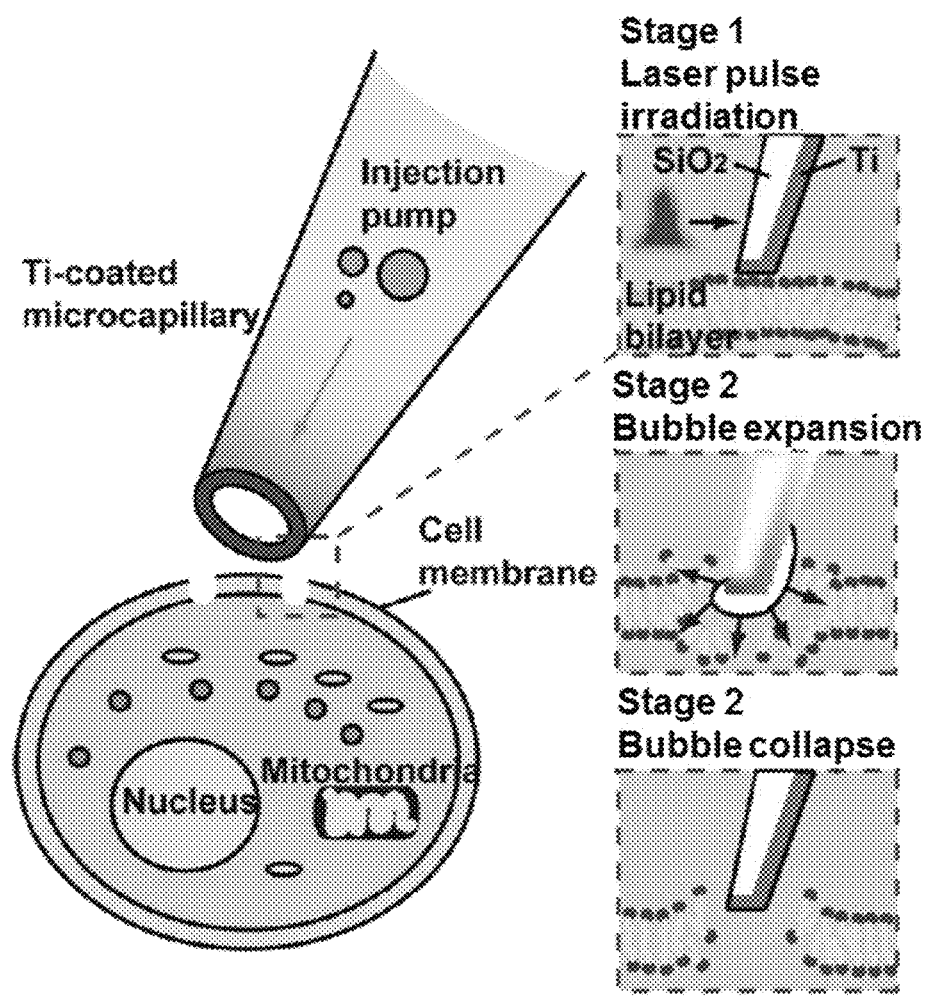
FIG. 21 illustrates the ultrafast membrane cutting mechanism using a photothermal nanoblade for cargo delivery into live mammalian cells. A Ti thin film coats the outside of a glass micropipettete. Upon excitation by a nanosecond laser pulse, the Ti heats rapidly, along with a thin surrounding aqueous layer through heat conduction. An explosive vapor nanobubble that expands and collapses in <1 µs locally cuts the contacting cell membrane in synchronization with pressure-driven delivery of the microcapillary contents.

This example pertains to a photothermal nanoblade that is a metallic nanostructure integrated with a microcapillary pipet (FIG. 21). The photothermal nanoblade harvests optical pulse energy to trigger spatially patterned, temporally synchronized cavitation bubbles that generate high-speed, localized fluidic flows. If a soft material or fragile structure, such as a cell membrane, is in contact with the photothermal nanoblade, the ultrafast and localized flow is able to puncture the membrane near the contact area with little mechanical perturbation to the rest of the structure. Membrane cutting is produced by the strong transient mechanical shear stress from the laser-induced cavitation bubble (Marmottant and Hilgenfeldt (2003) *Nature*, 423: 153-156; Lokhandwalla and Sturtevan (2001) *Phys. Med. Biol.* 46: 413-437; Hellman et al. (2008) *Biophoton.*, 1: 24-35). A delivery portal in the cell membrane is thereby generated without advancing the attached micropipette into the cell. The blade is in gentle contact with the membrane during cutting, eliminating the need for strong mechanical support underneath the membrane. This new device allows intracellular delivery of variably sized objects, from biomolecules to bacteria, into soft mammalian somatic cells with high efficiency and cell viability.

Figure 22A:
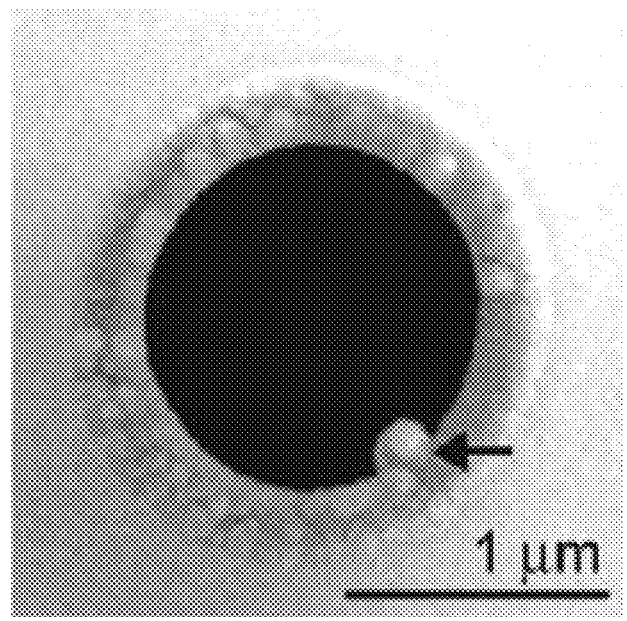
FIGS. 22A-22D show the structure of a Ti-coated micropipette and the calculated intensity pattern from laser excitation.
Figure 22B:
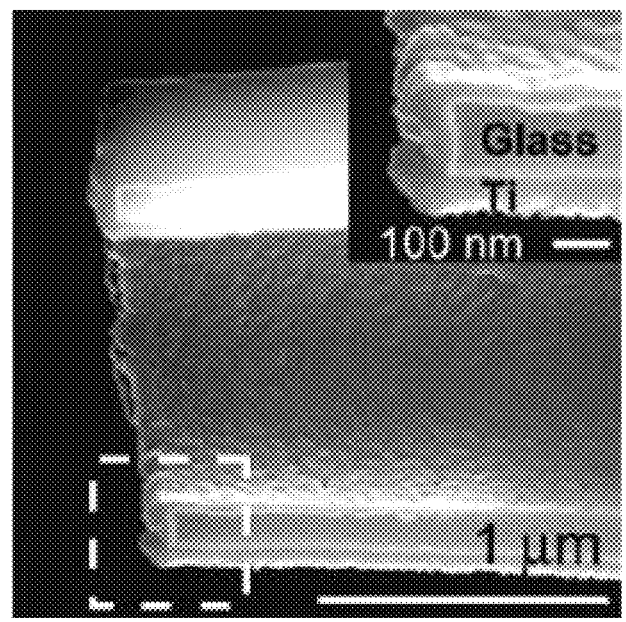

To demonstrate the photothermal nanoblade, a 100 nm thick titanium (Ti) thin film was deposited onto the tip of a glass microcapillary pipet with a 2 µm tip diameter (FIGS. 22A and 22B). The Ti coated micropipette is mounted on a motorized micromanipulator arm on an inverted microscope stage. With the micropipette tip positioned in light contact with a cell membrane, a 6 ns Nd: YAG laser pulse at 532 nm wavelength illuminated a 260 µm-wide field through the objective lens. Pulsed laser exposure rapidly heats the Ti and adjacent thin water layer to induce a localized vapor bubble explosion along the ring-shaped Ti thin film that cuts the contacting cell membrane. The process, from laser pulsing, Ti heating, cavitation bubble expansion, and collapse, takes only a few hundred nanoseconds. Pressure-controlled delivery of fluid and cargo inside the micropipette is synchronized with laser pulsing and membrane cutting.

Materials and Methods

Device Fabrication and Experimental Setup.

Titanium (Ti)-coated micropipettes were fabricated by heating and pulling (P-97, Sutter Instrument) a 1 mm diameter borosilicate glass capillary tube, followed by Ti thin film deposition onto the tapered ends using a magnetron sputter deposition system. The Ti coating thickness and the micropipette tip diameter were quantified using a scanning electron microscope. The laser pulse system was a Q-switched, frequency-doubled Nd:YAG laser (Minilite I, Continuum) operated at 532 nm wavelength and 6 ns pulsewidth.

The laser beam was split by a polarizing beam splitter with one arm sent into the fluorescence port of an inverted microscope (AxioObserver, Zeiss) and then through the objective lens (40×, 0.6 NA), to generate a 260 µm-wide laser spot on the sample plane. The optimized laser fluence used for cargo delivery was 180 mJ/cm². An electrical switch was built to synchronize the excitation laser pulse with the liquid injection system (FemtoJet, Eppendorf). A time-resolved imaging system to characterize the cavitation bubble dynamics was constructed using an intensified CCD camera (PI-MAX2, Princeton Instruments) with exposure times as short as 500 ps. A programmable delay between receiving the laser triggering signal and the camera shutter opening was set by the camera control unit. After the polarizing beam splitter, the other arm of the laser beam was sent through a fluorescent dye cell. The excited fluorescence pulse (wavelength centered ~698 nm) was coupled into a multimode fiber and then sent through the microscope condenser to illuminate the sample in synchronization with the camera shutter. A nanosecond time delay between the captured bubble image and the sample excitation laser pulse was controlled by the length of the optical fiber delay line.

Numerical Calculations of Intensity Pattern on the Ti-Coated Micropipette.

The 3D finite difference time domain (FDTD) method was used to simulate the electromagnetic intensity pattern (FullWAVE, RSoft Design Group). The simulation domain was constructed with a water medium region (nwater=1.34) and a glass micropipette ($n_{glass}$=1.46) with a 100 nm Ti ($n_{Ti}$=1.86+2.56i) thin film coated on the tip and the outer sidewall. The entire domain was surrounded by perfectly matched boundary layers to mimic an infinitely extending space. Plane wave excitation was used ($\lambda$=532 nm) with the electric field polarized along y and the wavevector k making a 30° angle with respect to the pipet tip. Time-averaged intensity profiles in Ti, $|E_{ave}|^2$, were obtained by averaging the normalized electric energy density over one electromagnetic wave oscillation.

Determining the Optimal Laser Fluence of the Photothermal Nanoblade for Membrane Cutting.

Criteria for optimal laser fluence, membrane opening, and maintaining high cell viability were sought. Propidium iodide (PI) dye was added to the cell culture media (10 μg/mL) before laser pulsing. The micropipette was brought into contact with the cell membrane and illuminated with a laser pulse at the specified fluence level. The treated cell was checked immediately after laser pulsing to verify the uptake of PI. Cell viability was determined separately in a similar fashion with PI added 90 min after laser pulsing, followed by visual growth detection over time.

Cell Viability Evaluation.

Cell viability was determined by annexin V and propidium iodide (PI) cell staining 90 min following photothermal nanoblade cutting. To accurately track injected cells, cells were seeded onto a chemically patterned glass coverslip substrate (Peterbauer et al. (2006) Lab Chip, 6: 857-863). Circular areas (diameter ~200 μm) were defined on the substrate to confine cell adhesion and growth within these regions. For each experiment, every cell within the same circular pattern (~60 cells in one pattern) was subjected to the same laser pulsing and cargo delivery conditions. To exclude the viability effects of culturing cells on a patterned substrate, the percentage of viable cells in a treated pattern was further normalized by the percentage of viable cells in a neighboring untreated pattern on the same glass substrate. Postdelivery viability was determined by the average of three independent experiments.

Biomolecule, Carboxylate Bead, and Bacterial Delivery with Immunofluorescence Imaging.

GFP-expressing RNA was diluted in 1×PBS, pH 7.4, and injected into IMR90 primary human lung fibroblasts. DsRed-encoding lentiviral DNA was incubated with cationic, 100 nm green polystyrene beads to allow DNA adsorption on the spherical surface. The beads were then suspended in 1×PBS, pH7.4, and injected into human embryonic stem (hES) cells. hES cells were dissociated and cultured using ROCK (Watanabe et al. (2007) Nat. Biotechnol. 25: 681-686) inhibitor on top of a thin layer of matrigel (BD Biosciences). DsRed expression was verified 24 h postinjection. Green carboxylate-modified polystyrene beads (200 nm) were suspended in 1×PBS, pH 7.4, (0.1% solid by volume) and injected into HEK293T cells. Fluorescent B. thailandensis bacteria were suspended in 1×PBS, pH7.4 (concentration $10^8$-$10^9$ per mL) and injected into HeLa cells. Cells were cultured in chambered microscope slides (LabTek, Nunc) using Dulbecco's modified Eagle's medium (DMEM) without penicillin and streptomycin. Immediately after the injection, cells were washed 3 times with PBS and incubated for 2 h in fresh medium containing 1000 mg/mL kanamycin to kill extracellular bacteria. The growth medium was then replaced with DMEM containing 5 mg/mL ceftazidime to suppress extracellular bacterial growth and incubated for an additional 16-24 h at 37° C. in 5% $CO_2$. At 16-24 h post injection, cells were fixed with 4% paraformaldehyde and stained with Alexa-Fluor-labeled phalloidin to visualize the actin cytoskeleton (Invitrogen). Cells were then visualized using a Leica SP2 AOBS laser scanning confocal microscope setup.

Bacterial Strains and Growth Conditions.

Burkholderia thailandensis and mutant derivates were cultured in L-medium. Chloramphenicol (25 μg/mL) or tetracycline (20 μg/mL) were added as required.

Bacterial Invasion Efficiency Assays.

B. thailandensis E264 was grown in L-broth to an optical density ($OD_{600}$) of 1.0 ($4 \times 10^8$ CFU/mL). In total, $1 \times 10^5$ HeLa cells grown in 12-well plates were infected with bacteria at a multiplicity of infection (MOI) of 10:1 for 2 h at 37° C. The infected cells were then washed with PBS and incubated with fresh medium containing 400 μg/mL kanamycin for 15 min to kill extracellular bacteria, followed by lysis with 1% Triton X-100 in PBS. Serial dilutions of the infected HeLa cell lysates were spread on L-agar, and the numbers of intracellular bacteria were determined by assays for CFU.

Results and Discussion.

Simulation of Optical Intensity Patterns on the Photothermal Nanoblade.

Figure 22C:
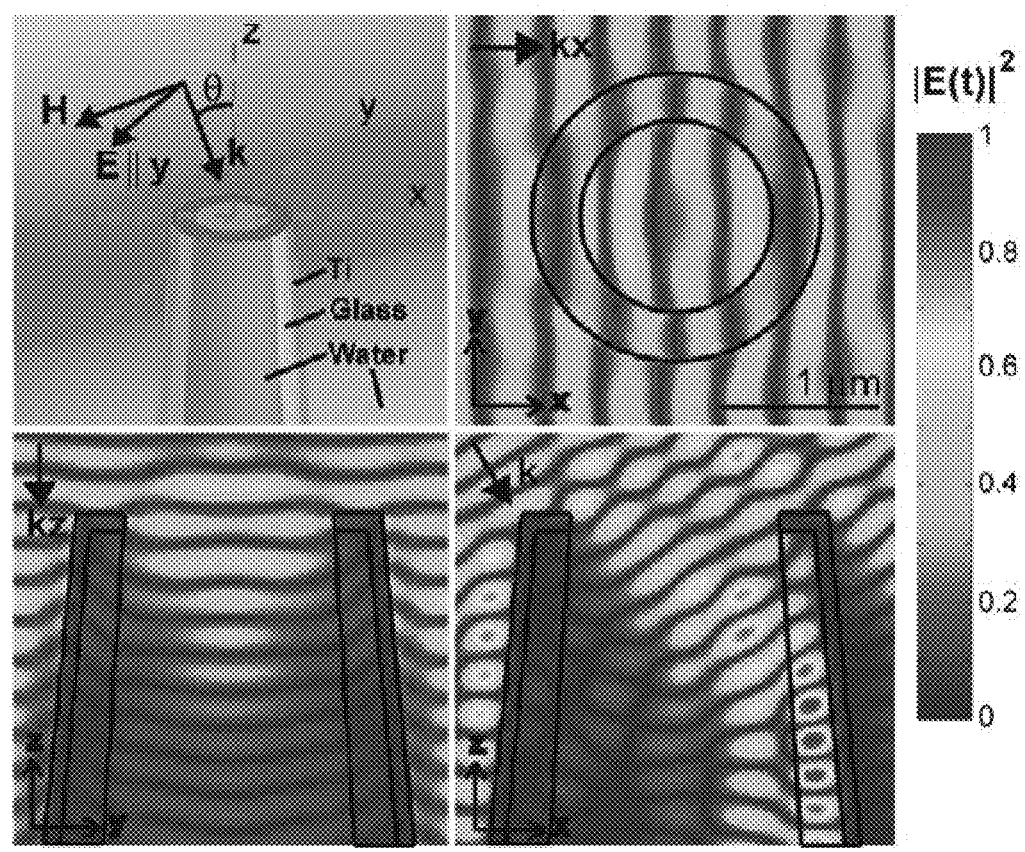
Figure 22D:
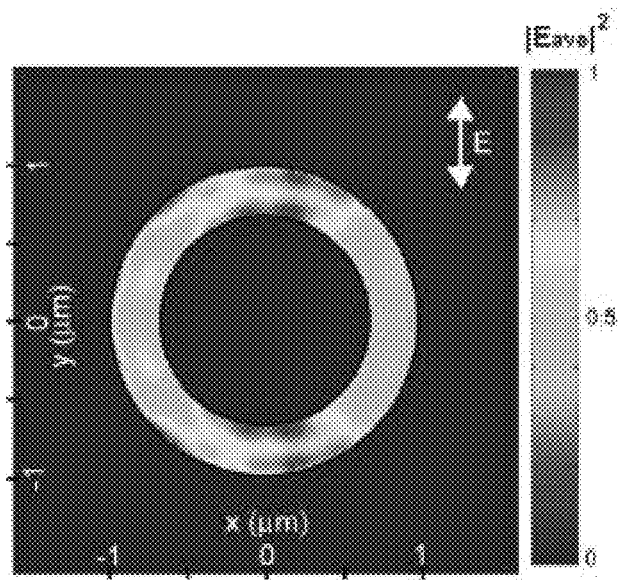
Figure 23A:
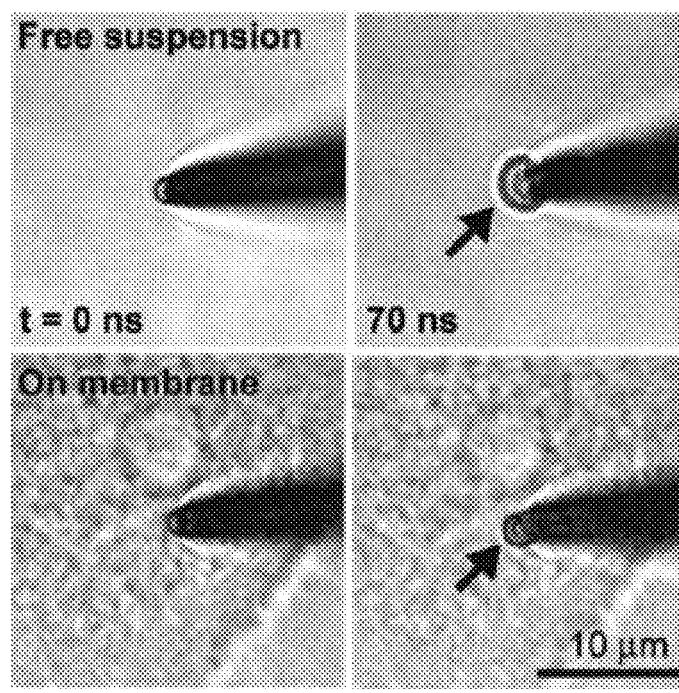
FIGS. 23A-23C illustrate ultrafast membrane cutting by the photothermal nanoblade and cell viability evaluation.

The cavitation bubble pattern is controlled by the thin film composition and configuration, as well as laser excitation parameters including wavelength, pulse duration, and energy. FIG. 22C shows the calculated intensity patterns on a laser-excited, Ti-coated micropipette using 3D finite difference time domain (FDTD) simulations. The Ti-coated micropipette is illuminated at an angle of 30° with respect to the tip. Plasmon-enhanced optical absorption ($\propto |E_{ave}|^2$) is nonuniform across a 2 μm wide Ti ring for linearly polarized light (FIG. 22D). High intensity areas are concentrated on the edges of the rings along the wave polarization direction. The temperature distribution in the Ti ring is governed not only by the heat generated in these high intensity areas but also by heat diffusion to the cooler metal regions and surrounding medium during laser pulsing. In the Ti film on the micropipette, the estimated heat diffusion length ($\sim (D\tau)^{1/2}$) is 230 nm in 6 ns. This results in a smoother temperature profile along the entire ring-shaped pipet tip. Consequently, thermal energy conducting away from the Ti film heats the adjacent thin water layer to above the critical temperature (Kotaidis et al. (2006) J. Chem. Phys. 124: 184702), generating a vapor nanobubble on the ringshaped micropipette tip (FIG. 23A).

Cavitation Bubble Induced Membrane Cutting and Corresponding Cell Viability.

Figure 23B:
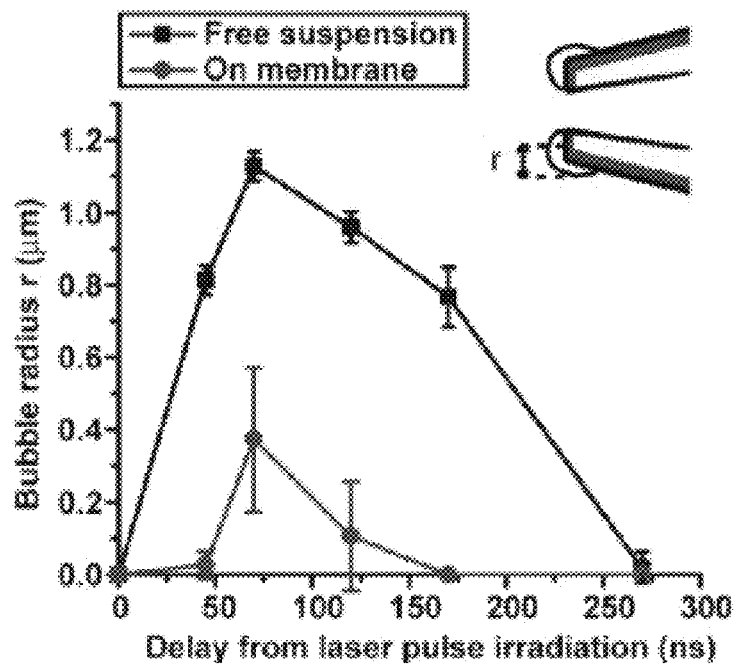
Figure 23C:
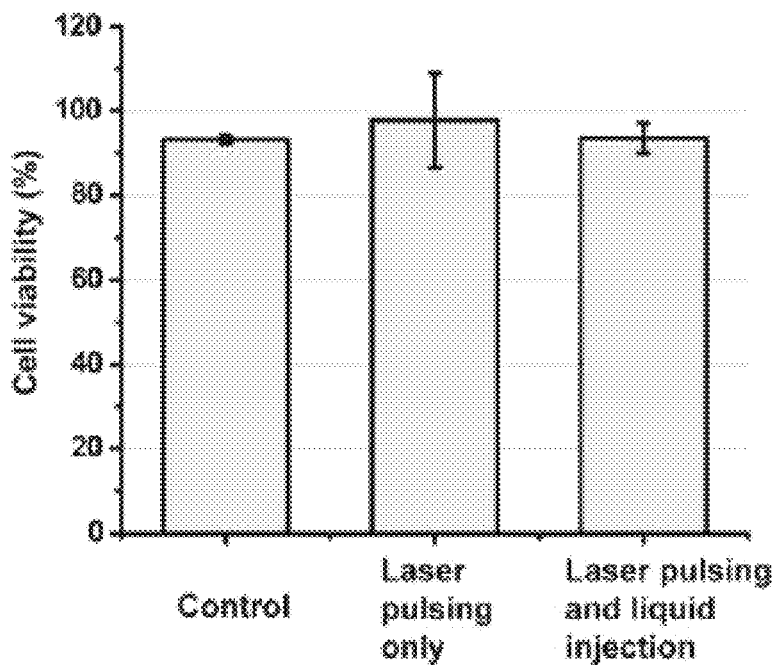

For micrometer-sized cargo delivery into live mammalian cells, a transient membrane portal is desired to accommodate the cargo size. Moreover, the damage zone is preferably contained to allow cell repair and maintain viability. FIG. 23A shows cavitation bubbles at the tip of a tilted Ti-coated micropipette 70 ns after laser pulse irradiation. A dramatic reduction in the bubble size was observed when the tip was in contact with the cell membrane as this interaction impedes bubble expansion. In this case the bubble grew to a maximum radius of 400 nm away from the rim of the tip in 70 ns and collapsed completely within 200 ns after the excitation laser pulse (FIGS. 23A and 23B). The blade tip never enters the cell so intracellular structural integrity is preserved, which helps foster rapid, reparative pore resealing, as evidenced by sustained cell viability (FIG. 23C). Cell viability was determined by annexin V and propidium iodide (PI) exclusion staining 90 min following laser pulsing. Under these conditions, >90% cell viability was obtained with laser pulsing and bubble explosion alone (at an optimal fluence of 180 mJ/cm$^2$) or when coupled with buffer injection into HeLa or HEK293T cells. Monitoring photothermal nanoblade treated cells over 24 h showed that cells stayed viable and continued to grow and divide as usual.

Biomolecules and Bacteria Delivery by the Photothermal Nanoblade.

Figure 24:
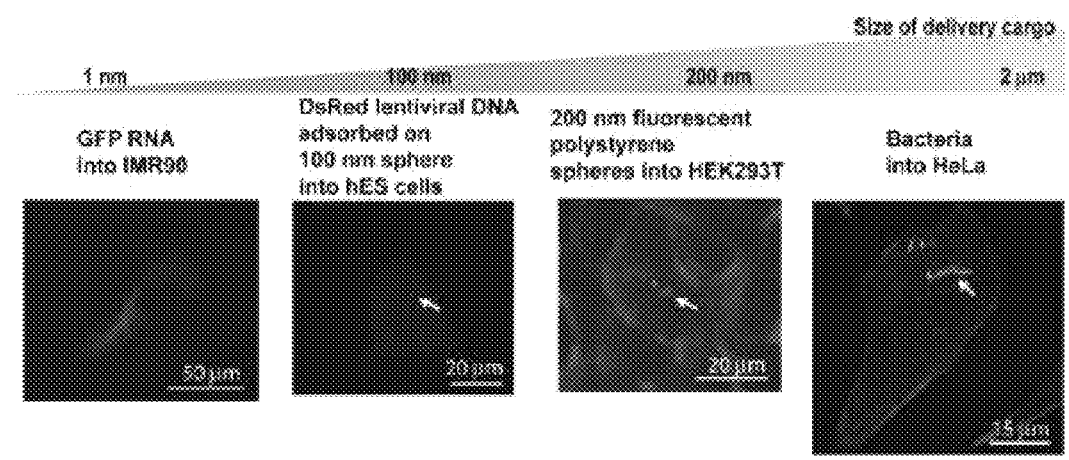
FIG. 24 illustrates the wide range of deliverable cargo sizes by the photothermal nanoblade. GFP-expressing RNA was delivered into lipofectamine-resistant IMR90 primary human lung fibroblasts. DsRed-containing lentivirus coated onto a 100 nm green fluorescent bead was expressed in ROCK inhibitor dispersed human embryonic stem cells following transfer. Fluorescent beads of 200 nm in diameter were delivered into HEK293T cells without clogging. *B. thailandensis* bacterial transfer into HeLa cells was achieved with high efficiency and high cell viability.
Figure 25A:
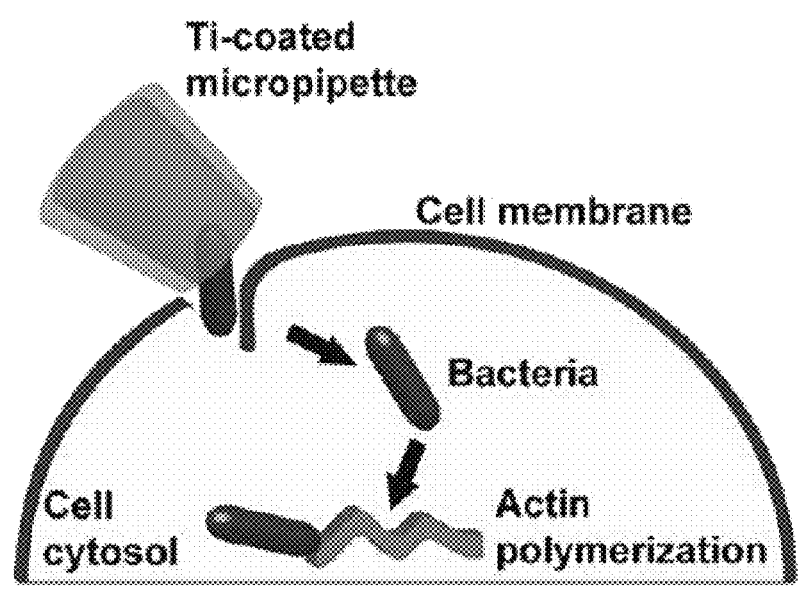
FIGS. 25A-25C illustrate high-efficiency bacterial delivery into HeLa cells by the phothermal nanoblade.
Figure 25B:
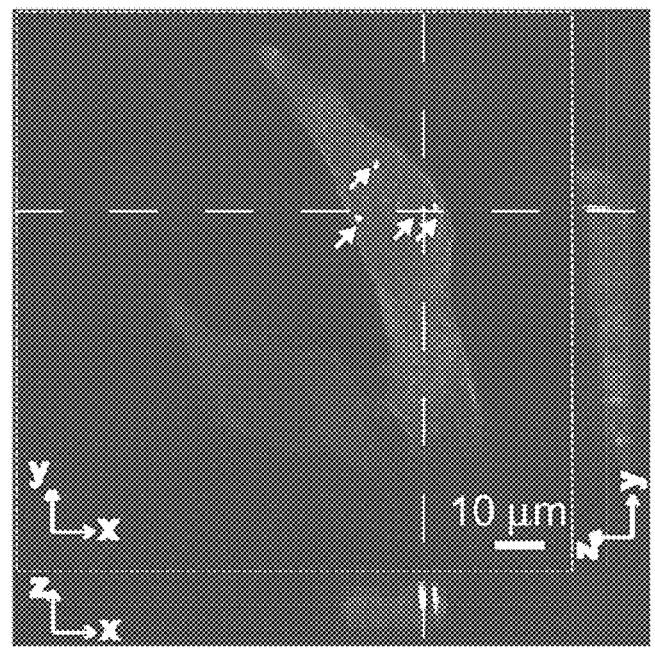

We tested the delivered cargo size range using the photothermal nanoblade on various cell types. GFP-expressing RNA was efficiently delivered into lipofectamine-resistant IMR90 primary human lung fibroblasts, and a DsRed-containing lentivirus coated onto 100 nm green fluorescent polystyrene beads was successfully expressed in ROCK38 inhibitor dispersed human embryonic stem cells following injection. Fluorescent beads of 200 nm in diameter were delivered without clogging, as were micrometer-sized bacteria (FIG. 24). We further evaluated an intracellular bacterium as the largest and most fragile cargo delivered by this approach (FIG. 25). *Burkholderia thailandens* is a rod-shaped bacteria measuring ~0.7 µm×2 µm. To determine injection efficiency, GFP-labeled bacteria were suspended in buffer at a concentration of ~5×10$^8$ per mL, 2 orders of magnitude higher than conventional microinjection (Goetz et al. (2001) *Proc. Natl. Acad. Sci. U.S.A.*, 98: 12221-12226). High cargo concentration is critical in achieving high delivery efficiency since the liquid volume delivered into a cell is limited to ~1 pL. Without a high concentration, the frequency of ejecting 1 bacterium per injection is low. In our experiment, upon laser pulsing and cell membrane opening, 1-5 pL of the bacterial solution was ejected out of the pipet, corresponding to an average of ~1 bacteria per injection. Not all the ejected solution was delivered into the cell since the pipet tip was in light contact with the cell membrane, and the bore of the pipet was not in a perfect seal with the membrane after cutting. Under this condition, we obtained an average delivery efficiency of 46% from multiple independent experiments.

Figure 25C:
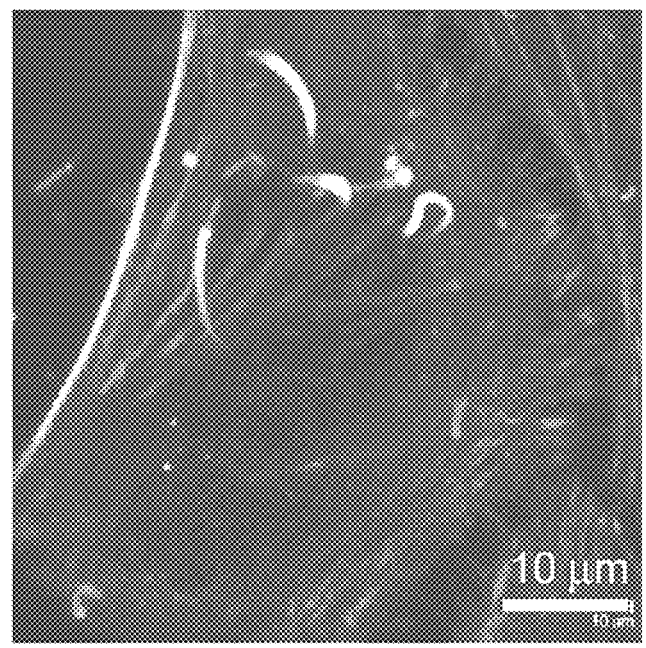

We further evaluated the natural bacterial invasion efficiency in HeLa cells by incubating cells with *B. thailandensis* for 2 h. The delivery efficiency by photothermal injection is 2 orders of magnitude higher than the natural HeLa cell infectivity of *B. thailandensis* of 0.8%. Importantly, bacteria remained viable and were protected from destruction during bubble cycles within the glass pipet and from shearing during injection by the large bore tip opening as verified by bacteria multiplication and actin polymerization (Stevens et al. (2005) *J. Bacteriol.*, 187: 7857-7862) in the injected cells 24 h after transfer (FIG. 25C).

Reliability Evaluation of the Photothermal Nanoblade.

For robust operation, the metallic thin film desirably withstands high temperature and intense pressure from the shockwave and high speed flows generated by cavitation bubbles. Ti was chosen as the coating material for its higher melting temperature and strong adhesion to the glass substrate compared with other inert metals such as gold (Benjamin and Weaver (1961) *Proc. R. Soc. London, Ser. A,* 261: 516-531). It has been shown in our experiments that a gold coated micropipette failed after a few laser pulses due to thin film damage. We verified that a Ti-coated micropipette remained functional through at least 50 laser pulsing and bubble explosion cycles.

Conclusions.

The photothermal nanoblade described in this example holds promise for delivering currently untransferable large cargo into mammalian cells, such as chromosomes, organelles, and intracellular pathogens, that are beyond the size constraints of contemporary delivery approaches. An additional advantage of the photothermal nanoblade is its ease of use. Since membrane cutting is controlled by the laser pulse energy and the Ti coating configuration, the user simply positions the micropipette tip in gentle contact with the cell membrane to perform delivery. By contrast, for conventional glass microcapillary microinjection, delivery efficiency and cell viability are strongly influenced by the manner in which the glass needle enters the cell (e.g., speed, force, angle). As a result, the conventional method requires substantial training and experience for a user to become proficient. There is also less chance to break the fragile micropipette tip using the photothermal nanoblade since it does not require a rapid "zig-zag" motion for the micropipette to penetrate and leave the cell. The photothermal nanoblade does not operate under any specific surface plasmon resonance modes in the current demonstration. Further optimization of the metallic nanostructure to match the excitation laser wavelength could reduce the threshold laser energy for exciting cavitation bubbles.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A device for delivering an agent into a cell, said device comprising:

a vessel comprising walls and a floor where the walls and/or floor comprise a plurality of orifices leading outside said vessel, wherein nanoparticles and/or a thin film of a material is disposed on said walls and/or floor at and/or near each of the orifices comprising said plurality of orifices, wherein said material is one that that heats up when illuminated by a laser or non-coherent light source;

a laser or non-coherent light source directed to all or to a portion of the nanoparticles or thin film, wherein said laser or non-coherent light source is capable of heating said nanoparticles or thin film to a temperature sufficient to generate cavitation bubbles in a fluid in said vessel; and wherein said device is configured for delivering said agent into said vessel through one or more orifices comprising said plurality of orifices to selectively deliver said agent into cells disposed at or near said one or more orifices via the formation of cavitation bubbles when the nanoparticles or thin film at or near said one or more orifices is heated by said laser or non-coherent light source.

2. The device of claim 1, wherein said vessel comprises a well in a microtiter plate, a cell culture vessel, or a chamber or channel in a microfluidic device.

3. The device of claim 1, wherein said vessel comprises a chamber configured to contain cells and disposed for viewing with a microscope.

4. The device of claim 1, wherein plurality of orifices comprises at least 5 orifices.

5. The device of claim 1, wherein said nanoparticles and/or a thin film are deposited on a wall and/or all around the lip of said each of the orifices comprising said plurality of orifices.

6. The device of claim 1, wherein said nanoparticles and/or thin film comprise a thin film.

7. The device of claim 1, wherein said nanoparticles and/or thin film comprise a material selected from the group consisting of a semiconductor, a metal, a metal alloy, a metal nitride, a metal oxide, a transition metal, a transition metal alloy, a transition metal nitride, and a transition metal oxide.

8. The device of claim 7, wherein the nanoparticle and/or thin film comprise a material selected from the group consisting of gold, titanium (Ti), TiN, TiCn, and TiAlN.

9. The device of claim 1, wherein said one or more orifices are in fluid communication with a chamber or a microchannel containing said agent.

10. The device of claim 9, wherein said device comprises a plurality of microchannels and different microchannels are in fluid communication with different orifices comprising said plurality of orifices.

11. The device of claim 9, wherein said microchannel(s) are pressurized, under control of a pump, or fed by a gravity feed.

12. The device of claim 9, wherein said device further comprises a controller that monitors and/or controls flow in said microchannel and controls timing and, optionally, location of the illumination of said surface.

13. The device of claim 1, wherein said device is configured to replace the stage on an inverted microscope.

14. The device of claim 1, wherein a cell is disposed on said surface.

15. The device of claim 1, wherein said laser or non-coherent light source comprises a laser.

16. The device of claim 1, wherein said nanoparticles and/or a thin film are preferentially on one region of a wall or lip of each of the orifices comprising said plurality of orifices.

17. The device of claim 1, wherein said nanoparticles and/or a thin film are deposited on the face of the surface and/or on the lip of each of the orifices comprising said plurality of orifices on the same side on which cells are disposed.

18. The device of claim 1, wherein said nanoparticles and/or a thin film are deposited on the face of the surface and/or on the lip of each of the orifices comprising said plurality of orifices opposite the side on which cells are disposed.

19. The device of claim 9, wherein said chamber or microchannel is pressurized, under control of a pump, or fed by a gravity feed.

20. The device of claim 19, wherein said device further comprises a controller that monitors and/or controls flow in said microchannel and controls timing and, optionally, location of the illumination of said surface.

21. The device of claim 1, wherein said device is configured to generate a cavitation bubble at a side of a cell membrane that is proximal to an orifice comprising said plurality of orifices, wherein said cavitation bubble opens the proximal cell membrane delivering said agent through the disrupted proximal cell membrane.

22. The device of claim 1, wherein the plurality of orifices are in fluid communication with a microchannel.

23. The device of claim 1, wherein the plurality of orifices are in fluid communication with a manifold.

24. The device of claim 1, wherein a first subset of the plurality of orifices are in fluid communication with a first manifold, and a second subset of the plurality of orifices are in fluid communication with a second manifold.

25. The device of claim 1, further comprising an external pressure source configured to deliver reagents through the plurality of orifices into the cells.

* * * * *